(12) United States Patent
Deiters et al.

(10) Patent No.: US 11,214,779 B2
(45) Date of Patent: Jan. 4, 2022

(54) ACTIVATABLE CRISPR/CAS9 FOR SPATIAL AND TEMPORAL CONTROL OF GENOME EDITING

(71) Applicants: University of Pittsburgh—Of the Commonwealth System of Higher Education, Pittsburgh, PA (US); The University of North Carolina at Chapel Hill, Chapel Hill, NC (US)

(72) Inventors: Alexander Deiters, Pittsburgh, PA (US); James B. Hemphill, Cambridge, MA (US); Aravind Asokan, Chapel Hill, NC (US); Erin Borchardt, Carrboro, NC (US)

(73) Assignees: University of Pittsburgh—Of the Commonwealth System of Higher Education, Pittsburgh, PA (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/559,898

(22) PCT Filed: Apr. 8, 2016

(86) PCT No.: PCT/US2016/026753
§ 371 (c)(1),
(2) Date: Sep. 20, 2017

(87) PCT Pub. No.: WO2016/164797
PCT Pub. Date: Oct. 13, 2016

(65) Prior Publication Data
US 2018/0073002 A1    Mar. 15, 2018

Related U.S. Application Data

(60) Provisional application No. 62/144,741, filed on Apr. 8, 2015.

(51) Int. Cl.
| | |
|---|---|
| *C12N 9/00* | (2006.01) |
| *C12N 9/22* | (2006.01) |
| *C12N 15/10* | (2006.01) |
| *C12N 15/52* | (2006.01) |
| *C12N 15/85* | (2006.01) |
| *A61K 48/00* | (2006.01) |
| *C12N 13/00* | (2006.01) |
| *C12N 15/90* | (2006.01) |

(52) U.S. Cl.
CPC ............. *C12N 9/22* (2013.01); *A61K 48/005* (2013.01); *C12N 13/00* (2013.01); *C12N 15/102* (2013.01); *C12N 15/52* (2013.01); *C12N 15/85* (2013.01); *C12N 15/907* (2013.01)

(58) Field of Classification Search
None
See application file for complete search history.

(56) References Cited

U.S. PATENT DOCUMENTS

| | | |
|---|---|---|
| 8,697,359 B1 | 4/2014 | Zhang |
| 2013/0005019 A1 | 1/2013 | Chin et al. |
| 2013/0183761 A1 | 7/2013 | Chin et al. |
| 2014/0273226 A1 | 9/2014 | Wu |

FOREIGN PATENT DOCUMENTS

WO    WO 2011/107747 A2    9/2011

OTHER PUBLICATIONS

Hemphill et al., "Optical Control of CRISPR/Cas9 Gene Editing," *J Am Chem Soc.* 137:5642-5645, 2015.
Luo et al., "Genetically Encoded Optochemical Probes for Simultaneous Fluorescence Reporting and Light Activation of Protein Function with Two-Photon Excitation," *J Am Chem Soc.* 136:15551-15558, 2014.
Nihongaki et al., "CRISPR-Cas9-based photoactivatable transcription system," *Chem Biol.* 22:169-174, 2015.
Polstein et al., "A light-inducible CRISPR-Cas9 system for control of endogenous gene activation," *Nature Chem Biol.* 7 7:198-200, 2015.
PCT/US2016/0267 PCT/US2016/026753 International Search Report and Written Opinion dated Jul. 27, 2016 (12 pages).

*Primary Examiner* — Celine X Qian
(74) *Attorney, Agent, or Firm* — Klarquist Sparkman, LLP

(57) ABSTRACT

Disclosed herein is a genetically encoded light- or chemically-activated Cas9 engineered through the site-specific installation of an activatable lysine amino acid. Such activatable Cas9 proteins can be used in CRISPR/Cas9 systems to control gene expression temporally, spatially, or both. Systems, methods, kits, and compositions for manipulation of sequences and/or activities of target sequences are provided. Also provided are methods of directing CRISPR complex formation in cells and methods for selecting specific cells by introducing precise mutations utilizing the CRISPR/Cas9 system.

10 Claims, 15 Drawing Sheets
Specification includes a Sequence Listing.

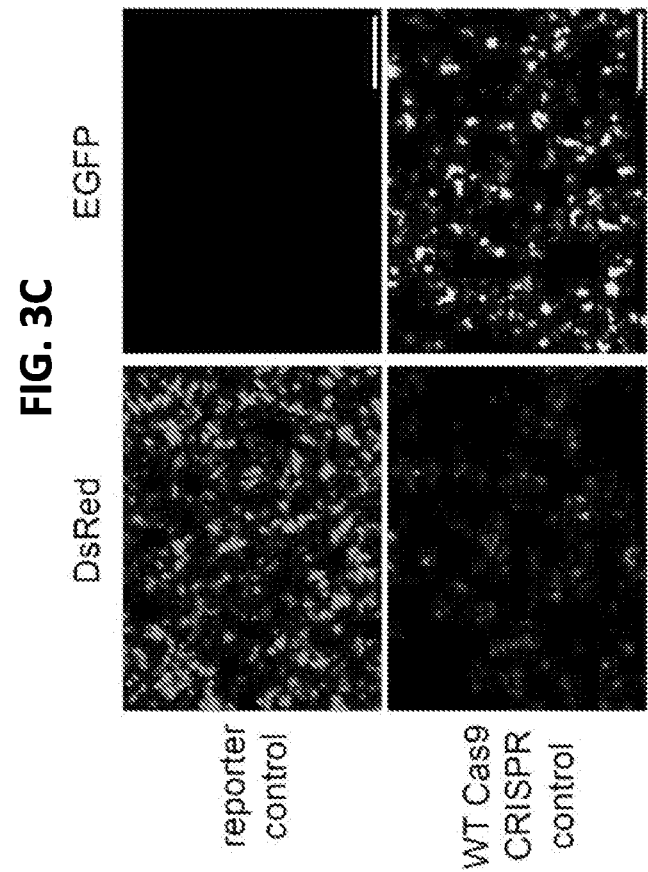
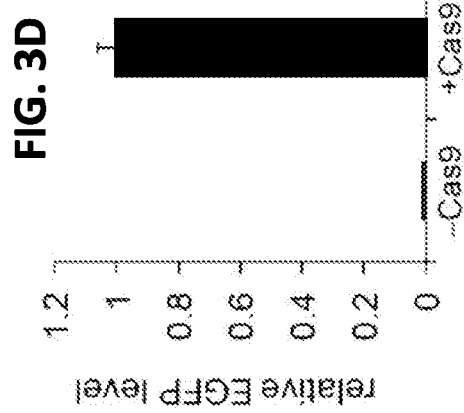
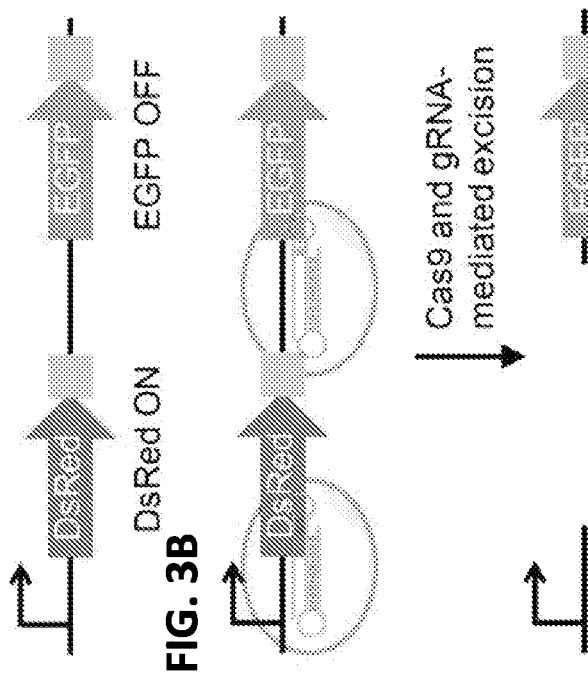

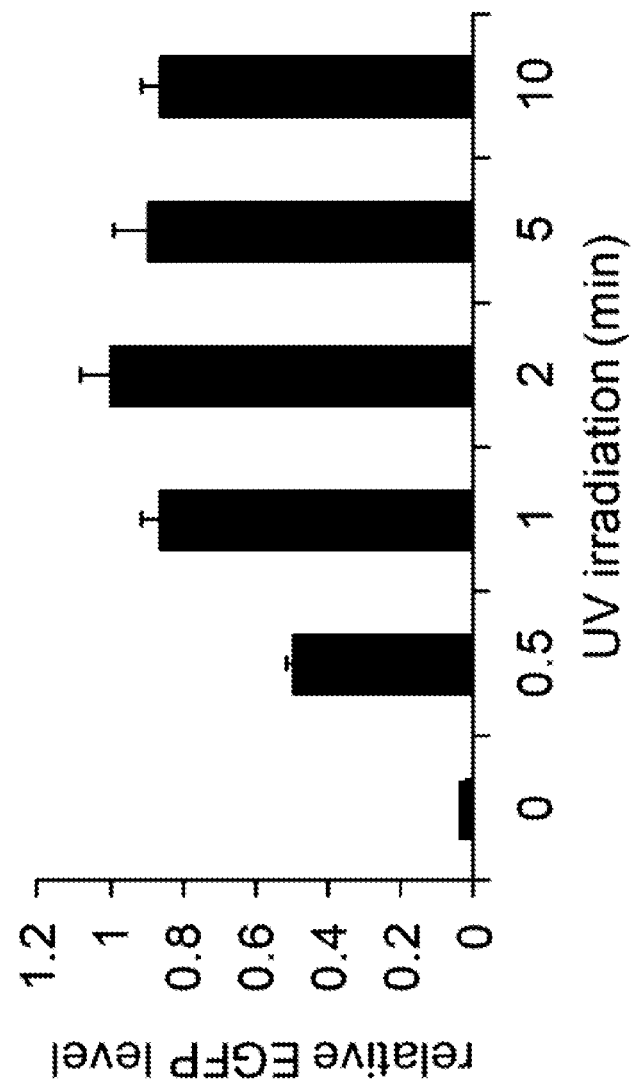
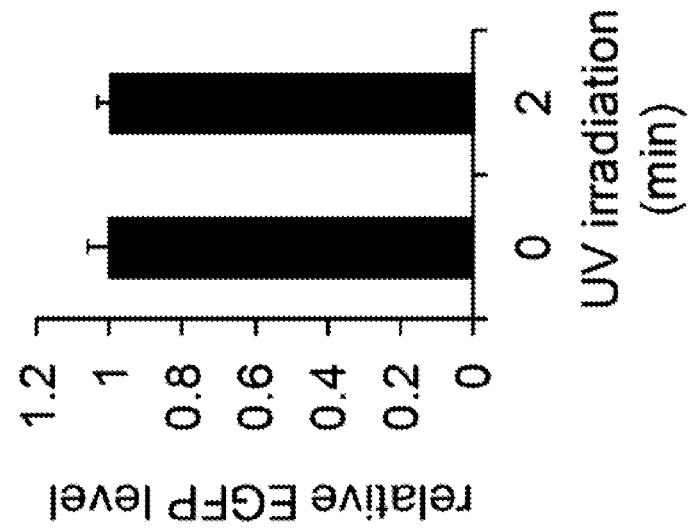

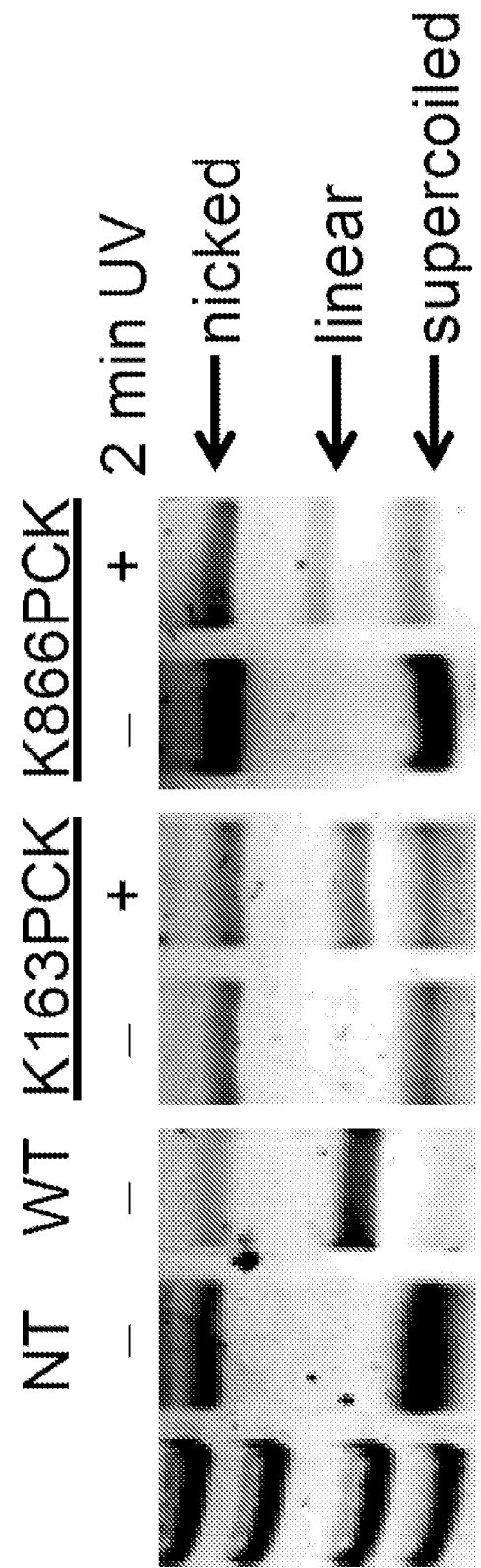

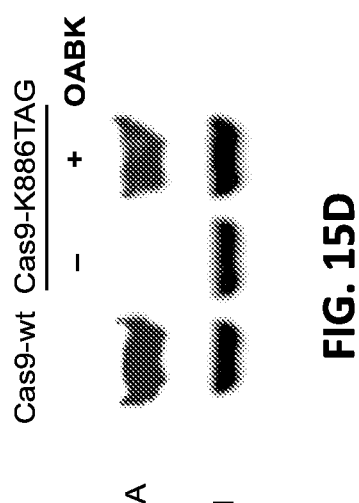
FIG. 15A
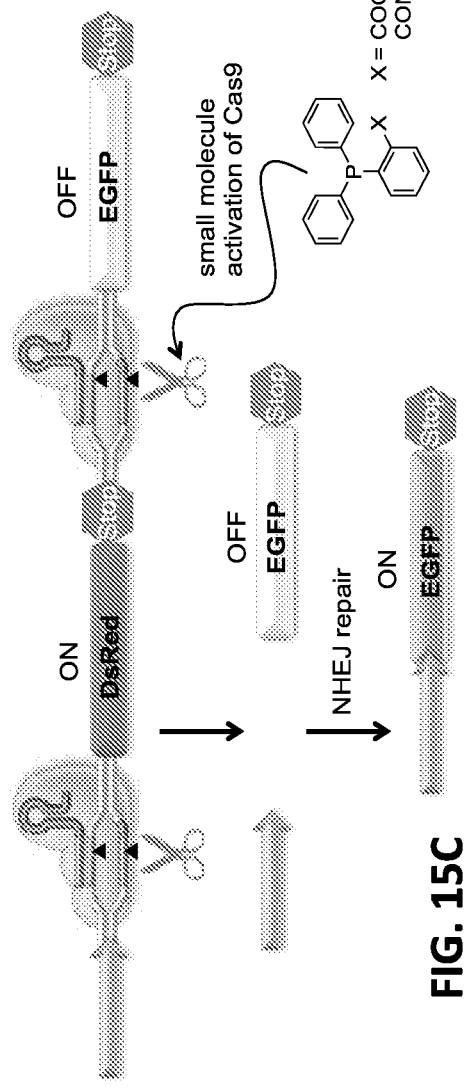
FIG. 15C
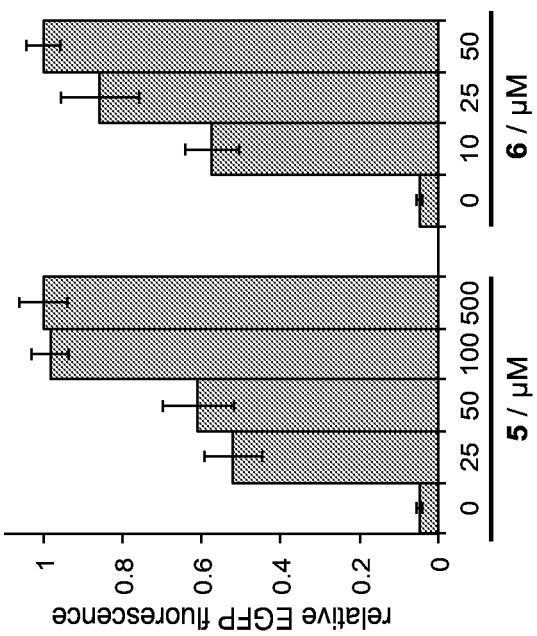
FIG. 15B
FIG. 15D

ACTIVATABLE CRISPR/CAS9 FOR SPATIAL AND TEMPORAL CONTROL OF GENOME EDITING

CROSS-REFERENCE TO RELATED APPLICATION

This is the U.S. National Stage of International Application No. PCT/US2016/026753, filed Apr. 8, 2016, which was published in English under PCT Article 21(2), which in turn claims the benefit of U.S. Application No. 62/144,741, filed Apr. 8, 2015, herein incorporated by reference in its entirety.

ACKNOWLEDGMENT OF GOVERNMENT SUPPORT

This invention was made with government support under MCB-1330746 awarded by the National Science Foundation and RO1HL089221 and 1R01GM112728 awarded by the National Institutes of Health. The government has certain rights in the invention.

FIELD

This disclosure relates to activatable Cas9 proteins and their use for spatial and temporal control of gene editing using the CRISPR/Cas9 system.

BACKGROUND

Many bacteria and archaea utilize an adaptive immune defense based on a system of clustered regularly interspaced short palindromic repeats (CRISPR) that target invasive nucleic acids through the interaction of CRISPR-associated proteins (Cas) and CRISPR arrays which are transcribed and processed into short CRISPR RNAs (crRNA) (Wiedenheft et al., *Nature* 2012, 482 (7385), 331-8). The crRNA guides the Cas proteins to sequence-specific duplex cleavage. Type II CRISPR systems employ an additional RNA, the trans-activating crRNA (tracrRNA) which hybridizes with the crRNA (Garneau et al., *Nature* 2010, 468 (7320), 67-71; Deltcheva, E. et al., *Nature* 2011, 471 (7340), 602-7). These RNAs can be combined to allow Cas9 targeting with a single guide RNA (gRNA) (Jinek et al., *Science* 2012, 337 (6096), 816-21). The Cas9 enzyme has been optimized for site-specific DNA cleavage and nicking followed by non-homologous end-joining (NHEJ) or homology-directed repair (HR), enabling gene editing, gene deletion, and gene mutation (Hsu et al., *Nat Biotechnol* 2013, 31 (9), 827-32; Ran et al., *Cell* 2013, 154 (6), 1380-9) in human cells (Mali et al., *Science* 2013, 339 (6121), 823-6) and animal models (Gratz et al., *Genetics* 2013, 194 (4), 1029-35; Wang et al., *Cell* 2013, 153 (4), 910-8). The ease of customized gRNA design allows for sequence-specific gene targeting (and the ability to multiplex) without the need for protein engineering, the ability to introduce both nicks and dsDNA breaks, and high efficiency of these processes (Straub et al., *Mol Plant* 2013, 6 (5), 1384-7; Niu et al., *Mol Biotechnol* 2014, 56 (8), 681-8). In addition, a catalytically inactive Cas9 has been engineered into a transcriptional activator and repressor, expanding the utility of Cas9 as a gene regulatory tool (Gilbert et al., *Cell* 2013, 154 (2), 442-51).

The CRISPR/Cas9 system has emerged as an innovative tool in biomedical research for a wide range of applications, with potential for customized genome engineering and gene therapy as well as treatment of viral infections. Its programmability and promise for therapeutic intervention and as a biomedical research tool has surpassed zinc-finger nucleases and TALENs leading to commercialization attempts. However, precise spatial and temporal control of CRISPR/Cas9-mediated gene editing are needed.

SUMMARY

Disclosed herein is an activated CRISPR/Cas9 system for conditional control (e.g., spatial or temporal) of gene editing and gene expression in cells. In order to achieve conditional control of the CRISPR/Cas9 system, light-activated and chemical-activated Cas9 proteins were engineered through the site-specific installation of a caged lysine or a chemically-activatable lysine, respectively. Specific lysine residues were identified as activatable sites that can be modified to optically or chemically control Cas9 function. The function of the caged Cas9 was demonstrated through activation and deactivation of both exogenous and endogenous gene function. Based on these results, provided are methods that allow precise spatial and temporal control of gene editing (thereby potentially removing off-target effects in the repair of genomic mutations or providing exclusive targeting of disease tissue), repression of gene expression (through precise epigenetic modification), and activation of gene expression (through recruitment of transcriptional activator domains) (for example using an activatable catalytically dead "dCas9" enzyme, e.g., an activatable version of SEQ ID NO: 41).

Provided herein are non-naturally occurring activatable Cas9 proteins. Such proteins include at least one light activated lysine (e.g., using photocaged lysine, PCK) or at least one chemically activatable lysine. Exposure of the light activated/caged lysine to light (such as UV or visible light) activates the Cas9, while exposure of the chemically activatable lysine to the appropriate chemical (for example if the protected lysine analog is ortho-azidobenzyloxycarbonyl lysine (OABK), the Cas9 can be exposed to a phosphine or derivative thereof). Such small-molecule activation of Cas9 can allow conditional control of gene editing in tissues and systems that are not amenable to light activation.

In some examples, the activatable Cas9 protein includes a light activatable lysine (e.g., PCK) at amino acid position 163, 810, 848, 855, 866, or 974. In some examples, the activatable Cas9 protein includes a chemically activatable lysine (e.g., protected lysine analog) at amino acid position 163, 810, 848, 855, 866, or 974. Thus, the activatable Cas9 protein can have at least 80%, at least 85%, at least 90%, at least 95%, at least 98%, or at least 99% sequence identity to SEQ ID NO: 39 or 41, wherein the protein includes a light activatable lysine (e.g., PCK) at amino acid position 163, 810, 848, 855, 866, or 974 or a chemically activatable lysine at amino acid position 163, 810, 848, 855, 866, or 974. In some examples, the activatable Cas9 protein comprises SEQ ID NO: 39 or 41, wherein the lysine at amino acid position 163, 810, 848, 855, 866, or 974 is photocaged or chemically activatable.

Also provided are isolated nucleic acid molecules that encode the disclosed activatable Cas9 proteins. For example, such isolated nucleic acid molecules can have at least 80%, at least 85%, at least 90%, at least 95%, at least 98%, or at least 99% sequence identity to SEQ ID NO: 38 or 40, wherein the nucleic acid molecule has an amber stop codon (TAG) (or other stop codon or 4 base codon) at a position encoding amino acid position 163, 810, 848, 855, 866, or 974. In one example, the isolated nucleic acid molecule includes SEQ ID NO: 38 or 40, and an amber stop codon (TAG) (or other stop codon or 4 base codon) at a position encoding amino acid position 163, 810, 848, 855, 866, or 974. Vectors, such as a plasmid or viral vector, which include a nucleic acid molecule encoding an activatable Cas9 protein, are provided. Such vectors may include a promoter operably linked to the activatable Cas9 protein coding sequence. Also provided are recombinant cells that include nucleic acid molecules encoding an activatable Cas9 protein, as well as vectors including such coding sequences. In some examples the recombinant cell is a recombinant eukaryotic cell or a recombinant bacterial cell (such as *E. coli*).

The disclosure also provides kits that include one or more of the disclosed activatable Cas9 proteins, nucleic acid molecules encoding activatable Cas9 protein, nucleic acid molecules representing or encoding the guide nucleic acid (e.g., gRNA), vectors including such coding sequences, as well as recombinant cells including such vectors or nucleic acids. Such kits can include other components, such as growth media (e.g., that allow growth of bacterial, fungal, plant, yeast, or mammalian cells), OABK, PCK, an isolated nucleic acid molecule encoding pyrrolysyl tRNA, an isolated nucleic acid molecule encoding a tRNA synthetase, an isolated guide nucleic acid molecule specific for a target nucleic acid molecule, a phosphine or derivative thereof, or combinations thereof. In some examples, such kits include reagents for transfection or transformation. In some examples, such kits include plasmid or viral vectors.

Methods of using the disclosed activatable Cas9 proteins and nucleic acid molecules in a CRISPR/Cas9 gene editing method are provided. In one example, the method is a method of altering expression (e.g., increase or decrease) of at least one target gene in a cell. The disclosed methods allow for temporal or spatial control of gene expression, as the CRISPR/Cas9 can be activated at a specific time (e.g., during a specific time in development), or in a specific area (e.g., in specific cells or tissues), or both. The cell can be in culture (e.g., ex vivo), or the cell can be present in an organism, such as *C. elegans, Drosophila, Xenopus*, zebrafish, mouse, rat, rabbit, or an embryo of such an organism. In some examples, the cell is in a human. Such a method can include introducing an activatable Cas9 protein and a guide nucleic acid specific for the at least one target gene into the cell. The activatable Cas9 protein and a guide nucleic acid can be part of a complex, which is introduced into the cell. The cell is then exposed to light or a chemical (depending on the activatable lysines in the Cas9), thereby activating the activatable Cas9 protein and altering expression of the at least one target gene in the cell. In another example, instead of introducing an activatable Cas9 protein into the cell, coding nucleic acid molecules are used instead, and the activatable Cas9 is expressed from a coding sequence introduced into the cell. For example, the method can include introducing into the cell (1) an isolated nucleic acid molecule (such as a vector) encoding a activatable Cas9 protein, (2) a guide nucleic acid molecule specific for the at least one target gene, (3) an isolated nucleic acid molecule encoding a tRNA (such as pyrrolysyl tRNA), and (4) an isolated nucleic acid molecule encoding a tRNA synthetase. The cell is then exposed to light or a chemical (depending on the activatable lysines in the Cas9), thereby activating the activatable Cas9 protein and altering expression of the at least one target gene in the cell. For example, if the activatable Cas9 protein includes a light activatable lysine (e.g., PCK), the cell is exposed to light (such as UV light), or if the activatable Cas9 protein includes OABK, the cell is exposed to a phosphine or a phosphine derivative.

The foregoing and other features of the disclosure will become more apparent from the following detailed description, which proceeds with reference to the accompanying figures.

BRIEF DESCRIPTION OF THE DRAWINGS

FIGS. 3A-3D shows the dual reporter CRISPR/Cas9 activity assay. A) Depiction of the dual reporter locus. A DsRed gene (red arrow) and an EGFP gene (green arrow) are separated by a transcription termination sequence (grey boxes). In the absence of Cas9, transcription terminates immediately following DsRed, allowing only DsRed expression. B) When functional Cas9 (blue) and gRNAs (orange) are present, the complex mediates excision of the DsRed-terminator cassette and NHEJ repair allows expression of EGFP. C) Wild-type Cas9 gene editing of the fluorescent dual reporter construct. HEK293T were transfected with the dual reporter and Cas9 expression plasmids, then DsRed/EGFP fluorescence was observed at 48 hours. Scale bars indicate 200 µm. D) Analysis of EGFP expression by imaging cytometry. Error bars represent standard deviations from three replicates.

FIGS. 8A-8B are bar graphs showing Cas9 UV irradiation optimization. The wild-type (A) and K866-caged Cas9 mutant (B) expression plasmids were transfected into cells with the dual reporter system and PCK incorporation constructs, then grown in the presence of PCK (2 mM) for 24 hours. The cells were then UV irradiated for 0-10 minutes and imaged after 48 hour incubation. The images were counted for EGFP expressing cells. Error bars represent the standard deviations of three replicates.

FIG. 9 is a digital image showing Cas9 DNA cleavage assays. The Cas9 proteins were expressed in HEK293T cells and purified from lysate. Cas9 purifications were incubated with the dual reporter plasmid and EGFP gRNA overnight at 37° C. then analyzed on an agarose gel.

FIGS. 15A-15D show activation of OABK-Cas9 in the presence of a phosphine derivative. A) Schematic design of the CRISPR/Cas9 activity assay using the pIRG dual reporter. B) Anti-HA western blot showing amino acid-dependent expression of modified Cas9 in HEK 293T cells without or with OABK (0.25 mM), as well as a GAPDH loading control. C) Small-molecule control of CRISPR/Cas9 gene editing in HEK 293T cells using the pIRG reporter. Residual DsRed fluorescence was still observed, due to reporter expression during the 24 h incubation before small molecule activation. Scale bar represents 100 µm. D) EGFP expression in response to activation of Cas9 with varied concentrations (0-500 µM) of 5 and 6 (see FIG. 14). EGFP expression was analyzed using imaging cytometry by counting fluorescent cells in four randomly selected fields of view per well. Data was analyzed using ImageJ. Error bars represent standard deviations from three independent experiments.

SEQUENCE LISTING

Figure 1A:
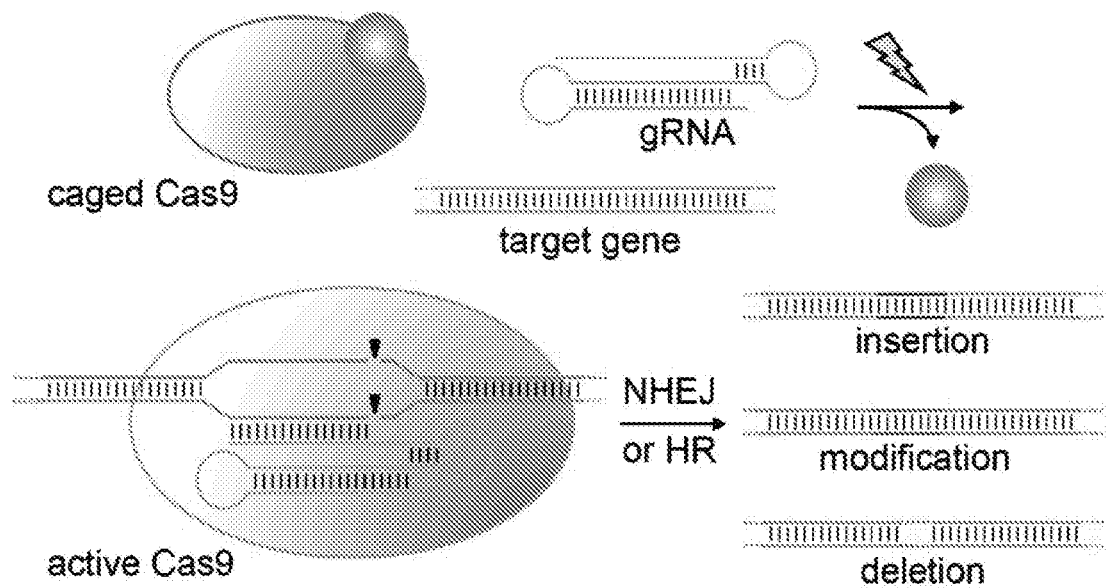
FIGS. 1A-1D. A) Light-activation of caged Cas9 enables optochemical control of gene editing. The caged Cas9 protein contains a site-specifically incorporated photocaged lysine, rendering it inactive until the caging group is removed through light exposure. This generates wild-type Cas9 that induces sequence-specific DNA cleavage followed by subsequent non-homologous end joining (NHEJ) or homology-directed repair (HR). B) K866 (red) conformation before (left) and after (right) gRNA binding. Renderings are based on PDB 4CMP and 4OO8. C) Photocaged lysine (PCK), with the photocleavable caging group shown in red. D) Western blot of PCK-dependent Cas9 K866TAG expression.

The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The sequence listing generated on Jun. 17, 2019, 48 Kb, and submitted herewith, is herein incorporated by reference.

SEQ ID NOS: 1-9 show primer sequences used for gene insertion of Cas9 into pPCKRS and gRNA constructs.

SEQ ID NOS: 10-19 show primer sequences used for generating Lys to Ala Cas9 mutants.

SEQ ID NOS: 20-29 show primer sequences used for generating Lys to TAG Cas9 mutants.

SEQ ID NOS: 30-33 show template and primer sequences used for synthetic gRNA transcription.

SEQ ID NOS: 34-37 show qRT-PCR primer sequences used.

SEQ ID NO: 38-39 show an exemplary Cas9 coding and amino acid sequence, respectively.

SEQ ID NOS: 40-41 show an exemplary deactivated Cas9 (dCas9) coding and amino acid sequence, respectively. The sequence includes a D10A and H840A substitutions.

SEQ ID NOS: 42-51 show primer sequences used for generating OABK encoding plasmids.

DETAILED DESCRIPTION

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. As used herein, the term "comprises" means "includes." Thus, "comprising a nucleic acid molecule" means "including a nucleic acid molecule" without excluding other elements. It is further to be understood that any and all base sizes given for nucleic acids are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. All references, including patent applications and patents, and sequences associated with the GenBank® Accession Numbers listed (as of Apr. 7, 2016) are herein incorporated by reference.

In order to facilitate review of the various embodiments of the disclosure, the following explanations of specific terms are provided:

I. TERMS

Administration: To provide or give a subject an agent, such as an activatable Cas9 protein or corresponding coding sequence disclosed herein, by any effective route. Exemplary routes of administration include, but are not limited to, injection (such as subcutaneous, intramuscular, intradermal, intraperitoneal, intratumoral, and intravenous), transdermal, intranasal, and inhalation routes.

Cas9: An RNA-guided RNA endonuclease enzyme that can cut DNA. Cas9 has two active cutting sites (HNH and RuvC), one for each strand of the double helix. An exemplary native Cas9 sequence is shown in SEQ ID NO: 39. Catalytically inactive (deactivated) Cas9 (dCas9) as also encompassed by this disclosure. In some examples, a dCas9 includes one or more of the following point mutations: D10A, H840A, N863A (e.g., based on numbering in SEQ ID NO: 39). An exemplary deactivated Cas9 sequence is shown in SEQ ID NO: 41.

Cas9 sequences are publicly available. For example, GenBank® Accession Nos. nucleotides 796693 . . . 800799 of CP012045.1 and nucleotides 1100046 . . . 1104152 of CP014139.1 disclose Cas9 nucleic acids, and GenBank® Accession Nos. NP_269215.1, AMA70685.1 and AKP81606.1 disclose Cas9 proteins. In some examples, the Cas9 is a deactivated form of Cas9 (dCas9), such as one that is nuclease deficient (e.g., those shown in GenBank® Accession Nos. AKA60242.1 and KR011748.1). In certain examples, Cas9 has at least 80% sequence identity, for example at least 85%, 90%, 95%, or 98% sequence identity to such sequences (such as SEQ ID NOS: 38, 39, 40 and 41), and retains the ability to be used in the disclosed methods (e.g., can be modified to include an activatable lysine).

Complementarity: The ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

CRISPRs (clustered regularly interspaced short palindromic repeats): DNA loci containing short repetitions of base sequences. Each repetition is followed by short segments of "spacer DNA" from previous exposures to a virus. CRISPRs are found in approximately 40% of sequenced bacteria genomes and 90% of sequenced archaea. CRISPRs are often associated with cas genes that code for proteins related to CRISPRs. The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to RNAi in eukaryotic organisms. The CRISPR/Cas system can be used for gene editing (adding, disrupting or changing the sequence of specific genes) and gene regulation. By delivering the Cas9 protein and appropriate guide RNAs into a cell, the organism's genome can be cut at any desired location.

Downregulated or knocked down: When used in reference to the expression of a molecule, such as a gene or a protein (e.g., a target gene, such as one associated with disease or development), refers to any process which results in a decrease in production of a gene product, but in some examples not complete elimination of the gene product or gene function. In one example, downregulation or knock down does not result in complete elimination of detectable expression or activity. A gene product can be RNA (such as mRNA, rRNA, tRNA, and structural RNA) or protein. Therefore, downregulation or knock down includes processes that decrease transcription of a gene or translation of mRNA and thus decrease the presence of proteins or nucleic acids. The disclosed CRISPR/Cas9 system, specifically the activatable Cas9s disclosed herein, can be used to downregulate any target of interest.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability.

Downregulation or knock down includes any detectable decrease in the production of a gene product. In certain examples, detectable target protein or nucleic acid expression in a cell (such as a cell expressing an activatable Cas9 protein disclosed herein) decreases by at least 20%, at least 30%, at least 40%, at least 50%, at least 60%, at least 70%, at least 75%, at least 80%, at least 90%, at least 95%, at least 96%, at least 97%, at least 98%, or at least 99% (such as a decrease of 40% to 90%, 40% to 80% or 50% to 95%) as compared to a control (such an amount of protein or nucleic acid expression detected in a corresponding normal cell or sample). In one example, a control is a relative amount of expression in a normal cell (e.g., a non-recombinant HSC cell).

Effective amount: The amount of an agent (such as the CRISPR/activatable Cas9 agents provided herein,) that is sufficient to effect beneficial or desired results.

A therapeutically effective amount may vary depending upon one or more of: the subject and disease condition being treated, the weight and age of the subject, the severity of the disease condition, the manner of administration and the like, which can readily be determined by one of ordinary skill in the art. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition. In one embodiment, an "effective amount" is an amount sufficient to reduce symptoms of a disease, for example by at least 10%, at least 20%, at least 50%, at least 70%, or at least 90% (as compared to no administration of the therapeutic agent).

The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The term also applies to a dose that will allow for expression of an activatable Cas9 herein, and that allows for modulation of a target gene.

Expression: The process by which the coded information of a nucleic acid molecule, such as a target nucleic acid molecule is converted into an operational, non-operational, or structural part of a cell, such as the synthesis of a protein (e.g., target protein). Expression of a gene can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

The expression of a nucleic acid molecule or protein can be altered relative to a normal (wild type) nucleic acid molecule or protein (such as in a normal non-recombinant cell). Alterations in gene expression, such as differential expression, include but are not limited to: (1) overexpression (e.g., upregulation); (2) underexpression (e.g., downregulation); or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or subdomain is removed or added; (4) expression of an increased amount of the protein compared to a control or standard amount (e.g., upregulation); (5) expression of a decreased amount of the protein compared to a control or standard amount (e.g., downregulation); (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard.

Controls or standards for comparison to a sample, for the determination of differential expression, include samples believed to be normal (in that they are not altered for the desired characteristic, for example a non-recombinant cell) as well as laboratory values, even though possibly arbitrarily set, keeping in mind that such values can vary from laboratory to laboratory. Laboratory standards and values may be set based on a known or determined population value and can be supplied in the format of a graph or table that permits comparison of measured, experimentally determined values.

Gene Editing: A type of genetic engineering in which a nucleic acid molecule, such as DNA, is inserted, deleted or replaced in the genome of an organism using engineered nucleases, which create site-specific double-strand breaks (DSBs) at desired locations in the genome. The induced double-strand breaks are repaired through nonhomologous end-joining (NHEJ) or homologous recombination (HR), resulting in targeted mutations or repairs. The CRISPR/Cas9 methods disclosed herein, such as those that use an activatable Cas9, can be used to edit the sequence of one or more target genes, such as one associated with cancer (e.g., CML, breast cancer, colon cancer), infectious disease (such as HIV, hepatitis, HPV, and West Nile virus), or neurodegenerative disorder (e.g., Huntington's disease or ALS). For example, gene editing can be used to treat a disease, or to make a disease more susceptible to a therapy. Gene editing can also be used to mutate a gene in a test organism, to examine the role of the gene in vivo.

Gene Silencing: A specific type of gene regulation, namely significantly reducing (e.g., a reduction of at least 90%, at least 95%, or at least 99%) or preventing expression of a gene. Can also be referred to as knocking out gene expression, when the gene is completely silenced. The CRISPR/Cas9 methods disclosed herein, such as those that use an activatable Cas9, can be used to silence expression of one or more target genes, such as one associated with cancer (e.g., CML, breast cancer, colon cancer), infectious disease (such as HIV, hepatitis, HPV, and West Nile virus), or neurodegenerative disorder (e.g., Huntington's disease or ALS).

Genomic insertion site: A site of the genome that is targeted for, or has undergone, insertion of an exogenous polynucleotide. The disclosed methods with include use of a disclosed activatable Cas9 protein, which can be used to target a gene for manipulation at a genomic insertion site.

Guide sequence: A polynucleotide sequence having sufficient complementarity with a target polynucleotide sequence to hybridize with the target sequence and direct sequence-specific binding of a Cas9 to the target sequence. In some examples, the guide sequence is RNA. In some examples, the guide sequence is DNA. The guide nucleic acid can include modified bases or chemical modifications (e.g., see Latorre et al., *Angewandte Chemie* 55:3548-50, 2016). In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about, or at least, about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In some embodiments, a guide sequence is 15-25 nucleotides (such as 18-22 or 18 nucleotides).

The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

Homology-directed repair (HDR): A mechanism to repair double stranded DNA lesions. The CRISPR/Cas9 methods disclosed herein, such as those that use an activatable Cas9, can be used for HDR of one or more target genes, for example during G2 and S phase of the cell cycle.

Increase or Decrease: A statistically significant positive or negative change, respectively, in quantity from a control value. An increase is a positive change, such as an increase at least 50%, at least 100%, at least 200%, at least 300%, at least 400% or at least 500% as compared to the control value. A decrease is a negative change, such as a decrease of at least 20%, at least 25%, at least 50%, at least 75%, at least 80%, at least 90%, at least 95%, at least 98%, at least 99%, or at least 100% decrease as compared to a control value. In some examples the decrease is less than 100%, such as a decrease of no more than 90%, no more than 95% or no more than 99%.

Isolated: An "isolated" biological component (such as an activatable Cas9 protein or nucleic acid, or cell containing such) has been substantially separated, produced apart from, or purified away from other biological components in the cell or tissue of an organism in which the component occurs, such as other cells, chromosomal and extrachromosomal DNA and RNA, and proteins. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins. Isolated activatable Cas9 protein or nucleic acid, or cells containing such, in some examples are at least 50% pure, such as at least 75%, at least 80%, at least 90%, at least 95%, at least 98%, or at least 100% pure.

Modulate: A change in the content of genomic DNA gene. Modulation can include, but is not limited to, gene activation (e.g., upregulation), gene repression (e.g., downregulation), gene deletion, polynucleotide insertion, and/or polynucleotide excision.

Non-homologous end-joining (NHEJ): A mechanism that repairs double stranded breaks in DNA. The CRISPR/Cas9 methods disclosed herein, such as those that use an activatable Cas9, can be used for NHEJ of one or more target genes.

Non-naturally occurring or engineered: Terms used herein as interchangeably and indicate the involvement of the hand of man. The terms, when referring to nucleic acid molecules or polypeptides indicate that the nucleic acid molecule or the polypeptide is at least substantially free from at least one other component with which they are naturally associated in nature and as found in nature. In addition, the terms can indicate that the nucleic acid molecules or polypeptides is one having a sequence not found in nature.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence (such as a coding sequence of an activatable Cas9) if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers useful in this invention are conventional. Remington's Pharmaceutical Sciences, by E. W. Martin, Mack Publishing Co., Easton, Pa., 15th Edition (1975), describes compositions and formulations suitable for pharmaceutical delivery of a an activatable Cas9 protein or nucleic acid molecule (or other molecules needed for gene editing using the CRISPR/Cas9 system with the disclosed activatable Cas9).

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide, peptide and protein: Refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

Promoter: An array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In one example, the promoter is a U6 promoter or a CMV promoter.

Recombinant or host cell: A cell that has been genetically altered, or is capable of being genetically altered by introduction of an exogenous polynucleotide, such as a recombinant plasmid or vector. Typically, a host cell is a cell in which a vector can be propagated and its DNA expressed. Such cells can be eukaryotic or prokaryotic. The term also includes any progeny of the subject host cell. It is understood that all progeny may not be identical to the parental cell since there may be mutations that occur during replication. However, such progeny are included when the term "host cell" is used.

Regulatory element: A phrase that includes promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990) which is hereby incorporated by reference in its entirety. Regulatory elements include those that direct constitutive expression of a nucleotide sequence in many types of host cells and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific.

In some embodiments, a vector provided herein includes one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (see, e.g., Boshart et al., Cell, 41:521-530, 1985), the SV40 promoter, the dihydrofolate reductase promoter, the .beta.-actin promoter, the phosphoglycerol kinase (PGK) promoter, and the EF1α promoter.

Also encompassed by the term "regulatory element" are enhancer elements, such as WPRE; CMV enhancers; the R-U5' segment in LTR of HTLV-I (Mol. Cell. Biol., Vol. 8(1):466-472, 1988); SV40 enhancer; and the intron sequence between exons 2 and 3 of rabbit β-globin (Proc. Natl. Acad. Sci. USA., 78(3):1527-31, 1981).

Sequence identity/similarity: The similarity between amino acid (or nucleotide) sequences is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Variants of protein and nucleic acid sequences known in the art and disclosed herein are typically characterized by possession of at least about 80%, at least 90%, at least 95%, at least 96%, at least 97%, at least 98% or at least 99% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or at least 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Thus, an activatable Cas9 protein can have at least 80%, at least 85%, at least 90%, at least 91%, at least 92%, at least 95%, at least 96%, at least 97%, at least 98% or at least 99% sequence identity to SEQ ID No. 39 or 41, and include at least one activatable lysine (for example at position K76, K163, K510, K742, K810, K848, K855, K866, or K974). Similarly, exemplary activatable Cas9 nucleic acid sequences in some examples have at least 70%, at least 80%, at least 85%, at least 90%, at least 92%, at least 95%, at least 98%, or at least 99% sequence identity to SEQ ID No. 38 or 40, and include at least one amber stop codon (or other stop codon or 4 base codon), into which an activatable lysine can be incorporated (for example at position K76, K163, K510, K742, K810, K848, K855, K866, or K974).

Subject: A vertebrate, such as a mammal, for example a human. Mammals include, but are not limited to, murines, simians, humans, farm animals, sport animals, and pets. In one embodiment, the subject is a non-human mammalian subject, such as a monkey or other non-human primate, mouse, rat, rabbit, pig, goat, sheep, dog, cat, horse, or cow. In some examples, the subject has a genetic disease that can be treated using gene editing methods provided herein. In some examples, the subject is a laboratory animal/organism, such as a zebrafish, *Xenopus, C. elegans, Drosophila*, mouse, rabbit, or rat. Tissues, cells and their progeny of a biological entity obtained in vivo or cultured in vitro are also encompassed.

Therapeutic agent: Refers to one or more molecules or compounds that confer some beneficial effect upon administration to a subject. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition.

Transduced, Transformed and Transfected: A virus or vector "transduces" a cell when it transfers nucleic acid molecules into a cell. A cell is "transformed" or "transfected" by a nucleic acid transduced into the cell when the nucleic acid becomes stably replicated by the cell, either by incorporation of the nucleic acid into the cellular genome, or by episomal replication.

These terms encompasses all techniques by which a nucleic acid molecule can be introduced into such a cell, including transfection with viral vectors, transformation with plasmid vectors, and introduction of naked DNA by electroporation, lipofection, particle gun acceleration and other methods in the art. In some example the method is a chemical method (e.g., calcium-phosphate transfection), physical method (e.g., electroporation, microinjection, particle bombardment), fusion (e.g., liposomes), receptor-mediated endocytosis (e.g., DNA-protein complexes, viral envelope/capsid-DNA complexes) and biological infection by viruses such as recombinant viruses (Wolff, J. A., ed, *Gene Therapeutics*, Birkhauser, Boston, USA, 1994). Methods for the introduction of nucleic acid molecules into cells are known (e.g., see U.S. Pat. No. 6,110,743). These methods can be used to transduce a cell with the disclosed agents to manipulate its genome.

Transgene: An exogenous gene.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, blood and other clinical tests, and the like. For prophylactic benefit, the disclosed compositions may be administered to a subject at risk of developing a particular disease, condition, or symptom, or to a subject reporting one or more of the physiological symptoms of a disease, even though the disease, condition, or symptom may not have yet been manifested.

Upregulated: When used in reference to the expression of a molecule, such as a gene or a protein (e.g., a target gene, such as one associated with disease or development), refers to any process which results in an increase in production of a gene product. A gene product can be RNA (such as mRNA, rRNA, tRNA, and structural RNA) or protein. Therefore, upregulation includes processes that increase transcription of a gene or translation of mRNA and thus increase the presence of proteins or nucleic acids. The disclosed CRISPR/Cas9 system, specifically the activatable Cas9s disclosed herein, can be used to upregulate any target of interest.

Examples of processes that increase transcription include those that increase transcription initiation rate, those that increase transcription elongation rate, those that increase processivity of transcription and those that decrease transcriptional repression. Gene upregulation can include increasing expression above an existing level. Examples of processes that increase translation include those that increase translational initiation, those that increase translational elongation and those that increase mRNA stability.

Upregulation includes any detectable increase in the production of a gene product. In certain examples, detectable target protein or nucleic acid expression in a cell (such as a cell expressing an activatable Cas9 protein disclosed herein) increases by at least 20%, at least 30%, at least 40%, at least 50%, at least 60%, at least 70%, at least 75%, at least 80%, at least 90%, at least 95%, at least 100%, at least 200%, at least 400%, or at least 500% as compared to a control (such an amount of protein or nucleic acid expression detected in a corresponding normal cell or sample). In one example, a control is a relative amount of expression in a normal cell (e.g., a non-recombinant cell).

Under conditions sufficient for: A phrase that is used to describe any environment that permits a desired activity. In one example the desired activity is expression of an activatable Cas9 disclosed herein, in combination with other necessary elements, for example to control special or temporal expression of a target gene.

Vector: A nucleic acid molecule into which a foreign nucleic acid molecule can be introduced without disrupting the ability of the vector to replicate and/or integrate in a host cell. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art.

A vector can include nucleic acid sequences that permit it to replicate in a host cell, such as an origin of replication. A vector can also include one or more selectable marker genes and other genetic elements known in the art. An integrating vector is capable of integrating itself into a host nucleic acid. An expression vector is a vector that contains the necessary regulatory sequences to allow transcription and translation of inserted gene or genes.

One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. In some embodiments, the vector is a lentivirus (such as 3rd generation integration-deficient lentiviral vectors) or adeno-associated viral (AAV) vectors, and Adeno-Associated viral (AAV) vectors.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

Certain vectors are capable of directing the expression of genes to which they are operatively-linked. Such vectors are referred to herein as "expression vectors." Common expression vectors of utility in recombinant DNA techniques are often in the form of plasmids. Recombinant expression vectors can comprise a nucleic acid provided herein (such as a guide RNA, nucleic acid encoding an activatable Cas9 protein) in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

II. OVERVIEW OF SEVERAL EMBODIMENTS

Clustered regularly interspaced short palindromic repeat (CRISPR) RNA-guided adaptive immune systems that protect bacteria and archaea from infection by viruses have been repurposed for genome engineering in a wide variety of cell types and multicellular organisms. CRISPRs are DNA loci containing short repetitions of base sequences. Each repetition is followed by short segments of spacer DNA from previous exposures to a virus. CRISPRs are often associated with Cas genes. By introducing plasmids containing a Cas gene and specifically constructed CRISPRs into eukaryotic cells, the eukaryotic genome can be cut at any desired position. The Cas9 nuclease for targeted genome editing can include fused nuclear localization signals (NLSs) to a codon-optimized version of the Cas9 gene. This Cas9 sequence can be co-expressed with plasmids expressing the tracrRNA and a crRNA-guide, or a single chimeric guide RNA (gRNA).

Provided herein is a genetically encoded light- or chemical-activated CRISPR/Cas9 system for conditional control of gene editing and gene expression. Through both alanine and unnatural amino acid scanning, lysine residues important for Cas9 function were identified. It is shown that the genetically encoded caged or protected Cas9 can be used for gene editing—for activation and deactivation—of both fluorescent reporters as well as an endogenous gene in human cells. The caged or protected enzyme was completely inactive before treatment with the activator (UV illumination, such as a 120 sec exposure to 365 nm light, or a phosphine). In contrast to other reported light-induced recruitment of a transcriptional activator to a DNA-bound, enzymatically inactive dCas9 (Nihongaki et al., *Chem Biol* 2015, 22 (2), 169-74; Polstein, et al., *Nat Chem Biol* 2015, 11 (3), 198-200), the disclosed approach allows for regulation of Cas9 function. Moreover, upon light-induced decaging or chemical-induced deprotection, wild-type Cas9 was generated.

Many cell types and model organisms can be modified by the disclosed Cas9-mediated gene editing methods, such as those provided in Sander et al. (*Nat Biotechnol* 2014, 32 (4), 347-55). Unnatural amino acid mutagenesis based on the pyrrolysine system is expanding into model organisms, such as *C. elegans* and *D. melanogaster* (Greiss et al., *J Am Chem Soc* 2011, 133 (36), 14196-9; Parrish et al., *ACS Chem Biol* 2012, 7 (7), 1292-302; Bianco et al., *Nat Chem Biol* 2012, 8 (9), 748-50). Thus, the disclosed methods can be used for chemical and optical control of CRISPR/Cas9 function in cell culture and in vivo. Optical or chemical control of CRISPR/Cas9 allows for the study of gene function with high precision, and can reduce toxicity from off-target mutations (Fu et al., *Nat Biotechnol* 2013, 31 (9), 822-6; Lin et al., *Nucleic Acids Res* 2014, 42 (11), 7473-85) by restricting the function of Cas9 to certain locations or time points.

Thus, provided herein are systems, methods, and compositions for manipulation of sequences and/or activities of target sequences that utilize the disclosed activatable Cas9 proteins. Provided are vectors and vector systems, some of which encode one or more components of a CRISPR complex, such as an activatable Cas9 and appropriate tRNA/aminoacyl-tRNA synthetase pair, as well as methods for the design and use of such vectors. Also provided are methods of directing CRISPR complex formation in cells and methods for selecting specific cells by introducing precise mutations utilizing the CRISPR/Cas9 system.

A. Activatable Cas9 Proteins

Provided here are novel, non-naturally occurring, Cas9 proteins that can be activated by light or other agents. The disclosure of Cas9 proteins that are catalytically inactive until activation by chemical or photochemical means allows for the use of such proteins in CRISPR/Cas9 systems to control gene expression at a temporal and/or spatial level. The Cas9 protein that is mutated to achieve an activatable Cas9 can be a native Cas9 sequence (such as SEQ ID NO: 39) or a deactivated Cas9 (dCas9) sequence (such as SEQ ID NO: 41).

Activatable Cas9 proteins are not biologically active until exposed to a particular activating agent, such as a light (e.g., UV light, visible light, near-IR light), or a particular chemical, such as phosphine or a phosphine derivative. For example, if the Cas9 protein includes one or more light activatable lysines (e.g., a photocaged lysine, PCK), the protein is inactive until the caging group is removed through light exposure (e.g., UV light). Similarly, if the Cas9 protein includes one or more chemically activatable lysines, such as an ortho-azidobenzyloxycarbonyl lysine (OABK), the protein is inactive until the chemically activatable lysine (e.g., OABK) is deprotected using an apporpiate agent (e.g., in the case of OABK, phosphine or a derivative thereof, such as one shown in FIG. 14).

In one example, the activatable Cas9 protein includes one or more photocaged lysines (PKC) as the light activatable group. Such proteins in some examples are activatable in the presence of UV light (such as exposure to light in the range of 10 to 400 nm, such as 100 nm to 400 nm, 280 to 400 nm, such as 365 nm). In some examples, the protein is exposed to UV light for at least 10 seconds, at least 30 seconds, at least 1 minute, at least 2 minutes, at least 3 minutes, at least 5 minutes, or at least 10 minutes. In some examples, the protein is exposed to at least 1 W of UV light, at least 2 W, at least 5 W, at least 10 W, at least 20 W, at least 25 W, at least 50 W, or at least 100 W of UV light.

Other light activatable lysines can be used, such as the coumarin lysine analogues disclosed in Luo et al. (*J. Am Chem Soc.* 136:15551-8, 2014). For example, 1 and 2 below, can be activated by light at UV or near-IR wavelengths, respectively.

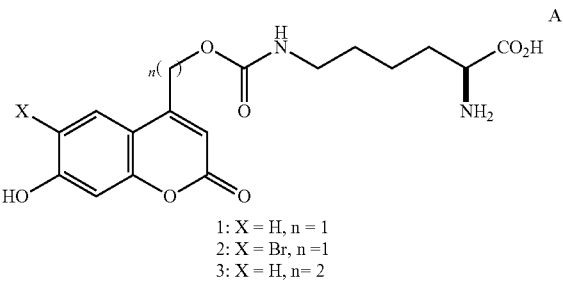

1: X = H, n = 1
2: X = Br, n = 1
3: X = H, n = 2

Other exemplary light activatable lysines that can be used are shown below, which are activatable at or above 405 nm.

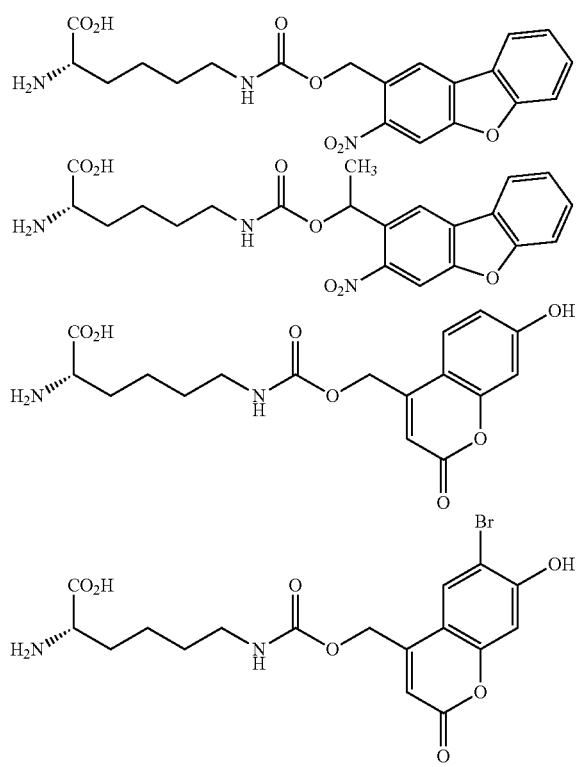

In one example, the activatable Cas9 protein includes one or more chemically activatable lysines, such as ortho-azidobenzyloxycarbonyl lysine (OABK), or any of the chemically activatable lysines shown below.

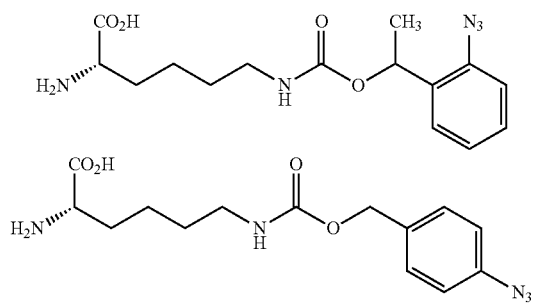

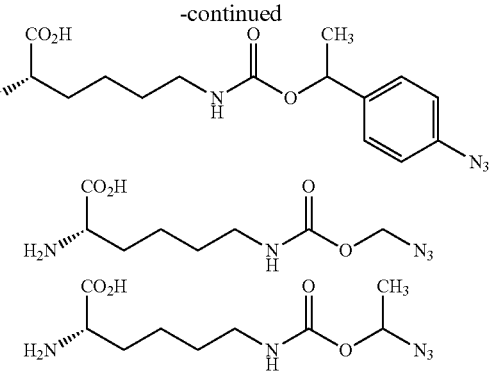

Figure 14:
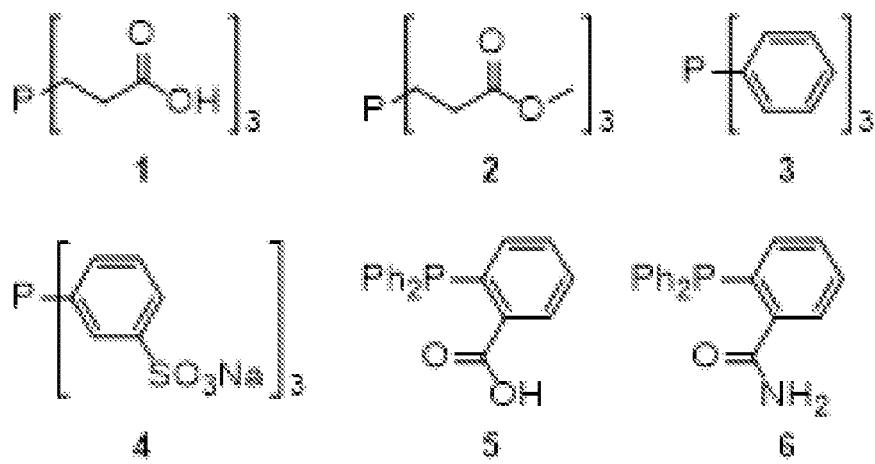
FIG. 14 shows structures of six phosphine derivatives TCEP (1), TCEP ester (2), TPP (3), TPPTS (4), 2DPBA (5), and 2DPBM (6).
Figures 16A, 16B, 16C, 16D, 16E, 16F, 16G, 16H:
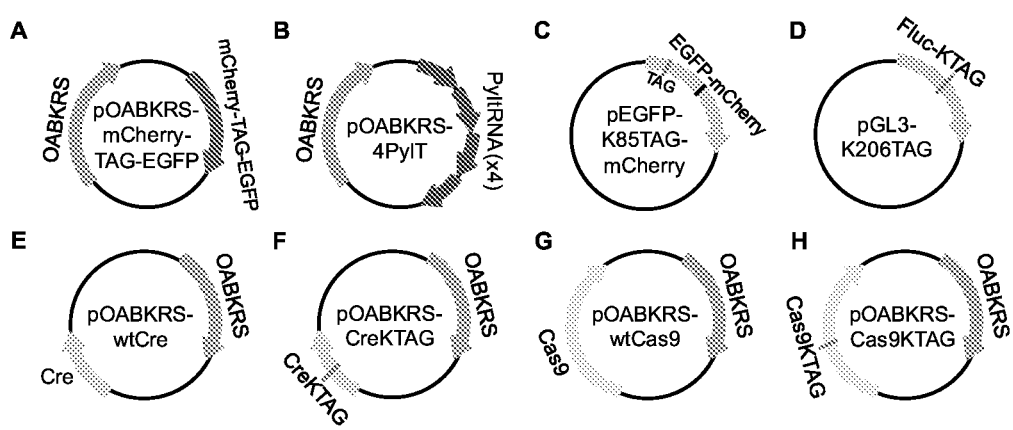
FIGS. 16A-16H are schematic drawings of plasmids used in the studies herein.

Cas9 proteins containing such agents are activatable in the presence of a chemical, such as phosphine or a phosphine derivative. Exemplary phosphines are shown in FIG. 14, such as 2DPBA or 2DPBM. In some examples, the OABK-Cas9 protein is exposed to a phosphine for at least 30 minute, at least 1 hour, at least 2 hours, at least 3 hours, at least 4 hours, at least 12 hours, or at least 24 hours. Small molecule-activation of Cas9 can be employed in cases where optical stimulation is not feasible, such as opaque, thick, or structurally complex specimens (most metazoans) and in systems that are not amenable to stimulation through irradiation, e.g., due to conflicting fluorescent reporters or UV toxicity. Moreover, bulk activation of large numbers of cells can be readily achieved, and, sequential activation of cellular processes is possible by using both light and small molecules as triggers (e.g., using the PCK-Cas9 and OABK-Cas9 proteins provided herein), such as the engineering of dual-input mammalian genetic circuits.

Other chemically activatable lysines can be used, such as those disclosed in Li et al. (*Nat Chem Biol* 10, 1003-1005, 2014 and Nat Chem 6, 352-361, 2014, both herein incorporated by reference). Other chemically activatable lysines can be incorporated into a Cas9 protein using the appropriate tRNA/tRNA synthtetase pair (e.g., pyrrolysyl-tRNA synthetase system). The resulting activatable Cas9 (such as one containing a propargyl carbamate group) is then exposed to the appropriate activating agent (such as palladium), thereby activating the Cas9 and allowing for gene manipulation using the methods provided herein.

Other light- or chemically-activatable lysines that can be used to generate an activatable Cas9 are shown in Table 1, along with the tRNA/tRNA synthetase that can be used to incorporate the mutant lysine into Cas9, and the agent that can be used to transform an inactive Cas9 into one that is active.

TABLE 1

| Exemplary light- and chemically-activatable lysines | | | |
|---|---|---|---|
| Lysine Structure | Pyrrolysine tRNA Synthetase Mutant | Activating/ Deprotecting Agent | References |
| (structure shown) | MbPylRS with the following mutations: M241F, A267S, Y271C, and L274M | light of ≤365 nm | Hemphill et al., Am Chem Soc. 2015, 137(17):5642-5. |

TABLE 1-continued

Exemplary light- and chemically-activatable lysines

| Lysine Structure | Pyrrolysine tRNA Synthetase Mutant | Activating/ Deprotecting Agent | References |
|---|---|---|---|
| (coumarin-OH carbamate lysine) | MbPylRS with the following mutations: Y271A and L274M | light of ≤405 nm | Luo et al., J Am Chem Soc. 2014, 136(44):15551-8. |
| (6-bromo-7-hydroxycoumarin carbamate lysine) | | light of ≤405 nm; 760 nm | |
| (nitrodibenzofuran methyl carbamate lysine) | | light of <405 nm, 710 nm | |
| (nitrodibenzofuran ethyl carbamate lysine) | | | |
| (2-azidobenzyl carbamate lysine) | MbPylRS with the following mutations: Y271A and Y349F | small molecules shown in FIG. 14 and similar phosphines; also trans-cyclooctene derivatives | |
| (1-(2-azidophenyl)ethyl carbamate lysine) | | | |
| (4-azidobenzyl carbamate lysine) | | | |
| (1-(4-azidophenyl)ethyl carbamate lysine) | | | |

TABLE 1-continued

Exemplary light- and chemically-activatable lysines

| Lysine Structure | Pyrrolysine tRNA Synthetase Mutant | Activating/ Deprotecting Agent | References |
|---|---|---|---|
| (structure: lysine with carbamate-O-CH2-N3) | wild-type MbPylRS | | |
| (structure: lysine with carbamate-O-CH(CH3)-N3) | | | |
| (structure: lysine with carbamate-O-cyclooctenyl) | MmPylRS with the following mutations: Y306A and Y384F  MbPylRS with the following mutations: Y271A and Y349F | (dimethyl-tetrazine) and other tetrazines | Li et al., Nat Chem Boil. 2014, 10(12):1003-5. |
| (structure: lysine with carbamate-O-allyl) | wild-type MbPylRS | allyl2Ph2Cl2 or other palladium complexes | Li et al., Nat Chem. 2014 Apr; 6(4):352-61. |
| (structure: lysine with carbamate-O-propargyl) | | | |

Any lysine in the Cas9 protein, such as any lysine in SEQ ID NO: 39 or 41, can be modified to be light or chemically activatable. In one example, one or more of K76, K163, K510, K742, K810, K848, K855, K866, and K974 (e.g., based on the numbering in SEQ ID NO: 39 or 41) is modified to be light or chemically activatable. In some examples, K163, K866, and or both K163 and K866, are modified to be light or chemically activatable. Thus, the disclosure provides Cas9 proteins with a light activatable at amino acid position 163 or 866 or comprises a chemically activatable lysine at amino acid position 163 or 866 (e.g., wherein the numbering refers to a full-length Cas9, such as SEQ ID NO: 39 or 41). The disclosure also provides Cas9 proteins with a light activatable lysine at amino acid position 810, 848, 855, or 974, or comprises a chemically activatable lysine at amino acid position 810, 848, 855, or 974 (e.g., wherein the numbering refers to a full-length Cas9, such as SEQ ID NO: 39 or 41).

In some examples, the activatable Cas9 protein comprises at least 80%, at least 85%, at least 90%, at least 92%, at least 95%, at least 98%, or at least 99% sequence identity to SEQ ID NO: 39 or 41, and includes (1) a light activatable lysine (e.g., PKC) at amino acid position 163, 866 or both 163 and 866, (2) a chemically activatable lysine at amino acid position 163 or, 866 or both 163 and 866, or (3) includes both a light activatable lysine and a chemically activatable lysine at positions 163 and 866 (e.g., light activatable lysine at position 163 and a chemically activatable lysine at position 866, or vice versa). In some examples, the activatable Cas9 protein comprises at least 80%, at least 85%, at least 90%, at least 92%, at least 95%, at least 98%, or at least 99% sequence identity to SEQ ID NO: 39 or 41, and includes (1) a light activatable lysine (e.g., PKC)lysine at amino acid position 810, 848, 855, or 974 (2) a chemically activatable lysine at amino acid position 810, 848, 855, or 974 or (3) includes a light activatable lysine and a chemically activatable lysine at two or more of positions 810, 848, 855, or 974 (e.g., light activatable lysine at position 810and a chemically activatable lysine at position 855, or vice versa). In some examples, such a variant protein includes a D10A mutation, H840A mutation, N863A mutation, or combinations thereof (e.g., wherein the numbering refers to a full-length Cas9, such as SEQ ID NO: 39 or 41).

In some examples, the activatable Cas9 includes a purification tag, such as an HA-tag, His-tag (such as 6-His), Myc-tag, E-tag, S-tag, calmodulin tag, FLAG-tag, GST-tag, MBP-tag, and the like. Such tags are in some examples at the N- or C-terminal end of the activatable Cas9 protein.

In some examples, the activatable Cas9 is at least 900 aa in length, such as at least 1000 aa, at least 1100 aa, at least 1200 aa, at least 1300 aa, at least 1340 aa, at least 1350 aa, at least 1360 aa, at least 1368 aa, at least 1369 aa, or at least 1375 aa in length.

1. Variant Activatable Cas9 Sequences

Activatable Cas9 proteins, including variants of the sequences provided herein (such as SEQ ID NO: 39 or 41 with a light activatable or chemically activatable lysine, such as at K76, K163, K510, K742, K810, K848, K855, K866, and/or K974, such as K163, K866, or both K163 and K866) are encompassed within this disclosure. In some examples, activatable Cas9 proteins provided herein can contain one or more additional mutations, such as a single insertion, a single deletion, a single substitution, or combinations thereof. In some examples, the activatable Cas9 protein includes 1-20 insertions, 1-20 deletions, 1-20 substitutions, or any combination thereof (e.g., single insertion together with 1-19 substitutions), but retain the light activatable or chemically activatable lysine. In some examples, the disclosure provides a variant of any disclosed activatable Cas9 protein (such as SEQ ID NO: 39 or 41 with a light activatable or chemically activatable lysine, such as at K76, K163, K510, K742, K810, K848, K855, K866, and/or K974, such as K163, K866, or both K163 and K866) having 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid changes, but retain the light or chemically activatable lysine. In some examples, any disclosed activatable Cas9 protein (such as SEQ ID NO: 39 or 41, with a light activatable or chemically activatable lysine, such as at K76, K163, K510, K742, K810, K848, K855, K866, and/or K974, such as K163, K866, or both K163 and K866) further includes 1-8 amino acid insertions, 1-15 amino acid deletions, 1-10 amino acid substitutions, or any combination thereof (e.g., 1-15, 1-4, or 1-5 amino acid deletions together with 1-10, 1-5 or 1-7 amino acid substitutions), with the retained light activatable or chemically activatable lysine. In one example, such variant peptides are produced by manipulating the nucleotide sequence encoding a peptide using standard procedures such as site-directed mutagenesis or PCR. Such variants can also be chemically synthesized.

One type of modification or mutation includes the substitution of amino acids for amino acid residues having a similar biochemical property, that is, a conservative substitution (such as 1-4, 1-8, 1-10, or 1-20 conservative substitutions). Typically, conservative substitutions have little to no impact on the activity of a resulting peptide. For example, a conservative substitution is an amino acid substitution in an activatable Cas9 protein (such as SEQ ID NO: 39 or 41 with a light activatable or chemically activatable lysine, such as at K76, K163, K510, K742, K810, K848, K855, K866, and/or K974, such as K163, K866, or both K163 and K866) that does not substantially affect the ability of the activatable Cas9 protein to be used in the disclosed methods. An alanine scan can be used to identify which amino acid residues in an activatable Cas9 protein (such as SEQ ID NO: 39 or 41 with a light activatable or chemically activatable lysine, such as at K76, K163, K510, K742, K810, K848, K855, K866, and/or K974, such as K163, K866, or both K163 and K866), can tolerate an amino acid substitution. In one example, the ability of the variant activatable Cas9 protein (such as SEQ ID NO: 39 or 41 with a light activatable or chemically activatable lysine, such as at K76, K163, K510, K742, K810, K848, K855, K866, and/or K974, such as K163, K866, or both K163 and K866) to modify gene expression in a CRISPR/Cas9 system, is not altered by more than 25%, for example not more than 20%, for example not more than 10%, when an alanine, or other conservative amino acid, is substituted for 1-4, 1-8, 1-10, or 1-20 native amino acids. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

More substantial changes can be made by using substitutions that are less conservative, e.g., selecting residues that differ more significantly in their effect on maintaining: (a) the structure of the polypeptide backbone in the area of the substitution, for example, as a sheet or helical conformation; (b) the charge or hydrophobicity of the polypeptide at the target site; or (c) the bulk of the side chain. The substitutions that in general are expected to produce the greatest changes in polypeptide function are those in which: (a) a hydrophilic residue, e.g., serine or threonine, is substituted for (or by) a hydrophobic residue, e.g., leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain, e.g., glycine.

2. Generation of Activatable Cas9 Proteins

In one example, the activatable Cas9 protein is expressed in vitro, for example, in a prokaryotic cell (e.g., bacteria such as *Lactobacillus, Lactococcus, Bacillus* (such as *B. subtilis*), *Escherichia* (such as *E. coli*), *Salmonella typhimurium*, and *Clostridium*), archea cell, plant or plant cell, fungal cell (e.g., *Neurospora*), yeast cell (e.g., *Saccharomyces* or *Pichia* (such as *S. cerevisiae* or *P. pastoris*), *Kluyveromyces lactis*), insect cell (e.g., SF9 cells), or mammalian cells (e.g., 293 cells, or immortalized mammalian myeloid and lymphoid cell lines). Once expressed, the activatable Cas9 protein can be isolated and/or purified conventional means, such as preparative chromatography and immunological separations. In some examples, as tag on the activatable Cas9 protein permits isolation of the protein from a culture media. Exemplary procedures include ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity, such as 98 to 99% homogeneity, can be used in the methods provided herein. For example, a purified preparation of an activatable Cas9 protein can be used as an alternative to expressing the Cas9 protein from a nucleic acid molecule in the CRISPR/Cas9 system.

In some examples, such an activatable Cas9 protein is generated using a nucleic acid molecule encoding Cas9 with an amber stop codon (TAG) (or other stop codon or 4 base codon) at the desired lysine position. Although the term amber stop codon is be used herein, one skilled in the art will appreciate that other mutations can be used, such as opal codon, ochre codon, or a 4 base mutation. To encode an activatable lysine of interest, the activatable lysine-specific orthogonal tRNA/aminoacyl-tRNA synthetase pair and the desired activatable Cas9 coding sequence including the amber stop codon are coexpressed in the host cell. The nucleic acid molecule encoding the activatable Cas9 coding sequence including the amber stop codon (or other stop codon or 4 base codon) is expressed, along with a nucleic acid molecule expressing the appropriate activatable lysine-specific orthogonal tRNA/aminoacyl-tRNA synthetase pair (such as a pyrrolysyl tRNA (PylT) nucleic acid molecule and a tRNA synthetase nucleic acid molecule, see for example US20130005019A1 and Gautier et al., *J Am Chem Soc* 2010, 132:4086-8, both herein incorporated by reference) in the presence of a light activated lysine (e.g., PCK) or a chemically activatable lysine (such as OABK), such that the light- or chemical-activated lysine is incorporated into the activatable Cas9 protein at the amber stop codons (or other stop codon or 4 base codon). In some examples, the 1 tRNA/aminoacyl-tRNA synthetase pair (e.g., pyrrolysyl tRNA (PylT)/tRNA synthetase) pair is expressed from the same vector. In some examples, the tRNA/aminoacyl-tRNA synthetase pair is operably linked to a promoter, such as U6. In some examples, the tRNA/aminoacyl-tRNA synthetase pair are each expressed from a different vector, and each is expressed from a promoter. As the expression level of the orthogonal suppressor tRNA can be a limiting factor for amber suppression in mammalian cells, multiple copies of the tRNA (such as PylT) can be supplied to achieve efficient incorporation of the activatable lysine (e.g., see FIGS. 12A and 12C). For example, the nucleic acid molecules (activatable Cas9 coding sequence and tRNA/aminoacyl-tRNA synthetase pair) can be part of one or more vectors (such as a plasmid or viral vector), which are introduced into the cell in which the activatable Cas9 protein will be expressed. Expression of the activatable Cas9 coding sequence, and tRNA/aminoacyl-tRNA synthetase pair can be controlled from one or more promoters (such as CMV, H1, or U6). The cells are cultured in the presence of the light- or chemically-activatable lysine (such as OABK). For example, the PCK or chemically activatable lysine (such as OABK) can be introduced into the growth media.

In addition to recombinant methods, activatable Cas9 proteins disclosed herein can also be constructed in whole or in part using native chemical ligation and/or expressed protein ligation.

B. Nucleic Acids Encoding Activatable Cas9 Proteins

Nucleic acid molecules encoding an activatable Cas9 protein are encompassed by this disclosure. Nucleic acid molecules include DNA, cDNA and RNA sequences which encode an activatable Cas9 peptide. In some examples, the nucleic acid molecules encoding activatable Cas9 proteins include a nonsense codon, such as an amber stop codon (TAG) or other codon (such as opal codon TGA, ochre codon TAA, or a 4 base codon) at the lysine(s) modified in the activatable Cas9 protein. The modified lysine is then introduced into the activatable Cas9 protein during translation of the protein in the presence of the modified lysine (e.g., in the presence of PCK or OABK) and by using an orthogonal unnatural amino acid-specific tRNA/aminoacyl-tRNA synthetase (tRNA/aaRS) pair. Examples of such unnatural amino acid-specific tRNA/aminoacyl-tRNA synthetase (tRNA/aaRS) pairs include tyrosyl (Tyr) and leucyl (Leu) pairs from *Escherichia coli* and the pyrrolysyl (Pyl) pair from archaea such as *Methanosarcina barkeri* (Mb) and *M. mazei* (Mm) (e.g., see Chatterjee et al., PNAS 110:11803-8, 2013; Takimoto et al., *Acs Chem Biol* 6, 733-743, 2011; Hancock et al., *J Am Chem Soc* 132, 14819-14824, 2010; Plass et al., *Angew Chem Int Edit* 50, 3878-3881, 2011; Yanagisawa et al., *Chem Biol* 15, 1187-1197, 2008). In one example, the pyrrolysyl-tRNA synthetase mutant N346A/C348A is utilized (Wang et al., *J Am Chem Soc* 134, 2950-2953, 2012).

Provided are nucleic acid sequences that code for an activatable Cas9 protein having at least 60%, at least 70%, at least 75%, at least 80%, at least 90%, at least 92%, at least 95%, at least 96%, at least 97%, at least 99% or at least 99% sequence identity to SEQ ID NO: 39 or 41 with a light- or chemically-activatable lysine, such as at K76, K163, K510, K742, K810, K848, K855, K866, and/or K974, such as K163, K866, or both K163 and K866. Such nucleic acid sequences can be generated based on the amino acid sequences provided herein, and the genetic code. In one example, an activatable Cas9 nucleic acid sequence has at least 70%, at least 80%, at least 85%, at least 90%, at least 92%, at least 95%, at least 98%, or at least 99% sequence identity to SEQ ID NO: 38 or 40, and includes an amber stop codon (or other stop codon or 4 base codon) at the position coding for K76, K163, K510, K742, K810, K848, K855, K866, and/or K974, such as K163, K866, or both K163 and K866. In some examples, such an activatable Cas9 nucleic acid sequence encodes a D10A, H840A, and/or N863A mutation.

One of skill can readily construct a variety of clones containing functionally equivalent nucleic acids, such as nucleic acids which differ in sequence but which encode the same activatable Cas9 protein sequence. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (see, for example, Stryer, 1988, Biochemistry, $3^{rd}$ Edition, W.H. 5 Freeman and Co., NY).

Based on the genetic code, nucleic acid sequences coding for any activatable Cas9 sequence can be routinely generated. In some examples, such a sequence is optimized for expression in a host cell, such as a host cell used to express the activatable Cas9 protein. Codon preferences and codon usage tables for a particular species can be used to engineer isolated nucleic acid molecules encoding an activatable Cas9 (such as one encoding a protein having at least 90%, at least 92%, at least 95%, at least 96%, at least 97%, at least 98%, at least 99% or 100% sequence identity to SEQ ID NO: 39 or 41, wherein the nucleic acid includes an amber stop codon (or other stop codon or 4 base codon) at the position coding for K76, K163, K510, K742, K810, K848, K855, K866, and/or K974, such as K163, K866, or both K163 and K866) that take advantage of the codon usage preferences of that particular species. For example, the activatable Cas9 proteins disclosed herein can be designed to have codons that are preferentially used by a particular organism of interest.

A nucleic acid encoding an activatable Cas9 protein (such as one encoding a protein having at least 90%, at least 92%, at least 95%, at least 96%, at least 97%, at least 98%, at least 99% or 100% sequence identity to SEQ ID NO: 39 or 41, wherein the nucleic acid includes an amber stop codon (or other stop codon or 4 base codon) at the position coding for K76, K163, K510, K742, K810, K848, K855, K866, and/or K974, such as K163, K866, or both K163 and K866) can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). Many cloning and in vitro amplification methodologies are known to persons skilled in the art. In addition, nucleic acids encoding an activatable Cas9 protein (such as one encoding a protein having at least 90%, at least 92%, at least 95%, at least 96%, at least 97%, at least 98%, at least 99% or 100% sequence identity to SEQ ID NO: 39 or 41, wherein the nucleic acid includes an amber stop codon (or other stop codon or 4 base codon) at the position coding for K76, K163, K510, K742, K810, K848, K855, K866, and/or K974, such as K163, K866, or both K163 and K866) can be prepared by cloning techniques. Examples of appropriate cloning and sequencing techniques, and instructions sufficient to direct persons of skill through cloning are found in Sambrook et al. (ed.), Molecular Cloning: A Laboratory Manual 2nd ed., vol. 1-3, Cold Spring Harbor Laboratory Press, Cold Spring, Harbor, N.Y., 1989, and Ausubel et al., (1987) in "Current Protocols in Molecular Biology," John Wiley and Sons, New York, N.Y.

Nucleic acid sequences encoding an activatable Cas9 protein (such as one encoding a protein having at least 90%, at least 92%, at least 95%, at least 96%, at least 97%, at least 98%, at least 99% or 100% sequence identity to SEQ ID NO: 39 or 41, wherein the nucleic acid includes an amber stop codon (or other stop codon or 4 base codon) at the position coding for K76, K163, K510, K742, K810, K848, K855, K866, and/or K974, such as K163, K866, or both K163 and K866) can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

In one example, an activatable Cas9 protein (such as a protein having at least 90%, at least 92%, at least 95%, at least 96%, at least 97%, at least 98%, at least 99% or 100% sequence identity to SEQ ID NO: 39 or 41, wherein the nucleic acid includes an amber stop codon (or other stop codon or 4 base codon) at the position coding for K76, K163, K510, K742, K810, K848, K855, K866, and/or K974, such as K163, K866, or both K163 and K866) is prepared by inserting the cDNA which encodes the activatable Cas9 protein into a vector. The insertion can be made so that the activatable Cas9 protein is read in frame so that the protein is produced.

The activatable Cas9 nucleic acid coding sequence (such as one having at least 80%, at least 85%, at least 90%, at least 92%, at least 95%, at least 96%, at least 97%, at least 98%, at least 99% or 100% sequence identity to SEQ ID NO: 38 or 40, wherein the nucleic acid includes an amber stop codon (or other stop codon or 4 base codon) at the position coding for K76, K163, K510, K742, K810, K848, K855, K866, and/or K974, such as K163, K866, or both K163 and K866) can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect, plant and mammalian organisms. Methods of expressing DNA sequences having eukaryotic or viral sequences in prokaryotes are known. Biologically functional viral and plasmid DNA vectors capable of expression and replication in a host are known. The vector can encode a selectable marker, such as a thymidine kinase gene or antibiotic resistance gene.

Nucleic acid sequences encoding an activatable Cas9 protein (such as one encoding a protein having at least 90%, at least 92%, at least 95%, at least 96%, at least 97%, at least 98%, at least 99% or 100% sequence identity to SEQ ID NO: 39 or 41 and containing an amber stop codon (or other stop codon or 4 base codon) at the position coding for K76, K163, K510, K742, K810, K848, K855, K866, and/or K974, such as K163, K866, or both K163 and K866) can be operatively linked to expression control sequences. An expression control sequence operatively linked to an activatable Cas9 coding sequence is ligated such that expression of the activatable Cas9 protein coding sequence is achieved under conditions compatible with the expression control sequences. The expression control sequences include, but are not limited to appropriate promoters, enhancers, transcription terminators, a start codon (i.e., ATG) in front of an activatable Cas9 protein-encoding gene, splicing signal for introns, maintenance of the correct reading frame of that gene to permit proper translation of mRNA, and stop codons.

In one embodiment, vectors are used for expression in yeast such as *S. cerevisiae, P. pastoris*, or *Kluyveromyces lactis*. Exemplary promoters for use in yeast expression systems include but are not limited to: the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1.

Thus, in one example, after amplification in bacteria, plasmids can be introduced into the corresponding yeast auxotrophs by methods similar to bacterial transformation. The nucleic acid molecules encoding an activatable Cas9 protein (such as one encoding a protein having at least 90%, at least 92%, at least 95%, at least 96%, at least 97%, at least 98%, at least 99% or 100% sequence identity to SEQ ID NO: 39 or 41 and containing an amber stop codon (or other stop codon or 4 base codon) at the position coding for K76, K163, K510, K742, K810, K848, K855, K866, and/or K974, such as K163, K866, or both K163 and K866) can also be designed to express in insect cells.

An activatable Cas9 protein (such a protein having at least 90%, at least 92%, at least 95%, at least 96%, at least 97%, at least 98%, at least 99% or 100% sequence identity to SEQ ID NO: 39 or 41 and containing a modified lysine at K76, K163, K510, K742, K810, K848, K855, K866, and/or K974, such as K163, K866, or both K163 and K866) can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can be utilized. Proteins that are highly sensitive to proteolysis can be expressed in a yeast cell lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared that encode an activatable Cas9 protein (such as one encoding a protein having at least 90%, at least 92%, at least 95%, at least 96%, at least 97%, at least 98%, at least 99% or 100% sequence identity to SEQ ID NO: 39 or 41 and containing an amber stop codon (or other stop codon or 4 base codon) at the position coding for K76, K163, K510, K742, K810, K848, K855, K866, and/or K974, such as K163, K866, or both K163 and K866). Exemplary viral vectors include polyoma, SV40, adenovirus, vaccinia virus, adeno-associated virus, herpes viruses including HSV and EBV, Sindbis viruses, alphaviruses and retroviruses of avian, murine, and human origin. Baculovirus (*Autographa californica* multinuclear polyhedrosis virus; AcMNPV) vectors can be used and obtained from commercial sources. Other suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like. Pox viruses of use include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Other viral vectors that can be used include other DNA viruses such as herpes virus and adenoviruses, and RNA viruses such as retroviruses and polio.

Viral vectors that encode an activatable Cas9 protein (such as one encoding a protein having at least 90%, at least 92%, at least 95%, at least 96%, at least 97%, at least 98%, at least 99% or 100% sequence identity to SEQ ID NO: 39 or 41 and containing an amber stop codon (or other stop codon or 4 base codon) at the position coding for K76, K163, K510, K742, K810, K848, K855, K866, and/or K974, such as K163, K866, or both K163 and K866) can include at least one expression control element operationally linked to the nucleic acid sequence encoding the activatable Cas9 protein. The expression control elements are inserted in the vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. In one example the promoter is CMV or U6. Additional operational elements include, but are not limited to, leader sequence, termination codons, polyadenylation signals and any other sequences necessary for the appropriate transcription and subsequent translation of the nucleic acid sequence encoding the activatable Cas9 protein in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

Basic techniques for preparing recombinant DNA viruses containing a heterologous DNA sequence encoding the activatable Cas9 protein (such as one encoding a protein having at least 90%, at least 92%, at least 95%, at least 96%, at least 97%, at least 98%, at least 99% or 100% sequence identity to SEQ ID NO: 39 or 41 and containing an amber stop codon (or other stop codon or 4 base codon) at the position coding for K76, K163, K510, K742, K810, K848, K855, K866, and/or K974, such as K163, K866, or both K163 and K866) are known. Such techniques involve, for example, homologous recombination between the viral DNA sequences flanking the DNA sequence in a donor plasmid and homologous sequences present in the parental virus. The vector can be constructed for example by steps known in the art, such as by using a unique restriction endonuclease site that is naturally present or artificially inserted in the parental viral vector to insert the heterologous DNA.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding an activatable Cas9 protein (such as one encoding a protein having at least 90%, at least 92%, at least 95%, at least 96%, at least 97%, at least 98%, at least 99% or 100% sequence identity to SEQ ID NO: 39 or 41 and containing an amber stop codon (or other stop codon or 4 base codon) at the position coding for K76, K163, K510, K742, K810, K848, K855, K866, and/or K974, such as K163, K866, or both K163 and K866), and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982). One of skill in the art can readily use an expression systems such as plasmids and vectors of use in producing mutated FGF1 proteins in cells including higher eukaryotic cells such as the COS, CHO, HeLa and myeloma cell lines.

C. Recombinant Cells Expressing Activatable Cas9 Proteins

A nucleic acid molecule encoding an activatable Cas9 protein disclosed herein can be used to transform cells and make transformed (i.e., recombinant) cells. Thus, cells expressing an activatable Cas9 protein (such as a protein having at least 90%, at least 92%, at least 95%, at least 96%, at least 97%, at least 98%, at least 99% or 100% sequence identity to SEQ ID NO: 39 or 41 and containing an activatable lysine at K76, K163, K510, K742, K810, K848, K855, K866, and/or K974, such as K163, K866, or both K163 and K866) are disclosed. Cells expressing an activatable Cas9 protein disclosed herein can be eukaryotic or prokaryotic. Examples of such cells include, but are not limited to, bacteria, archea, plant, fungal, yeast, insect, and mammalian cells, such as *Lactobacillus, Lactococcus, Bacillus* (such as

*B. subtilis*), *Escherichia* (such as *E. coli*), *Clostridium, Saccharomyces* or *Pichia* (such as *S. cerevisiae* or *P. pastoris*), *Kluyveromyces lactis*, *Salmonella typhimurium, Drosophila cells, C. elegans* cells, *Xeonpus* cells, SF9 cells, C129 cells, 293 cells, *Neurospora*, and immortalized mammalian cell lines (e.g., Hela cells, myeloid cell lines, and lymphoid cell lines).

Cells expressing an activatable Cas9 protein (for example in the presence of an activatable lysine, such as PCK or OABK) are transformed or recombinant cells. Such cells can include at least one exogenous nucleic acid molecule that encodes an activatable Cas9 protein (such as a protein having at least 90%, at least 92%, at least 95%, at least 96%, at least 97%, at least 98%, at least 99% or 100% sequence identity to SEQ ID NO: 39 or 41 and containing an activatable lysine at K76, K163, K510, K742, K810, K848, K855, K866, and/or K974, such as K163, K866, or both K163 and K866). Such cells can further include at least one exogenous tRNA/aminoacyl-tRNA synthetase (RS) pair. It is understood that all progeny may not be identical to the parental cell since there may be mutations that occur during replication. Methods of stable transfer, meaning that the foreign DNA is continuously maintained in the host cell, are known in the art.

Transformation of a host cell with recombinant DNA may be carried out by conventional techniques as are well known. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although other cell lines may be used, such as cells designed to provide higher expression desirable glycosylation patterns, or other features. Techniques for the transformation of yeast cells, such as polyethylene glycol transformation, protoplast transformation and gene guns are also known.

D. Kits

Kits are provided that include one or more of the disclosed activatable Cas9 proteins, isolated nucleic acid molecules encoding an activatable Cas9 protein, vectors including such activatable Cas9 coding sequences, and recombinant cells including such nucleic acid molecules or vectors. In some examples, such components are in separate vials.

In some examples, the kit includes an activatable Cas9 protein, such as SEQ ID NO: 39 or 41 with a light- or chemically-activatable lysine (e.g., those shown in Table 1), such as at K76, K163, K510, K742, K810, K848, K855, K866, and/or K974, such as K163, K866, or both K163 and K866. In some examples, the activatable Cas9 protein includes a light-activatable (e.g., PCK) lysine at at least one of these lysines. In some examples, the chemically-activatable Cas9 protein includes OABK at at least one of these lysines. In some examples, the kit includes an activatable Cas9 protein with OABK at K76, K163, K510, K742, K810, K848, K855, K866, and/or K974, such as K163, K866, or both K163 and K866, and further includes (e.g., in a separate container) phosphine or phosphine derivative, such as tris (2-carboxyethyl)phosphine (TCEP), the TCEP methylester, triphenylphosphine, phosphanetriyltris(benzenesulfonic acid) trisodium salt (TPPTS), 2-(diphenylphosphino)benzoic acid (2DPBA), or 2-(diphenylphosphino)benzamide (2DPBM) (see FIG. 14).

In some examples, the kit includes a nucleic acid molecule encoding an activatable Cas9 protein, such as SEQ ID NO: 38 or 40 with an amber stop codon (or other stop codon or 4 base codon) at the position coding for K76, K163, K510, K742, K810, K848, K855, K866, and/or K974, such as K163, K866, or both K163 and K866. In some examples, the nucleic acid molecule encoding an activatable Cas9 protein is part of a vector, such as a plasmid or viral vector. In some examples, the nucleic acid molecule encoding an activatable Cas9 protein (which may be part of a vector) is present in a cell (such as a bacteria, yeast, or mammalian cell, such as *E. coli*). In some examples, the nucleic acid molecule encoding an activatable Cas9 protein includes an operably linked promoter, such as CMV or U6. In one example, activatable Cas9 protein includes PCK at one of these lysines. In some examples, the activatable Cas9 protein includes OABK at one of these lysines. In some examples, the kit that includes a nucleic acid molecule encoding an activatable Cas9 protein further includes a tRNA/aminoacyl-tRNA synthetase pair (such as a pyrrolysyl tRNA nucleic acid molecule and/or a tRNA synthetase nucleic acid molecule), for example as part of one or more vectors. In some examples, the kit that includes a nucleic acid molecule encoding an activatable Cas9 protein further includes PCK or OABK (for example in a separate container).

In some examples, the disclosed kits further include cell culture or growth media, such as media appropriate for growing bacterial, plant, insect, or mammalian cells. In some examples, such media includes an activatable lysine, such as OABK or PCK.

In some examples, the disclosed kits further include a guide nucleic acid molecule specific for a target nucleic acid molecule, such as a target whose temporal or spatial expression is desired to be controlled. The guide nucleic acid molecule can be part of a vector, such as a plasmid or viral vector.

E. CRISPR/Activatable Cas9 to Modulate Gene Expression

The disclosed activatable Cas9 proteins, and corresponding nucleic acid molecules (which include an appropriate tRNA/aminoacyl-tRNA synthetase pair, such as pyrrolysyl tRNA (PylT)/tRNA synthetase) can be used in a CRISPR/Cas9 system to modulate (e.g., increase or decrease) expression of one or more target genes. Such methods can be performed in vitro (such as in cell culture), or in vivo (such as in an organism, embryo, or mammal).

The CRISPR/Cas9 system which utilizes a disclosed activatable Cas9 protein can be used for gene editing in a cell, such as a prokaryotic or eukaryotic cell, such as a mammalian cell. In addition, the disclosed activatable Cas9 proteins and nucleic acid molecules can be used in combination with commercially available kits to design and develop vectors that include CRISPR/Cas9 genome editing materials for manipulating a specific target (e.g., those from Origene, Rockville, Md., from Addgene, Cambridge, Mass., such as the Church Lab CRISPR Plasmids, and from Life Technologies, Gaithersburg, Md., such as the GeneArt® CRISPR Nuclease Vector Kit).

The CRISPR/Cas9 system provided herein includes three general components: (1) an activatable Cas9 protein, whose expression can be driven by a promoter, such as CMV, (2) single guide nucleic acid molecule, such as RNA (sgRNA or gRNA), which is operably linked downstream of a target sequence and upstream of a promoter (such as the U6 promoter), and (3) an activation agent (such as light or a chemical), which activates the Cas9 protein. When introduced into cells (for example as part of a single vector or plasmid or divided into multiple vectors or plasmids), the guide nucleic acid molecule guides the activatable Cas9 to the locus and when activated with the activation agent, the activated Cas9 will cut the target site. Activated Cas9 unwinds the DNA duplex and cleaves one or both strands upon recognition of a target sequence by the guide nucleic acid molecule, but only if the correct protospacer-adjacent motif (PAM) is present at the 3' end. Non-homologous end joining (NHEJ) repair of this cut will result in small insertions and deletions (indels), so the technique can be used to knockout genes. If short, homologous DNA is also included in the transfection, the technique can also be used to insert this DNA into the cut site through HDR. Using this system, DNA sequences within the endogenous genome and their functional outputs are easily edited or modulated. As an alternative to expressing activatable Cas9 via appropriate nucleic acid molecules in the presence of modified lysine, the guide nucleic acid molecule and activatable Cas9 protein can also be delivered to the target cell in fixed amounts using encapsulation techniques.

1. Introduction of Activatable Cas9 Protein Directly into a Cell

In one example, the activatable Cas9 protein is expressed in a recombinant cell, such as *E. coli*, and purified, such as using the methods provided herein. In such examples, it is not necessary to express the tRNA/tRNA synthetase pair in the cells in which gene expression is being controlled, nor is it necessary to provide the modified/activatable lysine with the cells/organism in which gene expression is being controlled. The resulting purified activatable Cas9 protein, along with an appropriate guide nucleic acid molecule specific for the target gene, is then introduced into a cell or organism where gene expression can be regulated. In some examples, the activatable Cas9 protein and guide nucleic acid molecule are introduced as separate components into the target cell/organism. In other examples, the purified activatable Cas9 protein is charged with the guide nucleic acid (e.g., gRNA), and this complex is introduced into target cells (e.g., using transfection or injection). In some examples, the Cas9 protein and guide nucleic acid molecule are injected into an embryo (such as a zebrafish or *Xenopus* embryo).

Once the activatable Cas9 protein and guide nucleic acid molecule are in the cell, gene expression can be control spatially (e.g., in specific cells) or temporally (e.g., at a specific time in development), by exposing the cell or organism to the activating agent, such as light or a chemical. For example, if the activatable Cas9 protein includes a PCK, the cells/organism can be exposed to UV light, thereby activating the Cas9 protein an inducing the desired control of target gene expression. In another example, if the activatable Cas9 protein includes an OABK, the cells/organism can be exposed to phosphine or phosphine derivative (for example in the water or media in which they grow or in the food or water which they eat/drink), thereby activating the Cas9 protein an inducing the desired control of target gene expression.

2. Expression of Activatable Cas9 from Nucleic Acids

In one example, the activatable Cas9 protein is expressed from a nucleic acid molecule in a target cell containing a target gene whose expression is desired to be controlled. In such examples, it is necessary to express the tRNA/tRNA synthetase pair in the cells in which gene expression is being controlled, and to provide the modified/activatable lysine with the cells/organism in which gene expression is being controlled. Thus, the nucleic acid molecule encoding the activatable Cas9 includes an amber stop codon (or other stop codon or 4 base codon) at the desired lysine position to be caged/protected. This is co-expressed with the orthogonal tRNA/aminoacyl-tRNA synthetase (RS) pair (such as a pyrrolysyl tRNA (PylT) nucleic acid molecule and a tRNA synthetase nucleic acid molecule) in the host cell. The transformed cell or organism is exposed to a light-activatable lysine (e.g., PCK) or a chemically activatable lysine (e.g., OABK), such that the PCK or OABK gets incorporated into the activatable Cas9 protein at the amber stop codons (or other stop codon or 4 base codon) during translation of the protein. For example, the light-activated lysine (e.g., PCK) or a chemically activatable lysine (such as OABK) can be supplied in the growth media of the recombinant cell, in the food/drinking water of the organism, or injected into the cell/organism. This results in the production of the activatable Cas9 protein in the cell or organism. In addition, these nucleic acid molecules are co-expressed in the cell/organism with the guide nucleic acid molecule (e.g., gRNA) specific for the target whose expression is to be controlled.

In one example, multiple plasmids or vectors are used for the gene editing. The nucleic acid molecule encoding the activatable Cas9 and includes an amber stop codon (or other stop codon or 4 base codon) can be provided for example on one vector or plasmid, the tRNA/aminoacyl-tRNA synthetase pair on another vector or plasmid, and the guide nucleic acid molecule (e.g., gRNA) on yet another plasmid or vector. Multiple plasmids can be mixed and transfected into cells at the same time, for example using Lonza nucleofector technology for the simultaneous transfection of multiple plasmids at this time. But one skilled in the art will appreciate that other methods can be used to introduce these sequences, such as viral transduction using lentiviral, adeno-associated virus (AAV), retrovirus, adenovirus, or alphavirus technology.

In some examples, multiple nucleic acid molecules are expressed from a single vector or plasmid. For example, a single plasmid can include the tRNA/aminoacyl-tRNA synthetase pair. In addition, a single plasmid can include the nucleic acid molecule encoding the activatable Cas9 and includes an amber stop codon (or other stop codon or 4 base codon) and the guide nucleic acid molecule. In one example, a plasmid that encodes both a tRNA synthetase and the activatable Cas9 is utilized. In one example, a plasmid that encodes both the tRNA (e.g., multiple copies, such as at least 2, at least 3, at least 4 or at least 5 copies, such as 2, 3, 4, 5, or 6 copies) and guide nucleic acid molecule (e.g., gRNA) is utilized. In one example, a combination of plasmids is used, such as a first plasmid encoding for both tRNA synthetase and tRNA (e.g., multiple tRNA copies, such as at least 2, at least 3, at least 4 or at least 5 copies, such as 2, 3, 4, 5, or 6 copies), and a second plasmid encoding for activatable Cas9, guide nucleic acid molecule (e.g., gRNA) and tRNA (e.g., multiple copies of tRNA, such as at least 2, at least 3, at least 4 or at least 5 copies, such as 2, 3, 4, 5, or 6 copies).

In some examples a plurality of different guide nucleic acid molecules (e.g., gRNAs), one for each target (such as 1, 2, 3, 4, 5, or 10 different targets), are present on a single plasmid.

In some examples a plurality of tRNAs are expressed from a single plasmid.

The nucleic acid molecules expressed in the target cell can be under the control of a promoter (such as CMV, H1, or U6) and contain selection markers (such as antibiotic resistance).

In some examples, the protein and nucleic acid molecules are expressed by an embryo (such as a zebrafish or *Xenopus* embryo) by engineering the organism with a genetic code that has been expanded by the photocaged or protected lysine through expression of the engineered tRNA/tRNA synthetase pair either from injected plasmid DNA, injected mRNA, or stably integrated copies into the animal genome. The Cas9 protein containing a TAG codon can be expressed from injected plasmid DNA, injected mRNA, or stably integrated copies into the animal genome. The gRNA molecule can be directly injected or expressed from plasmid DNA or stably integrated copies into the animal genome.

The resulting recombinant cell, in the presence of PCK or a chemically activatable lysine (such as OABK), will express the activatable Cas9 protein, along with the guide nucleic acid molecule specific for the target gene. Once the activatable Cas9 protein is expressed, gene expression can be control spatially (e.g., in specific cells) or temporally (e.g., at a specific time in development), by exposing the cell or organism to the activating agent, such as light or a chemical. For example, if the activatable Cas9 protein includes a PCK, the cells/organism can be exposed to UV light, thereby activating the Cas9 protein an inducing the desired control of target gene expression. In another example, if the activatable Cas9 protein includes an OABK, the cells/organism can be exposed to phosphine or phosphine derivative (for example in the water in which they grow or in the food or water which they eat/drink), thereby activating the Cas9 protein an inducing the desired control of target gene expression.

3. Targets

One or more genes can be targeted by the disclosed methods, such as at least 1, at least 2, at least 3, at least 4 or at least 5 different genes in the organism, such as 1, 2, 3, 4, 5, 6, 7, 8, 9 or 10 different genes. In one example, the gene is associated with a disease, such as an inherited disease (e.g., cystic fibrosis, Huntington's disease, Tay-Sachs, and Duchenne muscular dystrophy). In one example, the gene is associated with cancer (e.g., a cancer of the lung, breast, colon, liver, pancreas, prostate, bone, brain, skin (e.g., melanoma), or kidney). In one example, the gene is involved in embryonic development (e.g., proto-oncogenes c-myc, and KiRas 2B, the proliferating cell nuclear antigen (PCNA), and p53). Examples of target genes include, but are not limited to those associated with cancer (e.g., BCR-ABL, Ras, Raf, p53, BRCA1, BRCA2, CXCR4, beta-catenin, HER2, and CDK4, as well as those in the COSMIC catalogue of somatic mutations in cancer).

In one example, three genes, oep, gol, and ntl are targeted in zebrafish embryos and activation with light or chemicals at 3, 6 and 10 hpf. The result sing phenotypes for gol, ntl, and oep silencing can be observed at 24-48 hpf. Surveyor/T7E1 and restriction fragment length polymorphism assays can be performed to quantify indel formation at the gol, ntl, and oep loci. The quantification of indels and pigmentation loss for acute gol inhibition will allow examination of titration of Cas9 activity through increasing illumination times.

III. EXAMPLES

Example 1

Materials and Methods

This example provides the materials and method for the results described in Examples 2 and 3.

Plasmid Constructs.

The CMV-driven Cas9 gene was PCR amplified from the hCas9 expression vector (Addgene 41815) (Mal et al., *Science* 2013, 339 (6121), 823-6) with primers shown in Table 2 to introduce both NheI and MfeI restriction sites as well as an HA tag on the C-terminus.

TABLE 2

Sequences of primers used for gene insertion of Cas9 into pPCKRS and gRNA constructs. Restriction sites bolded, HA tag underlined, and gRNAs in italics (guide target sequences capitalized).

| Strand | Sequence (5'→3') |
| --- | --- |
| hCas9-NheI Forward | TTAAGCTAGCACCATGGACAAGAAGT (SEQ ID NO: 1) |
| hCas9-HA-MfeI Reverse | CGGTGAATTCTTAAGCGTAATCTGGAACATCGTATGGGTAC ACCTTCCTCTTCTTC (SEQ ID NO: 2) |
| DsRed gRNA-4 | *TCGACTCTAGAGGATCCACgttttagagctagaaatagcaagttaaaataaggct agtccgttatcaacttgaaaaagtggcaccgagtcggtgctt* (SEQ ID NO: 3) |
| EGFP gRNA-7 | *TAGCTAGTCTAGGTCGATGCgttttagagctagaaatagcaagttaaaataagg ctagtccgttatcaacttgaaaaagtggcaccgagtcggtgctt* (SEQ ID NO: 4) |
| CD71 gRNA-2 5'UTR | *GGACGCGCTAGTGTGAGTGCgttttagagctagaaatagcaagttaaaataag gctagtccgttatcaacttgaaaaagtggcaccgagtcggtgctt* (SEQ ID NO: 5) |
| CD71 gRNA Exon 1 | *GTCATATACCCGGTTCAGCCgttttagagctagaaatagcaagttaaaataagg ctagtcgttatcaacttgaaaaagtggcaccgagtcggtgctt* (SEQ ID NO: 6) |
| CD71 gRNA Exon 2 | *CTGCAGCACGTCGCTTATATgttttagagctagaaatagcaagttaaaataagg ctagtcccgttatcaacttgaaaaagtggcaccgagtcggtgctt* (SEQ ID NO: 7) |
| CD71 gRNA Exon 4 | *GGGTTATGTGGCGTATAGTAgttttagagctagaaatagcaagttaaaataaggc tagtccgttatcaacttgaaaaagtggcaccgagtcggtgctt* (SEQ ID NO: 8) |

TABLE 2-continued

Sequences of primers used for gene insertion of Cas9 into pPCKRS and gRNA constructs. Restriction sites bolded, HA tag underlined, and gRNAs in italics (guide target sequences capitalized).

| Strand | Sequence (5'→3') |
|---|---|
| U6-promoter | tgtacaaaaaagcaggctttaaaggaaccaattcagtcgactggatccggtaccaaggtcgggc aggaagagggcctatttcccatgattccttcatatttgcatatacgatacaaggctgttagagagata attagaattaatttgactgtaaacacaaagatattagtacaaaatacgtgacgtagaaagtaataattt cttgggtagtttgcagttttaaaattatgttttaaaatggactatcatatgcttaccgtaacttgaaagta tttcgatttcttggctttatatatcttgtggaaaggacgaaacaccg (SEQ ID NO: 9) |

The ~4.9 kB Cas9 gene insert was digested, purified, and cloned between the NheI and MfeI restriction sites of the pPCKRS plasmid (Gautier et al., *J Am Chem Soc* 2010, 132:4086-8) with the Quick Ligation Kit (New England Biolabs). Alanine mutations and amber stop codons were introduced into Cas9 at five sites through site-directed mutagenesis with primers shown in Tables 2 & 3.

TABLE 3

Sequences of primers used in the development of K → Ala Cas9 mutants. Mutations introduced capitalized and bolded.

| Primer | Sequence (5'→3') |
|---|---|
| K76AlaForward | gcagaGCgaatcggatctgctacctgcaggagatc (SEQ ID NO: 10) |
| K76ala Reverse | cgattcGCtctgcgggtatatctgcgccgtgctgt (SEQ ID NO: 11) |
| K163Ala Forward | tatgatcGCatttcggggacacttcctcatcgagggg (SEQ ID NO: 12) |
| K163Ala Reverse | cccgaaatGCgatcatatgcgccagcgcgagatagat (SEQ ID NO: 13) |
| K510Ala Forward | cttcctGCacactctctgctgtacgagtacttcacagtttataacgagctcaccaa (SEQ ID NO: 14) |
| K510Ala Reverse | agagtgtGCaggaagcacctatcgttaggcagattttatcaaagttagtcatcc (SEQ ID NO: 15) |
| K742Ala Forward | accgttGCggtcgtggatgaactcgtcaaagtaa (SEQ ID NO: 16) |
| K742Ala Reverse | cgaccGCaacggtctgcagtattccctattgat (SEQ ID NO: 17) |
| K866Ala Forward | agagggGCgagtgataacgtcccctcagaag (SEQ ID NO: 18) |
| K866Ala Reverse | tcactcGCccctctattttatcggatcttgtcaacac (SEQ ID NO: 19) |

TABLE 4

Sequences of primers used in the development of K → TAG Cas9 mutants. Mutations introduced capitalized and bolded.

| Primer | Sequence (5'→3') |
|---|---|
| K76TAG Forward | cgcagaTagaatcggatctgctacctgcaggagatc (SEQ ID NO: 20) |
| K76TAG Reverse | ccgattctAtctgcgggtatatctgcgccgtgctgt (SEQ ID NO: 21) |
| K163TAG Forward | tatgatcTagtttcggggacacttcctcatcgagggg (SEQ ID NO: 22) |
| K163TAG Reverse | cccgaaaCtagatcatatgcgccagcgcgagatagat (SEQ ID NO: 23) |
| K510TAG Forward | cttcctTagcactctctgctgtacgagtacttcacagtttataacgagctcaccaa (SEQ ID NO: 24) |
| K510TAG Reverse | agagtgCtaaggaagcacctttcgttaggcagattttatcaaagttagtcatcc (SEQ ID NO: 25) |

TABLE 4-continued

Sequences of primers used in the development of K → TAG Cas9 mutants. Mutations introduced capitalized and bolded.

| Primer | Sequence (5'→3') |
|---|---|
| K742TAG Forward | accgttTaggtcgtggatgaactcgtcaaagtaa (SEQ ID NO: 26) |
| K742TAG Reverse | cgacctAaacggtctgcagtattcccttttgat (SEQ ID NO: 27) |
| K866TAG Forward | agagggTagagtgataacgtcccctcagaag (SEQ ID NO: 28) |
| K866TAG Reverse | tcactctAccctctatttttatcggatcttgtcaacac (SEQ ID NO: 29) |

Figure 12A:
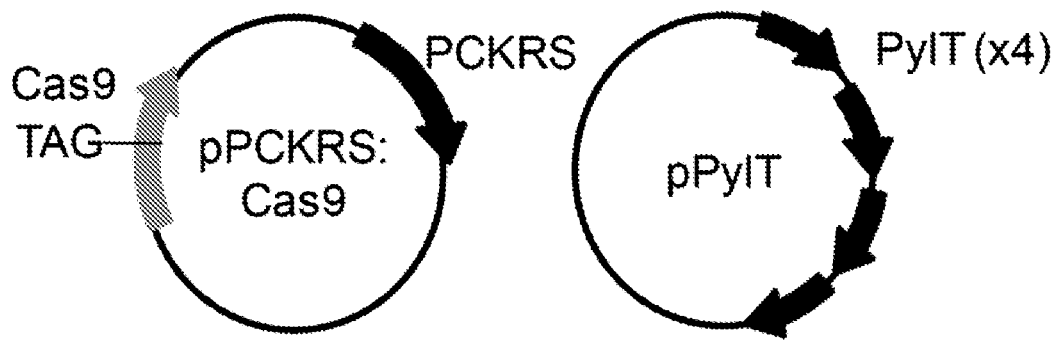
FIGS. 12A-12C are schematic drawings showing the plasmid constructs used for the expression of caged Cas9 (A) and analysis of activity with specific reporter genes (B). The CD71 gRNA construct is also shown (C).
Figure 12B:
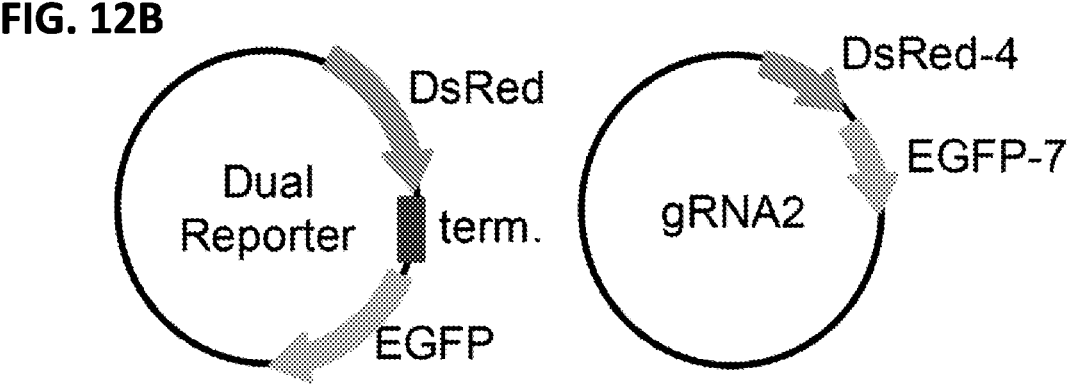
Figure 12C:
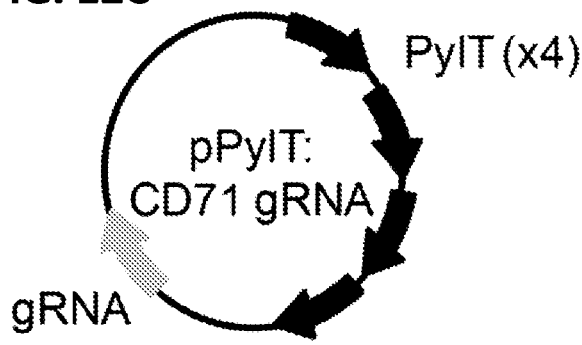

U6-promoted gRNAs targeting sequences upstream and downstream of the DsRed-terminator cassette, as shown in Table 2, were ordered as gBlock gene fragments (IDT). The gBlocks were PCR amplified to introduce SgrAI and AgeI restriction sites. Each amplified gBlock was individually cloned into a plasmid backbone using these restriction sites to generate the plasmids U6-gRNA-Upstream and U6-gRNA-Downstream. Following sequence validation, the U6-gRNA-Upstream cassette was PCR amplified to introduce flanking Nod restriction sites. The PCR product was digested and ligated into the plasmid U6-gRNA-Downstream plasmid. The resulting plasmid, gRNA2, contains both upstream and downstream U6-gRNA cassettes. The U6-promoted CD71 gRNAs, as shown in Table 2, was also ordered as gBlocks, PCR amplified with primers to introduce Bsu36I and PacI restriction sites, and then cloned between the Bsu36I and PacI restriction sites of the pPylT plasmid (Gautier et al., *J Am Chem Soc* 2010, 132 (12), 4086-8). Exon-based gRNA sequences were identified for target sites with minimal off-target effects. Plasmid feature maps are shown in FIGS. 12A-12C.

Mammalian Cell Expression of Alanine Mutants and Caged Cas9 Proteins.

HEK293T cells were seeded at ~100,000 cell per well into 6-well plates (BD Falcon) and incubated overnight in DMEM growth media supplemented with 10% FBS and 2% penicillin/streptomycin at 37° C. in 5% $CO_2$. Transfections were performed with 2 μg of each plasmid using 10 μL lipofectamine transfection reagent (Invitrogen) in 2 mL Opti-Mem media (Invitrogen) at 37° C. for 4 hours. After 4 hours the Opti-Mem transfection mixtures were removed from the cells and replaced with DMEM growth media supplemented with PCK (2 mM) for a 48 hour incubation.

Western Blots.

Total protein was extracted from ~1 million cells using 250 μL mammalian cell lysis buffer (Sigma-Aldrich) and size separated on a 10% SDS-PAGE gel, then transferred to a PVDF membrane. Standard western blot conditions were followed using a mouse-anti-HA primary antibody in addition to a mouse-anti-GADPH control (Santa Cruz Biotechnology). The primary antibodies were detected with a goat-anti-mouse-HRP fluorescent secondary antibody for chemiluminescent analysis with the VisiGlo kit (Amresco) and analyzed on a ChemiDoc imager (Bio-Rad).

Optical Activation of Reporter Gene Editing.

HEK293T cells were seeded at ~10,000 cell per well into 96-well plates (BD Falcon) and incubated overnight in DMEM growth media supplemented with 10% FBS and 2% penicillin/streptomycin at 37° C. in 5% $CO_2$. Transfections were performed with 200 ng of each plasmid using 2 μL branched polyethylenimine (bPEI, Sigma-Aldrich) in 200 μL Opti-Mem/DMEM media (Invitrogen) overnight at 37° C. following the standard protocol. The transfection mixtures were supplemented with PCK (2 mM) and removed after overnight incubations followed by exposure to 365 nm using a UV transilluminator (25 W). Fluorescent imaging of the dual reporter was performed after 48 hour incubations. Media was replaced with clear DMEM-high modified growth media (Thermo Scientific) for microscopy imaging on a Zeiss Observer Z1 microscope (10× objective, NA 0.8 plan-apochromat) with EGFP (38 HE; ex: BP470/40; em: BP525/50) and DsRed (43 HE; ex: BP550/25; em: BP605/70) filter cubes, then processed in Zen Pro 2011 imaging software. Fluorescent cell counting was performed in ImageJ software (NIH—settings: threshold 5-10%, size >200 pixels, and circularity 0-1). Error bars represent the standard deviations of three replicates. For the spatial control experiments, UV irradiations were performed through a tin foil mask to only expose a subset of cells to 365 nm light. Microscopy imaging was then performed on a Nikon A1 confocal microscope (20× objective) in a tiled grid and stitched using Elements software.

DNA Cleavage Assays.

HA-tag purification was performed on total protein lysate (see above) with 20 μL of mouse-anti-HA antibody (Santa Cruz Biotechnology) and 100 μL of Protein A Sepharose® 4B suspension (Life Technologies) overnight at 4° C. The sepharose beads were then washed three times with 300 μL PBS and resuspended to 100 μL total volume. Synthetic gRNAs were produced via PCR templates for in vitro T7RNAp transcription. The single stranded templates (Table 5) were PCR amplified and used in transcription reactions with the MEGAscript T7 transcription kit (Life Technologies) according to the manufacturer's protocol. The DNA cleavage assays were performed by incubating 40 μL of the Cas9 HA-purifications, 2 μL of synthetic gRNA purification (~6000 ng pre-annealed in TAE/Mg' buffer [0.04 M tris-acetate, 1 mM EDTA, and 12.5 mM magnesium acetate]), and 200 ng of the dual reporter plasmid in Cas9 activity buffer [20 mM HEPES, 150 mM KCl, 0.5 mM DTT, 0.1 mM EDTA, 10 mM $MgCl_2$, pH 7.4] (Jinek et al., *Science* 2012, 337 (6096), 816-21) overnight at 37° C. The DNA products were then heated to 72° C. for 20 min, loaded onto a 0.8% agarose gel, and stained with ethidium bromide.

TABLE 5

Sequences of templates and primers used for synthetic gRNA transcription. T7RNAp promoter sequence capitalized.

| Strand | SEQ ID NO: | Sequence (5'→3') |
|---|---|---|
| EGFP-7 gRNA template | 30 | TAATACGACTCACTATAGGGAGAtagct agtctaggtcgatgcgttttagagctagaaatagcaag ttaaaataaggctagtccgttatcaacttgaaaaagtg gcaccgagtcggtgctt |
| DsRed-4 gRNA template | 52 | TAATACGACTCACTATAGGGAGAtcgact ctagaggatccacgttttagagctagaaatagcaagtt aaaataaggctagtccgttatcaacttgaaaaagtgg caccgagtcggtgctt |
| T7 Forward | 32 | TAATACGACTCACTATAGGG |
| T7 Reverse | 33 | aaagcaccgactcggtgcca |

Photochemical Regulation of Endogenous CD71.

HeLa cells were seeded at ~10,000 cell per well into 96-well plates (BD Falcon) and incubated overnight in DMEM growth media supplemented with 10% FBS and 2% penicillin/streptomycin at 37° C. in 5% $CO_2$. Transfections were performed with 200 ng of each plasmid using 2 μL lipofectamine transfection reagent (Invitrogen) in 200 μL Opti-Mem media (Invitrogen) at 37° C. for 4 hours. After 4 hours the Opti-Mem transfection mixtures were removed from the cells and replaced with DMEM growth media supplemented with PCK (2 mM) for a 24 hour incubation. The PCK containing media was removed after the overnight incubation followed by exposure to 365 nm using a UV transilluminator (25 W). After a 48 hour incubation, both quantification of CD71 mRNA and fluorescent antibody detection of CD71 protein were performed. Quantification of CD71 mRNA was performed by qRT-PCR, in which total RNA was isolated from cells using the Trizol reagent (Invitrogen) and reverse transcribed with the iScript cDNA Synthesis kit (Bio-Rad). Quantitative RT-PCR was performed with the SsoFast Evagreen Supermix (Bio-Rad) using primer sets shown in Table 6. The threshold cycles (Ct) of each sample were normalized to the GAPDH control gene. Protein quantification was performed with anti-human CD71 APC fluorescent antibody (eBioscience) with 0.06 μg for 1 hr at 37° C., then analyzed on a Tecan M1000 plate reader (ex: 635/5; em: 660/10). Error bars represent the standard deviations of three replicates.

TABLE 6

Sequences of qRT-PCR primers used.

| Strand | SEQ ID NO: | Sequence (5'→3') |
|---|---|---|
| GAPDH Forward | 34 | TGCACCACCAACTGCTTAGC |
| GAPDH Reverse | 35 | GGCATGGACTGTGGTCATGAG |
| CD71 Forward | 36 | AAAATCCGGTGTAGGCACAG |
| CD71 Reverse | 37 | GCACTCCAACTGGCAAAGAT |

Example 2

Generation of Caged Cas9

Regulation of protein function with light provides control over biological processes with unprecedented resolution (Lee et al., ACS Chem Biol 2009, 4 (6), 409-27; Riggsbee et al., Trends Biotechnol 2010, 28 (9), 468-75; Baker et al., ACS Chem Biol 2014, 9 (7), 1398-407; Gautier, et al., Nat Chem Biol 2014, 10 (7), 533-41). To date, no optical control of Cas9 activity has been reported. Optically regulating Cas9 function enables precise spatial and temporal control of gene editing. Light-activated proteins can be generated in live mammalian cells with an expanded genetic code through the site-specific incorporation of caged amino acids in response to a recoded amber stop codon, TAG (Edwards et al., ACS Chem Biol 2009, 4 (6), 441-5; Groff et al., Chembiochem 2010, 11 (8), 1066-8; Gautier, A.; Deiters, A.; Chin, J. W., J Am Chem Soc 2011, 133 (7), 2124-7; Chou et al., Angew Chem Int Ed Engl 2011, 50 (30), 6839-42; Arbely et al., J Am Chem Soc 2012, 134 (29), 11912-5; Hemphill et al., J Am Chem Soc 2013, 135 (36), 13433-9; Uprety et al., Chembiochem 2014, 15 (12), 1793-9; Luo et al., J Am Chem Soc 2014, 136 (44), 15551-8).

Figure 1B:
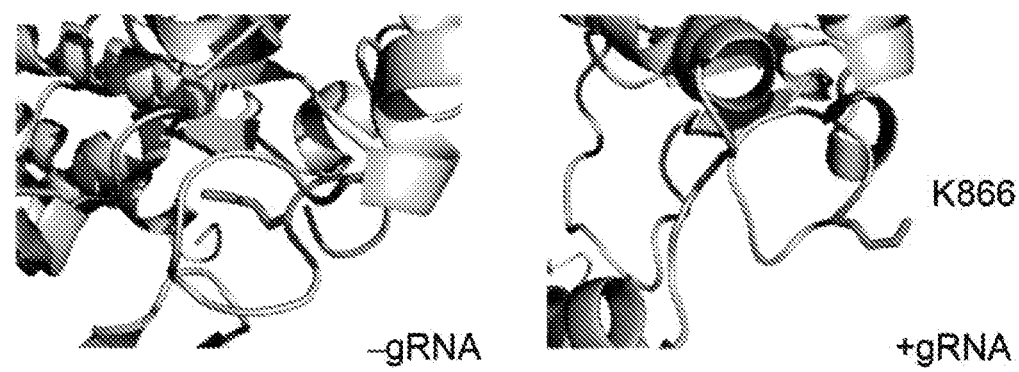

To develop a system for optochemical control of CRISPR/Cas9 gene editing (FIG. 1A), genetic code expansion was used by adding an engineered pyrrolysyl tRNA (PylT)/tRNA synthetase (PCKRS) pair to the translational machinery of human cells. Multiple lysines of interest were identified as potential caging sites for the inhibition of CRISPR/Cas9 function (FIGS. 2A-2D). K76, K163, K510, and K742 are highly conserved across species and, based on recent crystal structures (Nishimasu et al., Cell 2014, 156 (5), 935-49; Jinek et al., Science 2014, 343 (6176), 1247997), are in close proximity to the gRNA nucleic acid binding sites and thus may be essential for Cas9-gRNA interaction. K866 undergoes a significant conformational change upon binding of the gRNA, orienting the lysine to become surface exposed, which may be necessary to properly position the target DNA strand for cleavage (FIG. 1B). However, the exact role of this residue has not been determined.

Figure 1C:
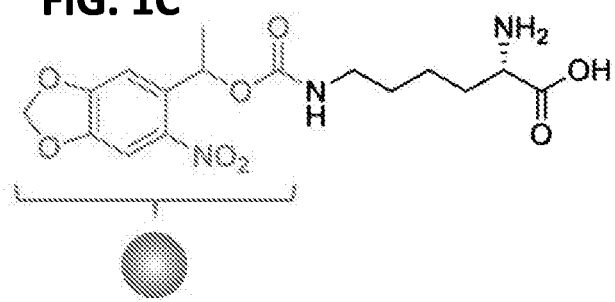
Figure 4A:
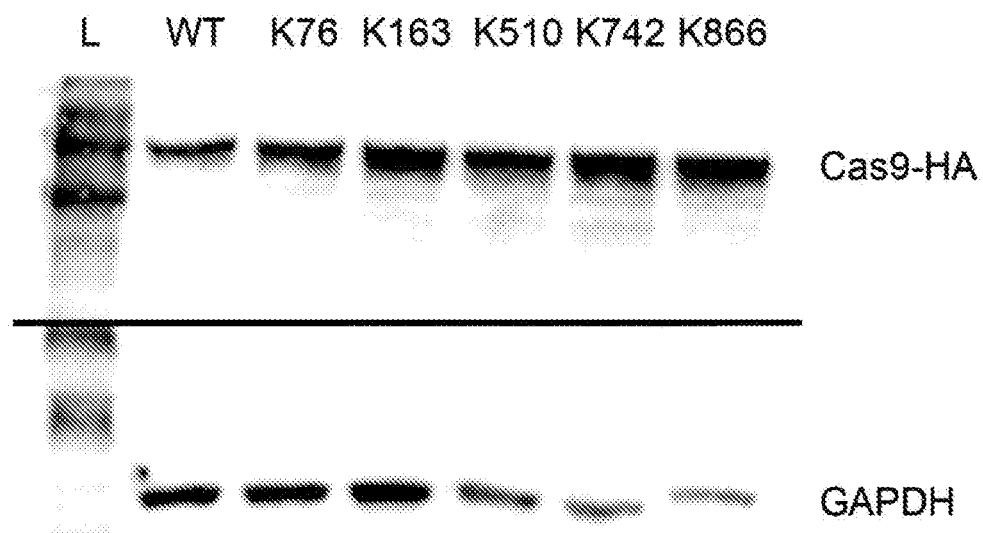
FIGS. 4A-4B are digital images of Western blot analysis. The Cas9 alanine mutant expression plasmids (A) and TAG mutant expression plasmids (B) were transfected and protein was purified for chemiluminescent detection of the C-terminal HA tag. The Cas9-HA and GAPDH control bands are annotated, and a horizontal line indicates a cut site on the transfer membrane for antibody staining.
Figure 5:
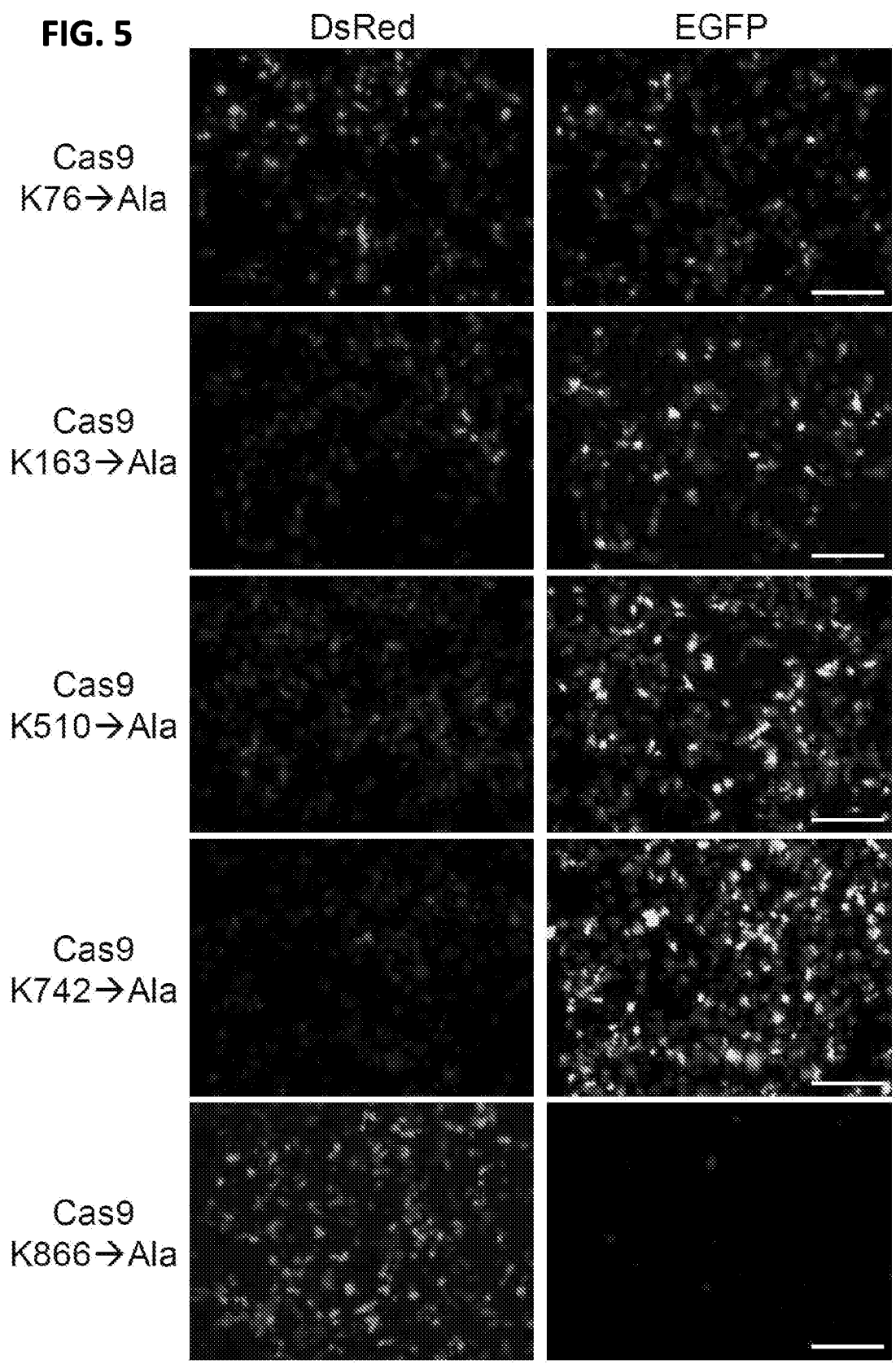
FIG. 5 is a digital image showing Cas9 alanine mutant activity scanning. The Cas9 K→A mutant expression plasmids were transfected into cells with the dual reporter system. Scale bars indicate 200 µm.

A dual reporter assay (based on pIRG, De Gasperi et al., Genesis 2008, 46 (6), 308-17), which switches from expressing DsRed to expressing EGFP in the presence of functional Cas9 and matching gRNAs, was developed (FIG. 3A). Two gRNAs (Table 1) were designed to target sequences upstream and downstream of the DsRed-terminator cassette. Upon co-expression of Cas9, these gRNAs direct the excision of DsRed, and the plasmid is repaired to allow EGFP expression. This assay was used in an initial alanine scan of K76, K163, K540, K742, and K866. All Cas9 alanine mutants expressed well in HEK293T cells (FIG. 4A) and four of the Cas9 alanine mutants were still active (FIG. 5). However, K866 was identified as being essential for activity, indicating it as a target for introduction of photocaged lysine (PCK, FIG. 1C) (Gautie et al., *J Am Chem Soc* 2010, 132 (12), 4086-8).

Figure 1D:
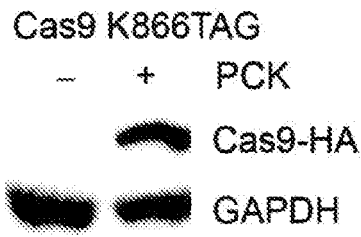
Figure 4B:
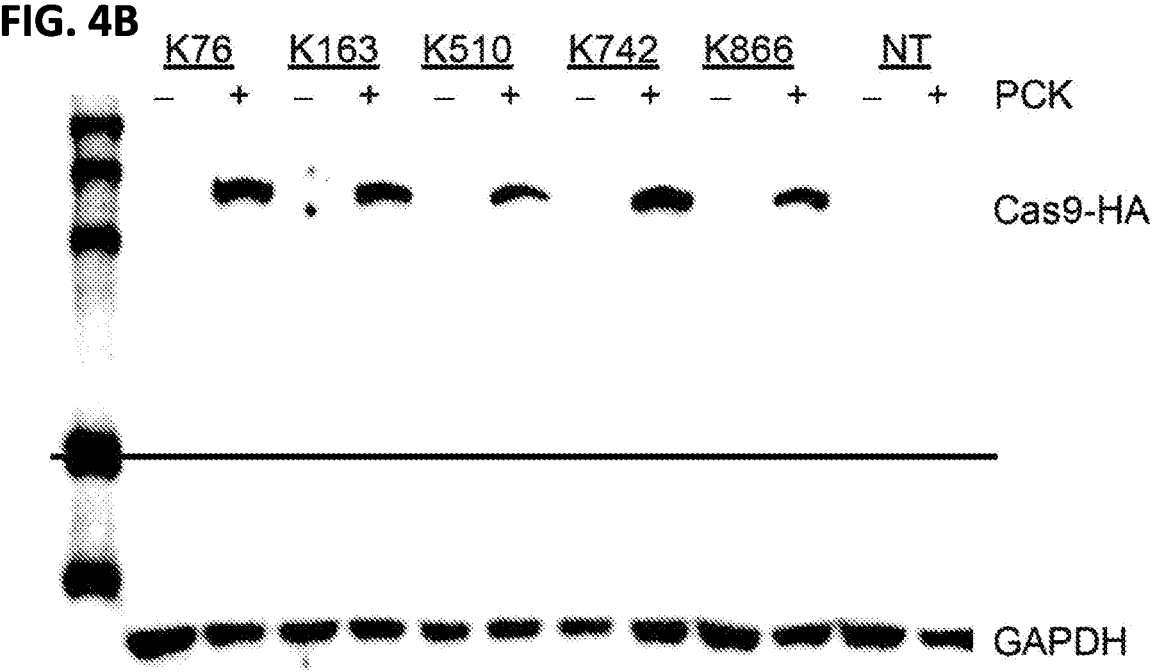
Figure 6:
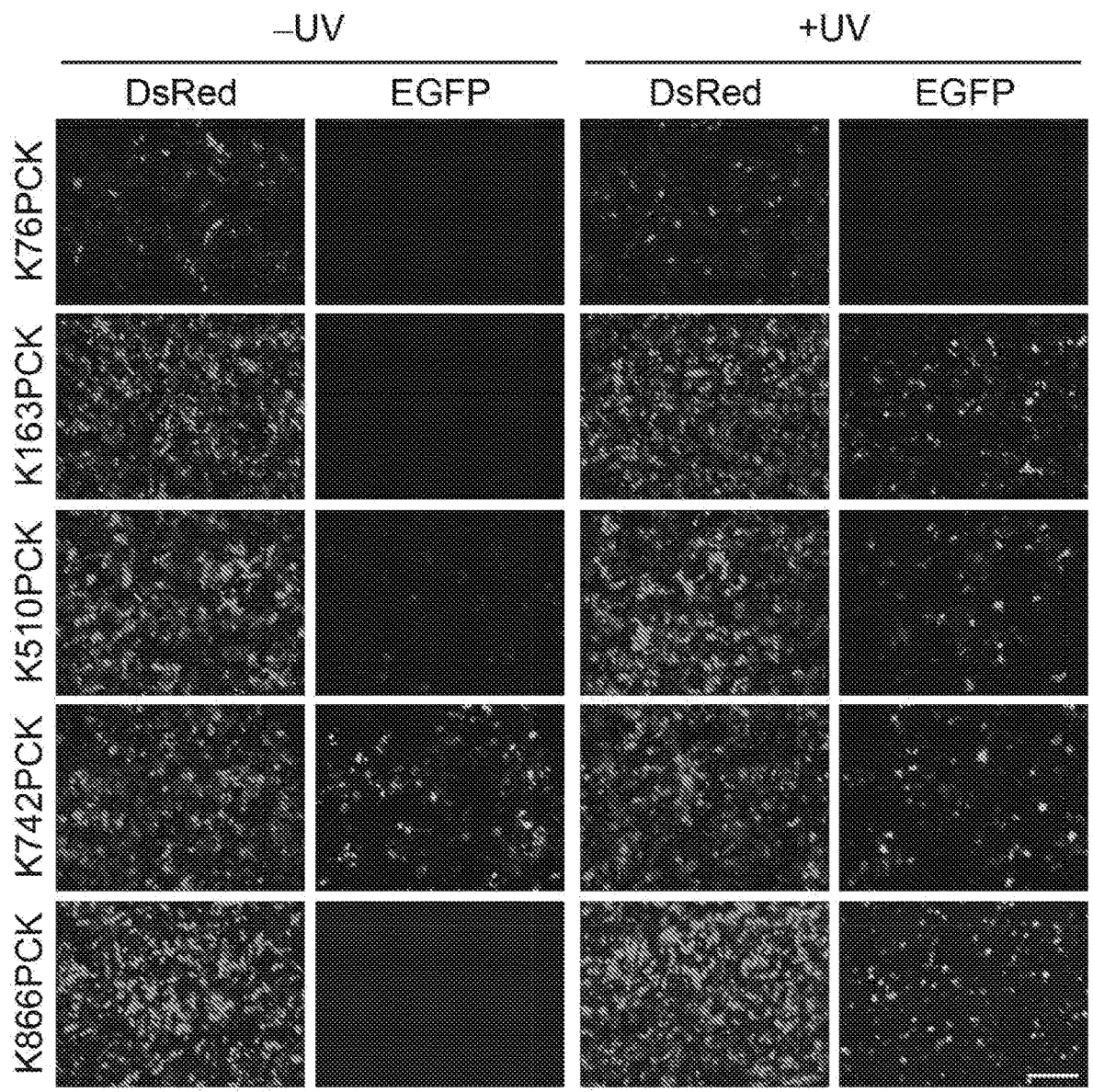
FIG. 6 is a digital image showing Cas9 PCK mutant activity scanning. HEK293T cells were transfected with the caged Cas9 expression system as well as the dual reporter construct and grown in the presence of PCK (2 mM) for 24 hours. The cells were kept in the dark or UV irradiated for 120 sec and imaged (10×) after 48 h. Scale bar indicates 200 µm.

Amber stop codon mutations were then introduced at all the five lysines of interest, since the PCK caging group may induce an additional level of perturbation compared to a K→A mutation, and Western blots confirmed PCK-dependent expression of the caged Cas9 mutants (FIG. 1D and FIG. 4B). The function of the caged Cas9 mutants in the presence and absence of UV exposure (365 nm, 2 min) was tested using the dual reporter assay. As shown in FIG. 6, the incorporation of PCK at K76, K163, and K866 showed full inhibition of Cas9 activity in the absence of UV exposure, while the K742PCK mutant was still functional similar to wild-type. Additionally, the K510PCK mutant was slightly leaky, showing undesired background activity in the absence of UV exposure. After light-activation, the K163, K510, and K866-PCK mutants showed successful activation of Cas9 as observed through the expression of EGFP. The K76PCK mutant was not activated. In contrast to wild-type Cas9, all cells expressing light-activated Cas9 mutants still showed DsRed expression, since the caged Cas9 activation occurs 24 hours after transfection, while the wild-type Cas9 was immediately active once expressed. Thus, in the case of light-activated Cas9, DsRed protein that has already been expressed persists, with a half-life greater than 4 days (Verkhusha et al., *Biochemistry* 2003, 42 (26), 7879-84).

Figure 2A:
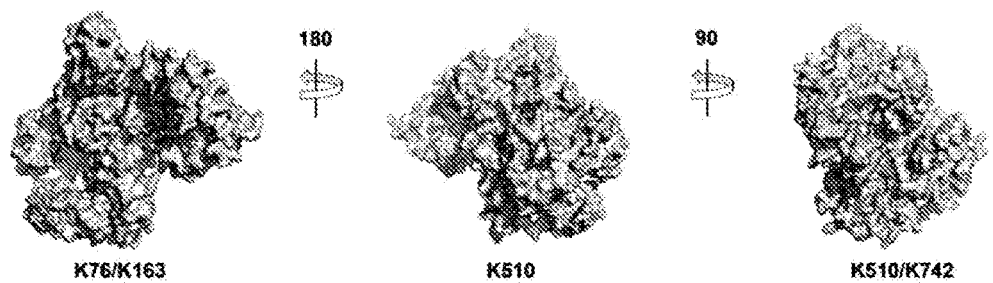
FIGS. 2A-2D show structural annotation of critical lysines on Cas9. A) Lysines of interest (red) depicted on a surface model of unbound Cas9 (PDB: 4CMP). B) Lysines of interest depicted on a surface model of bound Cas9 (PDB: 4OO8), with gRNA (yellow) and target DNA (blue) shown. K866 is only surface exposed in the gRNA-target bound Cas9 structure. C) Detailed view of each lysine of interest in the unbound Cas9 structure. D) Detailed view of each lysine of interest in the bound Cas9 structure. Note that K76, K163, K510, and K742 all appear poised to interact with the gRNA. K866 undergoes a significant conformational change upon binding of the gRNA, orienting the lysine to become surface exposed.
Figure 2B:
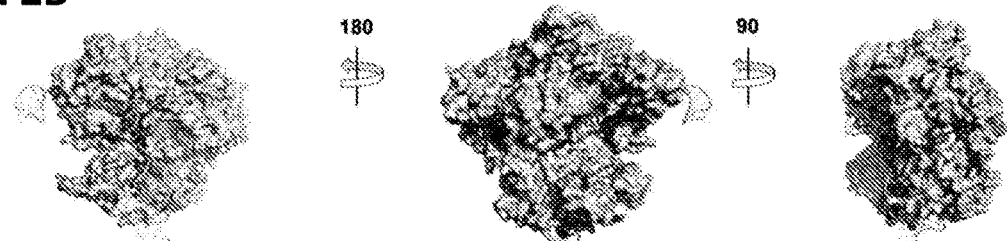
Figure 2C:
Figure 2D:
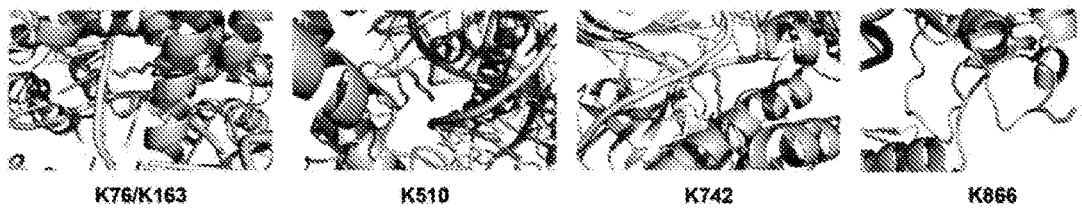
Figure 7A:
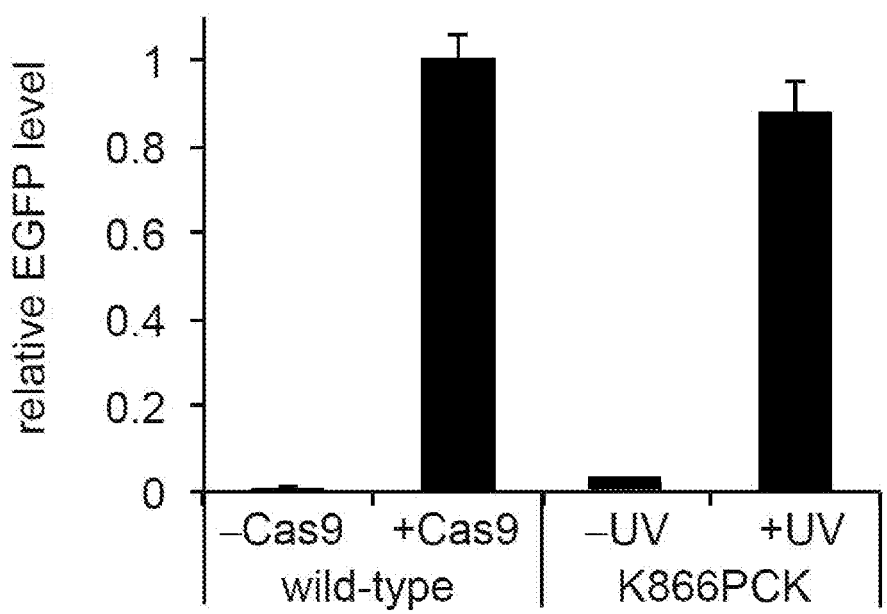
FIGS. 7A-7B. A) Analysis of EGFP expression by imaging cytometry. Error bars represent standard deviations from three replicates. B) Spatial control of CRISPR/Cas9 gene editing through irradiation of a subset of cells defined by a mask. Imaged at 20× magnification with tile stitching (2×3). Scale bar indicates 200 µm.

Thus, two lysine sites that are amenable to optically control of Cas9 function were identified, presenting two different pathways for the light-activation of CRISPR/Cas9 gene editing: 1) K163, which might interact with the gRNA; and 2) K866, which may play a role in positioning the non-target DNA strand (FIGS. 2C-2D). The Cas9 K866PCK mutant showed minimal background activity before irradiation, and high activity after light exposure for 2 minutes, reaching wild-type Cas9 levels (FIG. 7A). A UV irradiation time course was performed with the K866-caged Cas9 (FIGS. 8A-8B), demonstrating that exposure of >2 minutes did not further enhance activation.

Example 3

Spatial and Temporal Control of CRISPR/Cas9 Gene Editing Using Caged Cas9

Figure 7B:
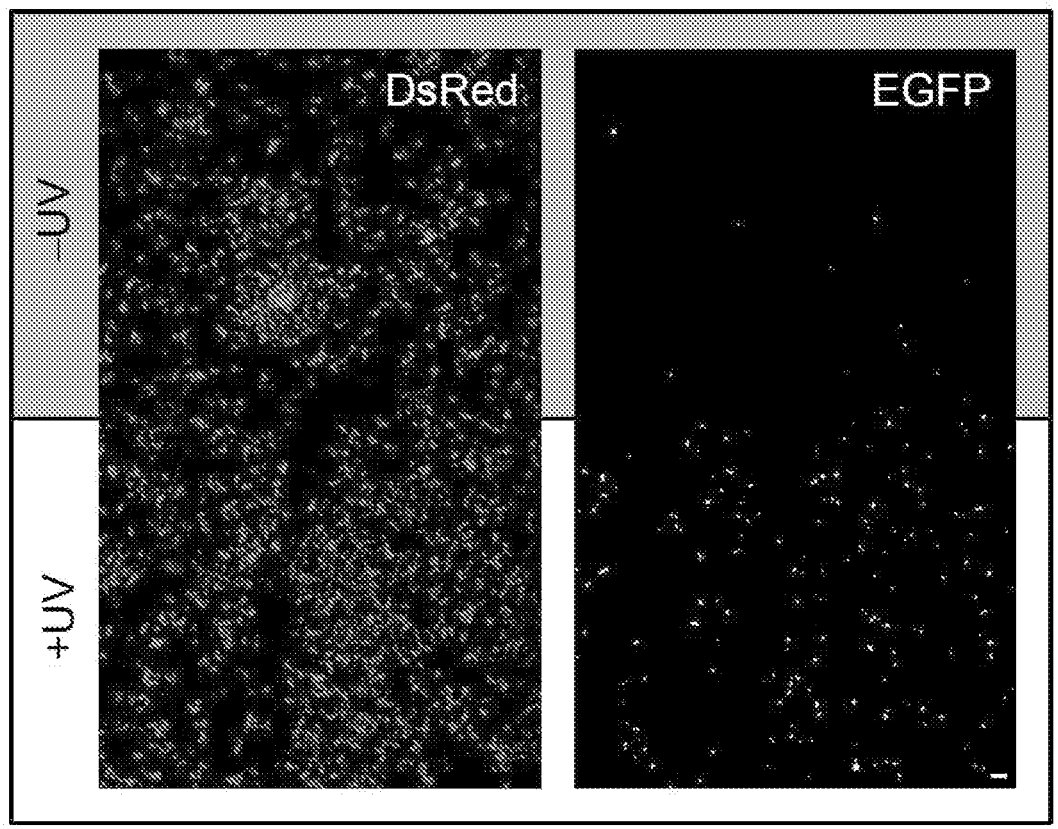

To show spatial control of CRISPR/Cas9 gene editing in mammalian cells, the activation of K866-caged Cas9 was performed through patterned UV irradiation of a layer of HEK293T cells (FIG. 7B). Further analysis of the mechanism of deactivation by the K163PCK and K866PCK mutations was performed through plasmid cleavage assays with purified Cas9 (FIG. 9), showing no DNA cleavage or nicking activity in the absence of UV irradiation. The absence of any catalytic activity of the caged enzyme suggests that interaction with the gRNA and/or target DNA may be inhibited through introduction of PCK, thereby deactivating Cas9 function. Taken together, these results successfully demonstrate spatial and temporal control of gene function using a site-specifically caged Cas9 that is genetically encoded in mammalian cells, allowing for conditional light-activation of CRISPR/Cas9 gene editing.

Silencing of an endogenous gene through light-activated gene editing using the optically activated Cas9 was demonstrated. The transmembrane transferrin receptor CD71 (also known as TfR1), associated with leukemia and lymphoma (Parenti et al., *Int J Endocrinol* 2014, 2014, 685396), was selected as a target. gRNAs for the 5'UTR and several exons with the coding region of CD71 were designed in order to inhibit protein expression via disruption of upstream regulatory elements and introduction of mutations, respectively.

Figures 10A, 10B:
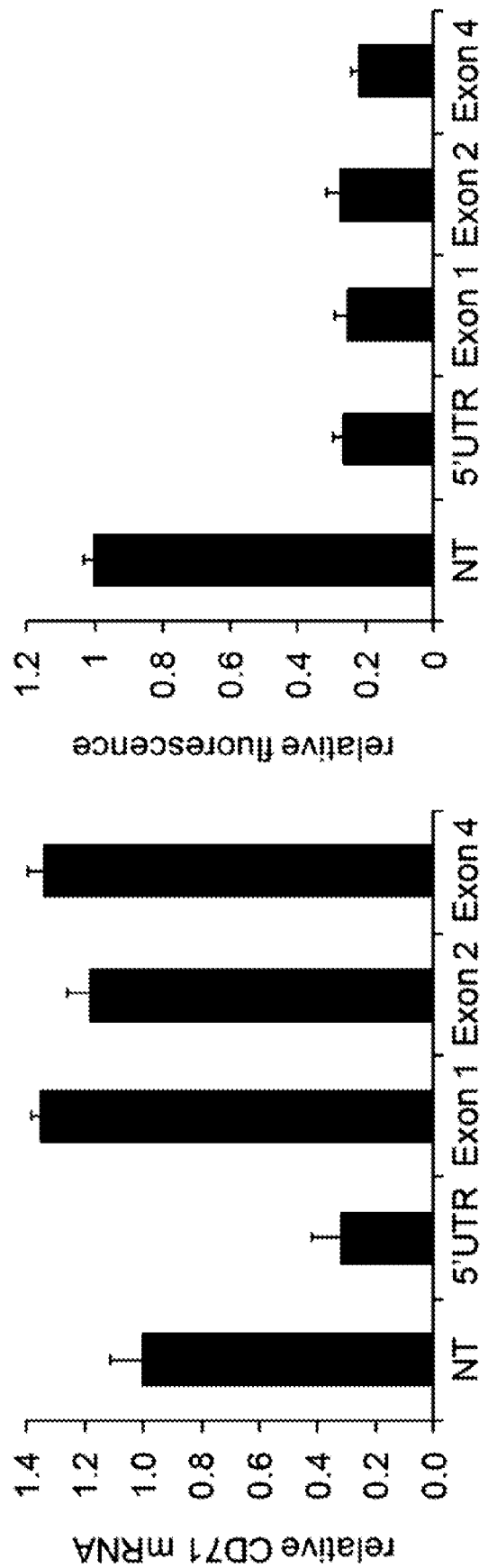
FIGS. 10A-10B are bar graphs showing wild-type Cas9 controls for the quantification of CD71. HeLa cells were transfected with the Cas9 and CD71 gRNA expression constructs, then incubated for 48 hours. Quantification of CD71 mRNA with qRT-PCR (A) and CD71 protein with fluorescent antibody detection (B) were performed. Error bars represent the standard deviations of three replicates.

First, it was confirmed that CD71 knockdown by wild-type CRISPR/Cas9 could be quantified via both qRT-PCR and phenotype analysis via fluorescent antibody staining of HeLa cells. Indeed, repression of CD71 mRNA with the 5'UTR targeting gRNA (~70%) was observed, while the exon-targeting gRNAs showed no effect on mRNA levels. In addition, reduced levels of CD71 protein (~75%) were observed for all gRNAs, relative to nontreated cells (FIGS. 10A-10B).

Figure 11A:
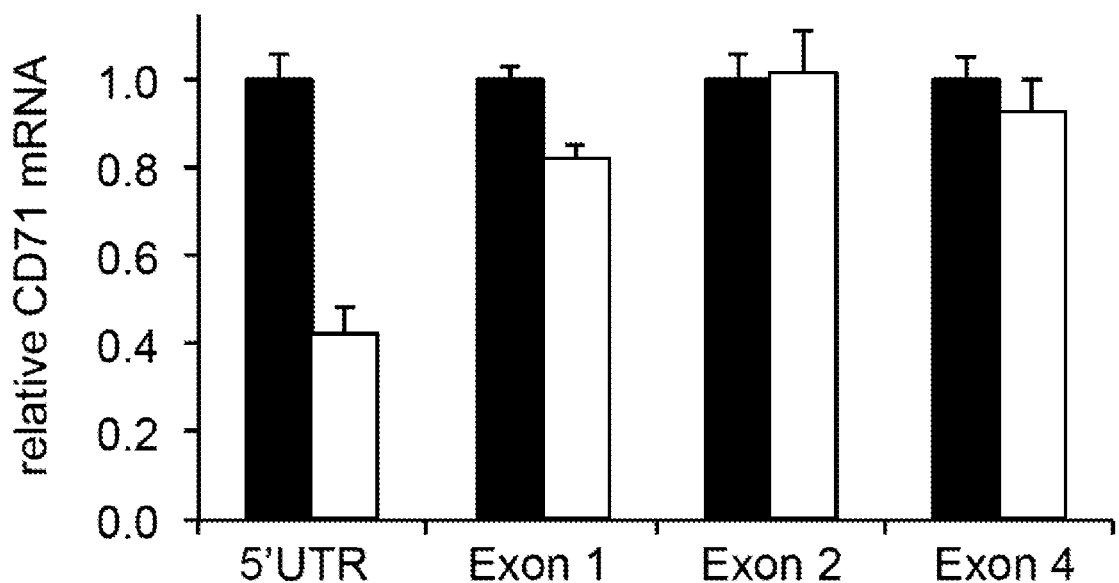
FIGS. 11A-11B are bar graphs showing light-activated CRISPR/Cas9 silencing of CD71 in HeLa cells. A) Quantitative real-time PCR analysis of CD71 mRNA, normalized to the GAPDH control gene. B) Fluorescence detection of cell-surface CD71 protein. Data is shown relative to nonirradiated cells for each condition, and error bars represent standard deviations from three replicates.
Figure 11B:
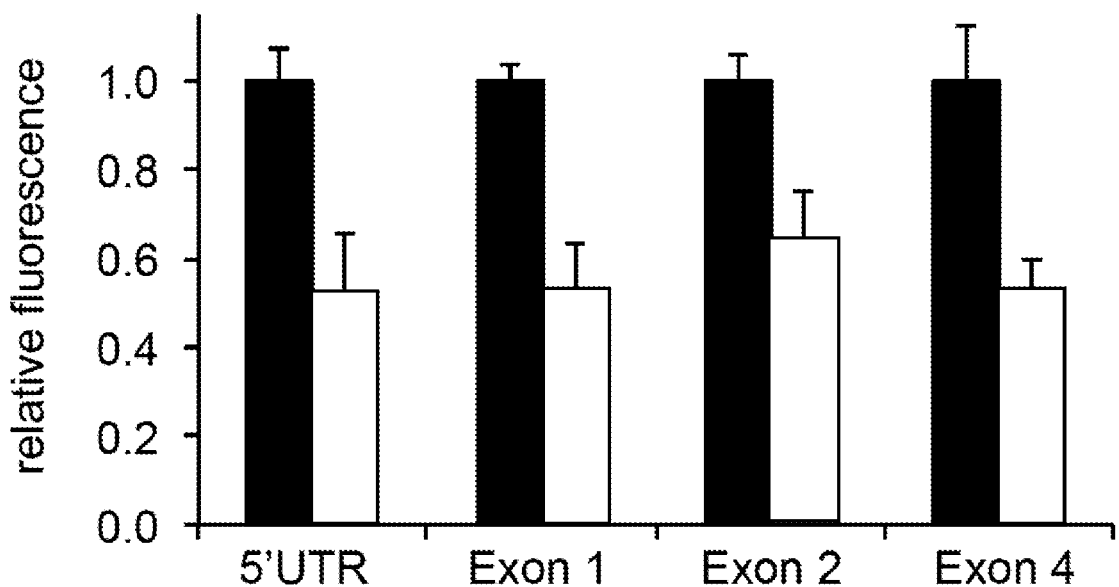

Next, the CD71 suppression was performed with the K866-caged Cas9 in the absence and presence of light-activation. Quantification of CD71 mRNA revealed a reduction by approximately 60% only in case of the gRNA targeting the CD71 5'UTR (FIG. 11A). This is not surprising as the introduction of mutations into the coding region of the CD71 gene should not affect transcription. Light-activation of Cas9 function reduced the presence of CD71 protein on the cell surface by approximately 50% (FIG. 11B), demonstrating the ability to optically control the silencing of endogenous genes with the disclosed caged CRISPR/Cas9 system.

Thus, the disclosed optically activated CRISPR/Cas9 system can be applied to the control of endogenous genes on both the genomic and the transcriptional level, depending on the target region of the gRNA.

Example 4

Materials and Methods

This example provides the materials and method for the results describe in Examples 5 and 6.

Chemical Synthesis of OABK HCl Salt

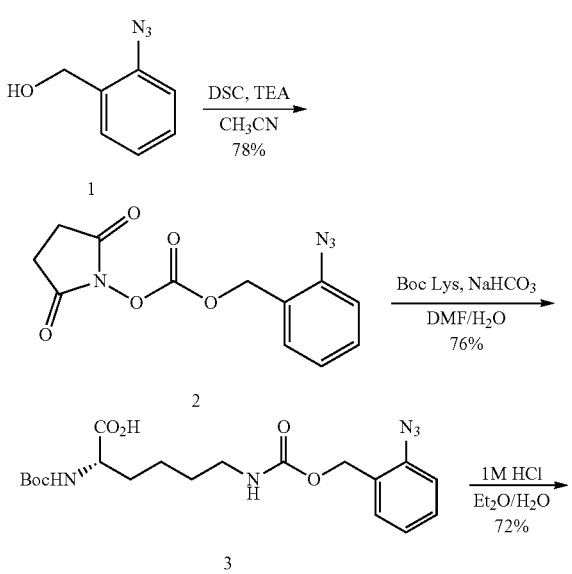

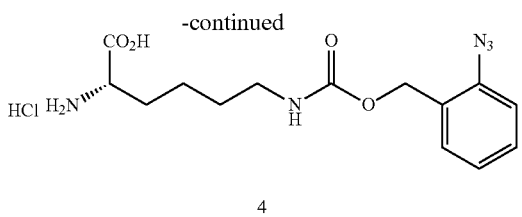

4

2-Azidobenzyl (2,5-dioxopyrrolidin-1-yl) carbonate (2)

N,N'-Disuccinimidyl carbonate (2 eq., 5.2 g, 20 mmol) was added to a solution of the alcohol 1 (1 eq., 1.5 g, 10 mmol) in CH$_3$CN (44 ml), followed by TEA (3 eq., 4.2 ml, 30 mmol). The reaction mixture was stirred overnight at room temperature and concentrated under reduced pressure. The crude product was purified by silica gel chromatography with DCM/acetone (19:1) as the eluent, affording 2 as a white solid in 78% yield (2.28 g, 7.8 mmol). $^1$H NMR (300 MHz, CDCl$_3$): δ=2.66 (s, 4H), 5.11 (s, 2H), 7.13-7.19 (m, 2H), 7.39-7.50 (m, 2H). $^{13}$C NMR (400 MHz, CDCl$_3$): δ=25.6, 73.6, 118.5, 125.0, 125.1, 131.2, 132.4, 139.8, 171.2. HRMS-LC: m/z calcd for C$_{12}$H$_9$N$_4$O$_5$ [M−H]$^-$: 289.0573; found: 289.0591.

N$^6$-(((2-Azidobenzyl)oxy)carbonyl)-N$^2$-(tert-butoxycarbonyl)-L-lysine (3)

Boc Lys (1.2 eq., 2.3 g, 9.4 mmol) was added to a solution of the carbonate 2 (1 eq., 2.28 g, 7.8 mmol) in 80 ml of DMF/water (1:1), followed by potassium carbonate (3 eq., 3.2 g, 23.4 mmol). The mixture was stirred overnight at room temperature, concentrated, acidified to pH 3-4 with 1 M aq. HCl, and extracted with Et$_2$O (3×20 ml). The combined organic layer was washed with water (30 ml) and brine (30 ml), and dried over Na$_2$SO$_4$. After filtration, the solvent was removed under reduced pressure, affording the product 3 as a yellow foam in 76% yield (2.6 g, 5.9 mmol). $^1$H NMR (300 MHz, CDCl$_3$): δ=1.42 (s, 9H), 1.42-1.90 (m, 6H), 3.15-3.23 (m, 2H), 4.23-4.50 (m, 1H), 5.06 (s, 2H), 6.95-7.02 (m, 2H), 7.35-7.37 (m, 2H). $^{13}$C NMR (400 MHz, CDCl$_3$): δ=13.7, 22.1, 27.8, 28.3, 28.4, 38.7, 52.9, 59.9, 72.4, 78.9, 117.6, 124.3, 126.5, 129.4, 130.9, 155.3, 161.9, 174.2. HRMS-LC: m/z calcd for C$_{19}$H$_{26}$N$_5$O$_6$[M−H]$^-$: 420.1918; found: 420.1904.

N$^6$-(((4-Azidobenzyl)oxy)carbonyl)-L-lysine hydrochloride salt (4)

A solution of 1 M aq. HCl (2.4 ml) was added to the Boc Lys 3 (1 eq, 100 mg, 0.24 mmol) in Et$_2$O (2.4 ml). The reaction mixture was stirred for 2 days and washed with Et$_2$O (3×5 ml). The aquious layer was concentrated under reduced pressure, affording the product 4 as a white solid in 72% yield (61.7 mg, 0.17 mmol). $^1$H NMR (400 MHz, DMSO): δ=1.23-1.49 (m, 4H), 1.69-1.71 (m, 2H), 2.97-2.99 (q, J=5.7 Hz, 2H), 3.80-3.85 (t, J=5.7 Hz, 1H), 4.96 (s, 2H), 7.18-7.46 (m, 4H). $^{13}$C NMR (400 MHz, DMSO): δ=21.31, 26.17, 29.29, 38.13, 51.90, 60.78, 118.58, 124.91, 127.95, 129.54, 129.59, 137.34, 155.85, 170.80. HRMS-LC: m/z calcd for C$_{14}$H$_{19}$N$_5$O$_4$ [M+H]$^+$: 322.1515; found: 322.1544.

Plasmid Construction for Mammalian Cell Applications 1) pMbPylOABKRS-mCherry-TAG-EGFP: The plasmid (pPylRS_Y271A-mCherry-TAG-EGFP) was obtained by converting the TAC (Y271) codon of wild type PylRS to a GGC (A271) codon using primers SEQ ID NO: 42 and 43 and a QuikChange site-directed mutagenesis kit (Agilent). In the following step, the plasmid (pPylRS_Y271A_Y349F-mCherry-TAG-EGFP) was generated by converting the TAC (Y349) codon of PylRS_Y271A into a TTC (F349) codon using primers SEQ ID NO: 44 and 45 and the same mutagenesis method.

2) pMbPylOABKRS: The E. coli codon-optimized plasmid (MbPylOABKRS_Y271A_Y349F) was constructed using the same mutagenesis method above. A and F mutations were introduced into wild type MbPylRS at Y271 and Y349 sites with two pairs of primers (SEQ ID NOS: 46/47 and SEQ ID NOS: 48/49), respectively.

3) pMbPylOABKRS-PylT: The plasmid was obtained by ligating the p4CMVE-U6-PylT fragment from pMb4PylT between the restriction sites NheI and MfeI sites of pMbOABKRS.

4) pMbPylOABKRS-wtCre and pMbPylOABKRS-Cre-K201TAG: The pwtCre and pCre-K201TAG fragments were PCR amplified using the primers SEQ ID NO: 50 and 51, digested with NheI and MfeI, and ligated into the pMbPylOABKRS-mCherry-TAG-EGFP vector in place of the mCherry-EGFP, generating the pOABKRS-wtCre and pOABKRS-Cre-K201TAG plasmid, respectively.

5) pMbPylOABKRS-wtCas9 and pMbPylOABKRS-Cas9-K866TAG: The pwtCas9 and pCas9-K866TAG fragments were generated from pMbCKRS-wtCas9 and pMbCKRS-Cas9-K866TAG using the NheI and MfeI restriction sites, respectively. pMbPylOABKRS-mCherry-TAG-EGFP was digested with the same restriction enzymes (NheI and MfeI) to remove the mCherry-TAG-EGFP-HA reporter. The wtCas9 and Cas9-K866TAG genes were ligated into the pMbPylOABKRS-mCherry-TAG-EGFP backbone replacing the mCherry-EGFP using Quick ligase (NEB) to create pMbPylOABKRS-wtCas9 and pMbPylOABKRS-Cas9-K866TAG, respectively.

TABLE 7

| Primer sequences | |
|---|---|
| SEQ ID NO: 42 | ctatgctggcccccaccctggccaactacctgcggaaactg |
| SEQ ID NO: 43 | cagtttccgcaggtagttggccagggtgggggccagcatag |
| SEQ ID NO: 44 | gcgacagctgcatggtgttcggcgacaccctggacatc |
| SEQ ID NO: 45 | gatgtccagggtgtcgccgaacaccatgcagctgtcgc |
| SEQ ID NO: 46 | ctatgctggccgccaccctggccaactacctgcggtaactg |
| SEQ ID NO: 47 | cagttaccgcaggtagttggccagggtggcggccagcatag |

TABLE 7-continued

Primer sequences

SEQ ID NO: 48    gcgacagctgcatggtgttcggcgacaccctggacatc

SEQ ID NO: 49    gatgtccagggtgtcgccgaacaccatgcagctgtcgc

SEQ ID NO: 50    gtcagatccgctagcacc

SEQ ID NO: 51    cgatcgatatcaattgtggtttgtccaaactcatca

Protein Expression, Purification, and Deprotection.

The plasmid pBAD-sfGFP-Y151TAG-pylT was co-transformed with pBK-OABKRS into chemically competent E. coli Top10 cells. A single colony was used to inoculate LB media overnight and 500 µL of the overnight culture was added to 25 mL of LB media, supplemented with 1 mM of OABK and 25 µg/mL of tetracycline and 50 µg/mL of kanamycin. Cells were grown at 37° C., 250 rpm, and protein expression was induced with 0.2% arabinose when the OD600 reached ~0.5. After overnight expression at 37° C., cells were pelleted and washed once with PBS. The cell pellet was re-suspended in 6 mL of phosphate lysis buffer (50 mM, pH 8.0) and Triton X-100 (60 µL, 10%), gently mixed, and incubated for an hour at 4° C. The cell suspensions were sonicated with 6 short burst of 30 s followed by intervals of 30 s for cooling, and then the cell lysates were centrifuged at 4° C., 13,000 g, for 10 minutes. The supernatant was transferred to a 15 mL conical tube and 100 µL of Ni-NTA resin (Qiagen) was added. The mixture was incubated at 4° C. for 2 h under shaking. The resin was then collected by centrifugation (500 g, 10 min), washed twice with 400 µL of lysis buffer, followed by two washes with 400 µL of wash buffer containing 20 mM imidazole. The protein was eluted with 400 µL of elution buffer containing 250 mM imidazole. After lysis of a bacterial expression culture, a Staudinger reaction was performed with 5 (1 mM) in cell lysates for 4 h at room temperature under shaking (250 rpm). The reaction mixture was centrifuged (5,000 rpm, 5 min) and the supernatant was transferred to a 15 mL conical tube followed by protein purification as described above. The purified proteins were analyzed by 10% SDS PAGE and stained with Coomassie Blue. ESI-MS analysis was carried out to show the incorporation of OABK into sfGFP and its deprotection.

Incorporation of OABK in Mammalian Cells.

HEK 293T cells were seeded into a 6-well cell culture microplate and grown to approximately 80% confluence in Dulbecco's modified eagle medium (DMEM) with 10% fetal bovine serum (FBS) and 1% penicillin/streptomycin. Cells were transfected with two plasmids, pMbPy-lOABKRS-mCherry-TAG-EGFP-HA and p4CMVE-U6-PylT. Transfection was carried out using linear PEI (Millipore), according to the manufacturer's protocol. The growth media with 10% FBS contained either OABK (0.5 mM) or no unnatural amino acid. Cells were imaged on a Zeiss AxioObserver for mCherry and EGFP fluorescence after 20 h. Cells were then lysed using Lysis Buffer (Sigma) supplemented with complete protease inhibitor cocktail (Sigma). After lysis, the cell debris was pelleted and the supernatant was added to 4×SDS sample loading buffer. Samples were analyzed by SDS-PAGE. Western blotting was carried out to detect reporter protein using mouse anti-HA antibody (Cell Signaling), visualized with an anti-mouse HRP conjugate (Santa Cruz). As a protein loading control, Western blotting was also carried out to detect the endogenous levels of total GAPDH protein using a mouse anti-GAPDH antibody (Santa Cruz) visualized with an HRP-conjugated anti-mouse secondary antibody (Santa Cruz).

Live-Cell Fluorescence Imaging and Fluorescence Measurement.

HEK 293T cells were seeded into an 8-well chamber slide (Lab-Tek) and allowed to grow to approximately 70% confluence in DMEM (10% FBS). Co-transfection of pOABKRS-4PylT and pEGPF-K29TAG-SatB1-mCherry or pEGFP-K85TAG-mCherry was carried out using the same protocol as above. After transfection, cells were grown for 20 h, the growth media with transfection mixtures was removed, and phenol red-free DMEM without OABK was used to wash cells three times, followed by a 3 h incubation in order to remove any non-incorporated OABK, followed by treatment with 5 (0.5 mM) and fluorescence imaging (a micrograph was collected every 5 min using a Nikon A1 confocal microscope with a Plan Apochromat 40× oil objective at 2× scan zoom) for 5 h. The mean fluorescence intensities in the nucleus, in case of activation of SatB1-mCherry, or the cytoplasm, in the case of EGFP activation, were quantified using NIS Elements software to enable the Fnt/Fnmax or Fct/Fcmax ratio to be determined and normalized.

Luciferase Assay to Screen Different Phosphines for Protein Activation in Cells.

Plasmids that encode pGL3-K206TAG and pOABKRS-PylT were transfected in the presence of OABK using the same protocol as above. Cells were washed three times and incubated in fresh medium for 2 h to remove OABK, followed by phosphine treatment for 4 h. Luciferase activity was measured using a microplate reader (Tecan M100PRO) and a BrightGlo luciferase assay kit (Promega).

Small Molecule Activation of Cre-OABK in Live Cells.

HEK 293T cells were plated into a 96-well cell culture microplate (Greiner), and incubated overnight in DMEM growth media supplemented with 10% FBS and 1% penicillin/streptomycin at 37° C. in 5% $CO_2$. At ~75% confluency, HEK293T cells were co-transfected with the pMbOABKRS-wtCre or pMbOABKRS-CreK201TAG, p4CMVE-U6-PylT[3], and pC-SL plasmid (100 ng of each) using linear PEI (2 µL per well) in the presence or absence of OABK (0.25 mM) overnight at 37° C. The media supplemented with OABK (0.25 mM) was replaced with fresh DMEM and incubation was continued for 2 h, and then followed by addition of 5 (0.5 mM) at 37° C. Fluorescence imaging of the Cre activation reporter was performed after 24 h incubation. Media was replaced with DMEM without phenol red (Thermo Scientific) for microscopy imaging on a Zeiss Observer Z1 microscope (10× objective, NA 0.8 plan-apochromat) with DsRed ($E_x$: BP550/25; $E_m$: BP605/70) and EGFP ($E_x$: BP470/40; $E_m$: BP525/50) filter cubes, then processed in Zen Pro 2012 imaging software. Fluorescent cell counting was performed on a Nikon A1 confocal microscope (10× objective) and analyzed using Elements software.

Small Molecule Activation of Cas9-OABK in Live Cells.

HEK 293T cells were seeded into a 96-well cell culture microplate (Greiner), and incubated overnight in DMEM growth media supplemented with 10% FBS and 1% penicillin/streptomycin at 37° C. in 5% $CO_2$ humidified atmosphere. Before transfection, media was replaced with antibiotics-free DMEM supplemented with or without OABK (0.25 mM). Quadruple transfections were carried out with linear PEI using pMbOABKRS-wtCas9 or pMbOABKRS-Cas9-K866TAG, p4CMVE-U6-PylT (Gautier et al., *J Am Chem Soc* 132, 4086-4088, 2010), gRNA plasmids (Hemphill et al., *J Am Chem Soc* 137, 5642-5645, 2015), and pRG dual reporter plasmid ((Hemphill et al., *J Am Chem Soc* 137, 5642-5645, 2015)) (100 ng of each). After a 24 h incubation, cells were washed with fresh DMEM and incubated for 2 h. For regulating gene editing in live cells, HEK 293T cells were treated with 5 (0.5 mM) or without 5. After overnight incubation, media was replaced with DMEM without phenol red, and cells were imaged on a Zeiss Observer Z1 microscope (10× objective, NA 0.8 plan-apochromat) with EGFP BP470/40; $E_m$: BP525/50) and DsRed BP550/25; $E_m$: BP605/70) filter cubes. Fluorescent cell counting was performed on a Nikon A1 confocal microscope (10× objective) and analyzed using Elements software.

Example 5

Generation of a Cas9 that can be Activated with Small Molecules

This example describes methods used to modify Cas9 such that it can be activated using small molecules.

A small molecule switch was designed through the inactivation of protein function via site-specific incorporation of an ortho-azidobenzyloxycarbonyl lysine (OABK, FIG. 13A), followed by Cas9 protein activation through bioorthogonal deprotection employing a Staudinger reduction. The Staudinger reduction-induced deprotection of amino acids adds an additional tool to chemical and photochemical peptide and protein activation approaches (such as the light activation approach described in the above examples). Azide groups installed on biological molecules are non-toxic and fully orthogonal to all cellular chemistries.

Genetic Encoding of OABK and Deprotection In Vitro.

Figure 13A:
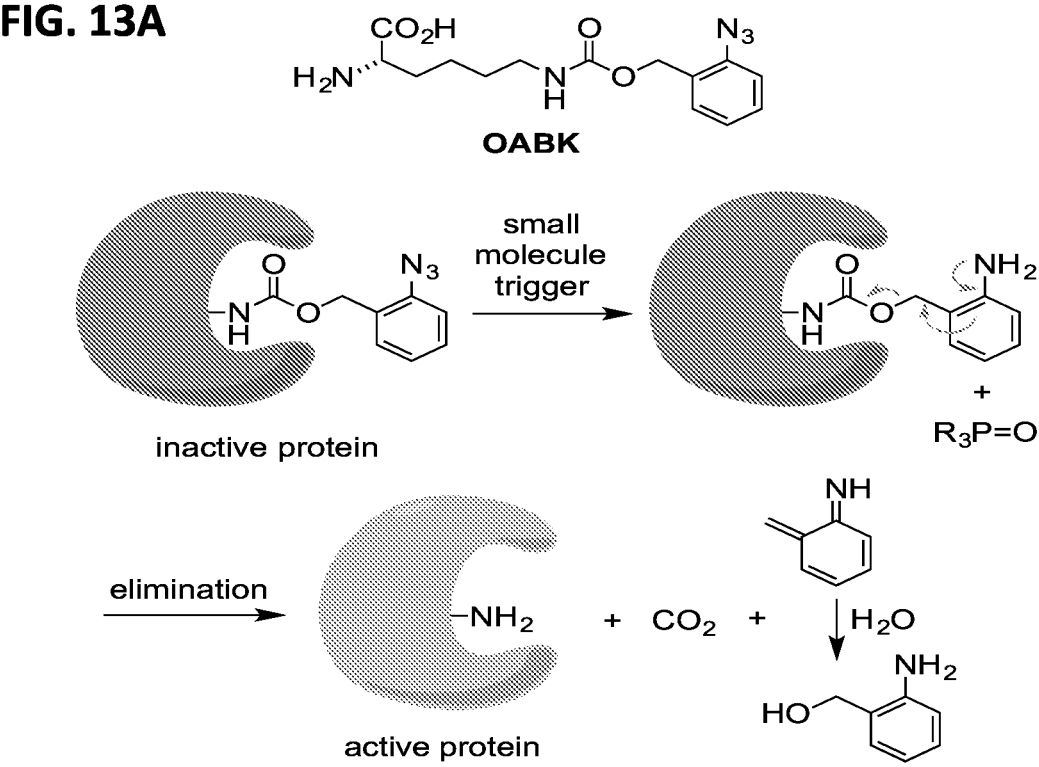
FIG. 13A shows generation of an OABK-modified Cas9 that can be activated using small molecules. Structure of ortho-azidobenzyloxycarbonyl lysine (OABK) and schematic of the phosphine-triggered protein activation through protecting group removal via Staudinger reduction.
Figure 13B:
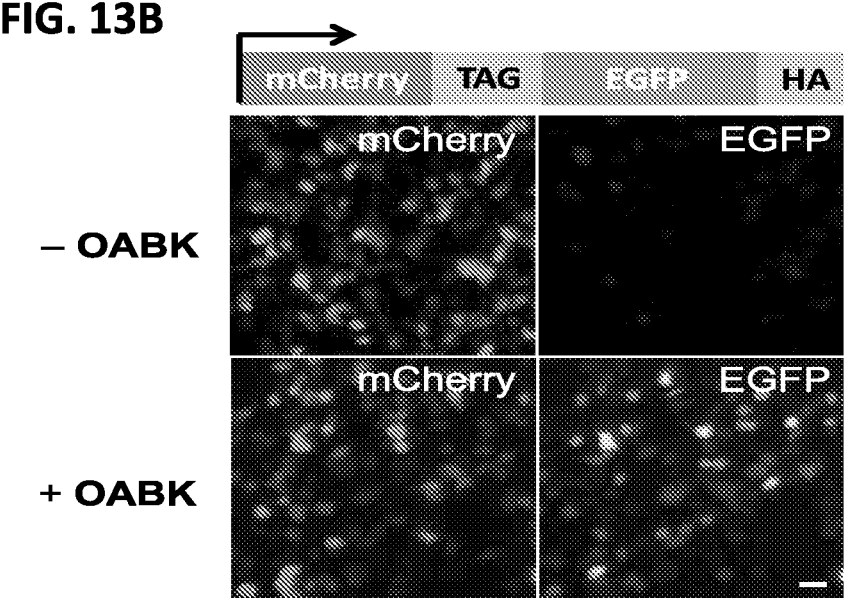
FIGS. 13B-13C show digital images of (B) micrographs and a (C) Western blot of an mCherry-TAG-EGFP construct in order to confirm genetic encoding of OABK in human cells. B) Digital images confirming amino acid-dependent incorporation of OABK into mCherry-TAG-EGFP-HA in HEK293T cells. Scale bar represents 20 µm. C) Confirmation of full-length protein expression through an anti-HA Western blot.
Figure 13C:

The amino acid OABK was synthesized in three steps from 2-azidobenzyl alcohol via a succinimidyl carbonate (see Example 4). Phosphine-induced Staudinger reduction of OABK yields an aniline derivative that undergoes a 1,4-elimination and decarboxylation, as confirmed by LC/MS analysis (FIG. 13A). Efficient deprotection of OABK through phosphine treatment was further confirmed in a time-course examination. This results in the formation of lysine and, when OABK is incorporated into a protein, the formation of active, wild-type protein. Several unnatural lysine derivatives have been genetically encoded through the addition of engineered pyrrolysyl tRNA/tRNA synthetase pairs to the translational machinery of bacterial, yeast, and human cells. Based on the Y271A/Y349F PylRS mutant (termed OABKRS) (Yanagisawa et al., Chem Biol 15, 1187-1197, 2008), the incorporation of OABK into proteins in mammalian cells was demonstrated (FIGS. 13B-13C).

Generation of OABK-Cas9.

To implement the Staudinger reduction switch, OABK was incorporated into Cas9 at position K866 using a tRNA/tRNA syntheaste pair in a similar method as was used to generate PCK-Cas9. The wild-type pyrrolysine tRNA synthetase from *M. barkeri* containing two mutations, Y271A and Y349F, was used (see Yanagisawa et al., *Chem Biol* 15:1187-1197, 2008, herein incorporate by reference).

Activation of OABK-GFP.

A plasmid encoding the synthetase and an amber-suppressor reporter (pOABKRS-mCherry-TAG-EGFP-HA, FIGS. 16A-16H), together with a plasmid encoding the tRNA (p4CMVE-U6-PylT), was transfected into human embryonic kidney (HEK) 293T cells. The cells were incubated for 24 hrs in the absence or presence of OABK (0.5 mM) and fluorescence imaging revealed EGFP expression only in the presence of the unnatural amino acid (FIG. 13B). This was further confirmed by Western blot analysis with an anti-HA antibody (FIG. 13C). These results are in agreement with OABK-dependent protein expression in bacterial cells and confirm the high fidelity of the OABKRS in both prokaryotic and eukaryotic systems.

The efficient incorporation, a sfGFP-OABK protein yield of 12 mg/L was obtained in *E. coli*, was further confirmed by electrospray ionization mass spectrometry (ESI-MS), revealing an experimentally obtained mass of 28402.75 Da, in agreement with the expected mass of 28403.03 Da. Furthermore, an efficient in vitro protein deprotection through Staudinger reduction in PBS buffer (pH 7.4) at 37° C. for 4 h was confirmed by mass spec analysis of sfGFP-OABK after treatment with the small molecule trigger (the observed mass of 28226.41 Da for deprotected sfGFP matches the expected mass of 28227.89 Da; deprotection was quantitative and no protected sfGFP-OABK was detected.

Example 6

Small Molecule-Triggered CRISPR/Cas9 Gene Editing

This example describes methods used to demonstrate that the OABK-modified Cas9 generated in Example 5 can be activated using small molecules, namely with phosphines.

Conditional regulation of Cas9 enzymatic activity provides spatial and temporal control over gene editing and to mitigate off-target effects observed with constitutively active Cas9 (Davis et al., Nat Chem Biol 11, 316-U397, 2015; Zetsche et al., Nat Biotechnol 33, 139-142, 2015). To implement the Staudinger reduction switch, OABK was incorporated into Cas9 at position K866.

The function of Cas9-OABK in the absence and presence of phosphine derivatives 5 and 6 (see FIG. 14) was investigated using a DsRed/EGFP dual reporter assay (FIG. 15A). Cells expressing Cas9-OABK only showed DsRed fluorescence, because transcription terminates after DsRed in the absence of activated Cas9, indicating complete inhibition of enzymatic function. Once Cas9-OABK is activated by the small molecule phosphine, the complex of functional Cas9 and gRNAs induces excision of the DsRed-terminator cassette, followed by NHEJ repair, and leading to EGFP expression.

As shown in FIG. 15B, the expression level of Cas9-K866-*OABK is similar to wild-type Cas9 expression in mammalian cells. In addition, the activity after small molecule triggering almost reached wild-type levels (FIG. 15C). To optimize the concentration of phosphines for activation of gene editing in live cells, varying concentrations of 2-(diphenylphosphino)benzoic acid (2DPBA, 5), and 2-(diphenylphosphino)benzamide (2DPBM, 6) were investigated. Consistent with the other small molecule-triggered processes, dose-dependent results were obtained, and 25 µM was identified as the universally effective concentration of 6 for activation of Cas9-OABK and other proteins in live cells (FIG. 15D). These experiments demonstrate that conditional activation of CRISPR/Cas9 gene editing can be accomplished via a Staudinger reduction.

Thus, the Staudinger-reduction induced protein activation expands the toolbox for conditionally controlled protein control in live cells. It compares favorably to palladium-mediated and Diels-Alder-mediated protein deprotection methods, since benign phosphine reagents have been extensively used in biological studies, since low concentrations (as low as 25 µM) of the small molecule trigger were found to efficiently activate protein function, and since synthesis of OABK and its incorporation into proteins in both bacterial and mammalian systems is highly efficient. In addition, the protein triggering through Staudinger reduction is expected to be compatible and orthogonal to the palladium- and cycloaddition-based deprotection reactions.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A non-naturally occurring activatable Cas9 protein, comprising an amino acid sequence with at least 80% sequence identity to SEQ ID NO: 39 or SEQ ID NO: 41 and at least one light activatable lysine or at least one chemically activatable lysine located at amino acid position 163, 510, or 866 according to the reference Cas9 sequence set forth as SEQ ID NO: 39.

2. The activatable Cas9 protein of claim 1, wherein the activatable Cas9 protein comprises:
an amino acid sequence with at least 95% sequence identity to SEQ ID NO: 39 or SEQ ID NO: 41, and the at least one light activatable or chemically activatable lysine is located at amino acid position 163, 510, or 866 according to the reference Cas9 sequence set forth as SEQ ID NO: 39.

3. A non-naturally occurring activatable Cas9 protein, comprising at least one light activatable lysine or at least one chemically activatable lysine wherein the activatable Cas9 protein comprises the amino acid sequence set forth as SEQ ID NO: 39 or 41, and wherein at least one of the lysine residues at amino acid position 163, 510, or 866 of SEQ ID NO: 39 or 41 is a photocaged or a chemically activatable lysine residue.

4. The activatable Cas9 protein of claim 1, wherein the chemically activatable lysine or the light activatable lysine comprises a compound selected from the following:

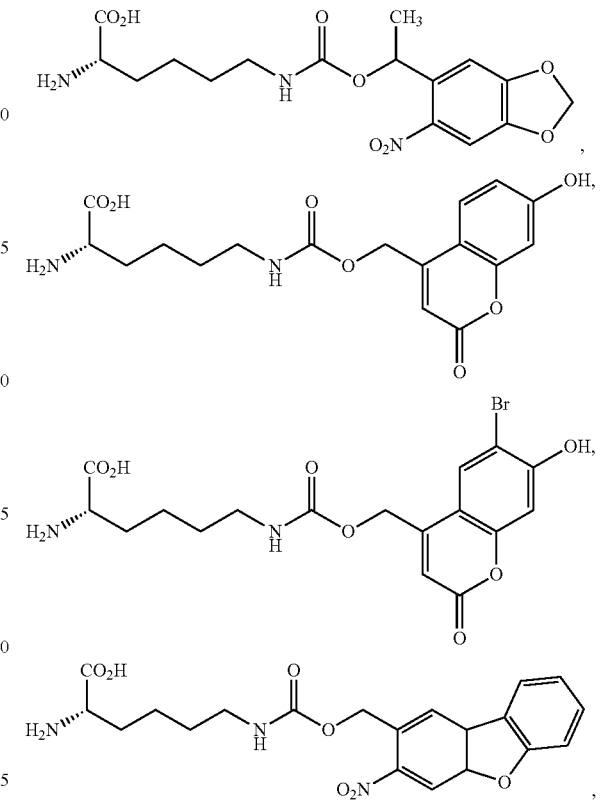

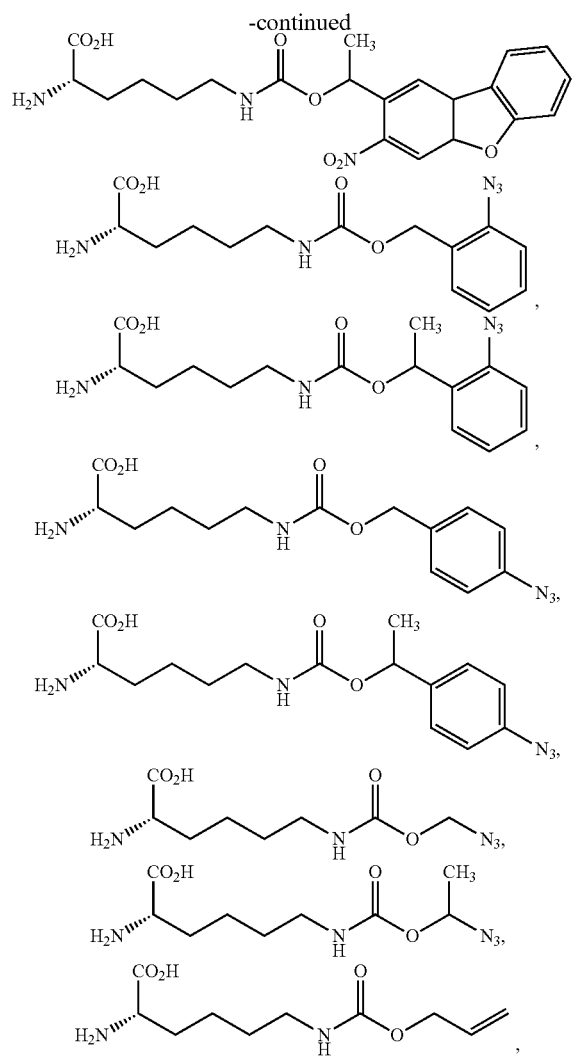

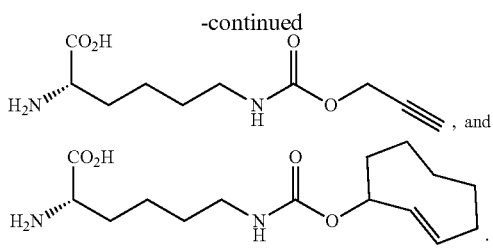

5. A kit comprising the activatable Cas9 protein of claim 1.

6. The kit of claim 5, further comprising one or more of:
bacterial cell growth media, mammalian cell growth media, OABK, PCK, an isolated nucleic acid molecule encoding a tRNA, an isolated nucleic acid molecule encoding a tRNA synthetase, an isolated guide nucleic acid molecule specific for a target nucleic acid molecule, and phosphine or phosphine derivative.

7. The activatable Cas9 protein of claim 1, wherein the activatable Cas9 protein comprises:
the light activatable lysine or the chemically activatable lysine located at amino acid position 163 according to the reference Cas9 sequence set forth as SEQ ID NO: 39.

8. The activatable Cas9 protein of claim 1, wherein the activatable Cas9 protein comprises:
the light activatable lysine or the chemically activatable lysine located at amino acid position 866 according to the reference Cas9 sequence set forth as SEQ ID NO: 39.

9. The activatable Cas9 protein of claim 1, wherein the chemically activatable lysine comprises ortho-azidobenzyloxycarbonyl lysine (OABK).

10. The activatable Cas9 protein of claim 1, wherein the light activatable lysine comprises photocaged lysine (PCK).

* * * * *

SEQUENCE LISTING

```
<160> NUMBER OF SEQ ID NOS: 52

<210> SEQ ID NO 1
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 1
ttaagctagc accatggaca agaagt                                          26

<210> SEQ ID NO 2
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 2
cggtgaattc ttaagcgtaa tctggaacat cgtatgggta caccttcctc ttcttc        56

<210> SEQ ID NO 3
<211> LENGTH: 97
<212> TYPE: DNA
<213> ORGANISM: Artificial Sequence
<220> FEATURE:
<223> OTHER INFORMATION: Synthetic polynucleotide

<400> SEQUENCE: 3
tcgactctag aggatccacg ttttagagct agaaatagca agttaaaata aggctagtcc    60
gttatcaact tgaaaaagtg gcaccgagtc ggtgctt                             97

<210> SEQ ID NO 4
<211> LENGTH: 98
<212> TYPE: DNA
<213> ORGANISM: Artificial Sequence
<220> FEATURE:
<223> OTHER INFORMATION: Synthetic polynucleotide

<400> SEQUENCE: 4
tagctagtct aggtcgatgc gttttagagc tagaaatagc aagttaaaat aaggctagtc    60
cgttatcaac ttgaaaaagt ggcaccgagt cggtgctt                            98

<210> SEQ ID NO 5
<211> LENGTH: 98
<212> TYPE: DNA
<213> ORGANISM: Artificial Sequence
<220> FEATURE:
<223> OTHER INFORMATION: Synthetic polynucleotide
```

<400> SEQUENCE: 5
ggacgcgcta gtgtgagtgc gttttagagc tagaaatagc aagttaaaat aaggctagtc    60
cgttatcaac ttgaaaaagt ggcaccgagt cggtgctt                            98

<210> SEQ ID NO 6
<211> LENGTH: 98
<212> TYPE: DNA
<213> ORGANISM: Artificial Sequence
<220> FEATURE:
<223> OTHER INFORMATION: Synthetic polynucleotide

<400> SEQUENCE: 6
gtcatatacc cggttcagcc gttttagagc tagaaatagc aagttaaaat aaggctagtc    60
cgttatcaac ttgaaaaagt ggcaccgagt cggtgctt                            98

<210> SEQ ID NO 7
<211> LENGTH: 98
<212> TYPE: DNA
<213> ORGANISM: Artificial Sequence
<220> FEATURE:
<223> OTHER INFORMATION: Synthetic polynucleotide

<400> SEQUENCE: 7
ctgcagcacg tcgcttatat gttttagagc tagaaatagc aagttaaaat aaggctagtc    60
cgttatcaac ttgaaaaagt ggcaccgagt cggtgctt                            98

<210> SEQ ID NO 8
<211> LENGTH: 98
<212> TYPE: DNA
<213> ORGANISM: Artificial Sequence
<220> FEATURE:
<223> OTHER INFORMATION: Synthetic polynucleotide

<400> SEQUENCE: 8
gggttatgtg gcgtatagta gttttagagc tagaaatagc aagttaaaat aaggctagtc    60
cgttatcaac ttgaaaaagt ggcaccgagt cggtgctt                            98

<210> SEQ ID NO 9
<211> LENGTH: 319
<212> TYPE: DNA
<213> ORGANISM: Artificial Sequence
<220> FEATURE:
<223> OTHER INFORMATION: Synthetic polynucleotide

<400> SEQUENCE: 9
tgtacaaaaa agcaggcttt aaaggaacca attcagtcga ctggatccgg taccaaggtc    60
gggcaggaag agggcctatt tcccatgatt ccttcatatt tgcatatacg atacaaggct   120
gttagagaga taattagaat taatttgact gtaaacacaa agatattagt acaaaatacg   180
tgacgtagaa agtaataatt tcttgggtag tttgcagttt taaaattatg ttttaaaatg   240
gactatcata tgcttaccgt aacttgaaag tatttcgatt tcttggcttt atatatcttg   300
tggaaaggac gaaacaccg                                                319

<210> SEQ ID NO 10
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 10
gcagagcgaa tcggatctgc tacctgcagg agatc                                 35

<210> SEQ ID NO 11
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 11
cgattcgctc tgcgggtata tctgcgccgt gctgt                                 35

<210> SEQ ID NO 12
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 12
tatgatcgca tttcggggac acttcctcat cgagggg                               37

<210> SEQ ID NO 13
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 13
cccgaaatgc gatcatatgc gccagcgcga gatagat                               37

<210> SEQ ID NO 14
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 14
cttcctgcac actctctgct gtacgagtac ttcacagttt ataacgagct caccaa         56

<210> SEQ ID NO 15
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 15
agagtgtgca ggaagcacct tttcgttagg cagatttta tcaaagttag tcatcc          56

<210> SEQ ID NO 16
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 16
accgttgcgg tcgtggatga actcgtcaaa gtaa                                  34

<210> SEQ ID NO 17
<211> LENGTH: 34

```
<212> TYPE: DNA
<213> ORGANISM: Artificial Sequence
<220> FEATURE:
<223> OTHER INFORMATION: Synthetic polynucleotide

<400> SEQUENCE: 17
cgaccgcaac ggtctgcagt attccctttt tgat                               34

<210> SEQ ID NO 18
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 18
agaggggcga gtgataacgt cccctcagaa g                                  31

<210> SEQ ID NO 19
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 19
tcactcgccc ctctattttt atcggatctt gtcaacac                           38

<210> SEQ ID NO 20
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 20
cgcagataga atcggatctg ctacctgcag gagatc                             36

<210> SEQ ID NO 21
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 21
ccgattctat ctgcgggtat atctgcgccg tgctgt                             36

<210> SEQ ID NO 22
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 22
tatgatctag tttcggggac acttcctcat cgagggg                            37

<210> SEQ ID NO 23
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 23
```
cccgaaacta gatcatatgc gccagcgcga gatagat                                    37

<210> SEQ ID NO 24
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 24
cttccttagc actctctgct gtacgagtac ttcacagttt ataacgagct caccaa       56

<210> SEQ ID NO 25
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 25
agagtgctaa ggaagcacct tttcgttagg cagattttta tcaaagttag tcatcc       56

<210> SEQ ID NO 26
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 26
accgtttagg tcgtggatga actcgtcaaa gtaa                                       34

<210> SEQ ID NO 27
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 27
cgacctaaac ggtctgcagt attccctttt tgat                                       34

<210> SEQ ID NO 28
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 28
agagggtaga gtgataacgt cccctcagaa g                                          31

<210> SEQ ID NO 29
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 29
tcactctacc ctctattttt atcggatctt gtcaacac                                   38

<210> SEQ ID NO 30
<211> LENGTH: 121
<212> TYPE: DNA
<213> ORGANISM: Artificial Sequence

```
<220> FEATURE:
<223> OTHER INFORMATION: Synthetic polynucleotide

<400> SEQUENCE: 30
taatacgact cactataggg agatagctag tctaggtcga tgcgttttag agctagaaat      60
agcaagttaa aataaggcta gtccgttatc aacttgaaaa agtggcaccg agtcggtgct    120
t                                                                   121

<210> SEQ ID NO 31
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 31
taatacgact cactataggg agatcgactc tagaggatcc acgttttaga gctagaaata     60
gcaagttaaa ataaggctag tccgttatca acttgaaaaa gtggcaccga gtcggtgctt   120

<210> SEQ ID NO 32
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 32
taatacgact cactataggg                                                 20

<210> SEQ ID NO 33
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 33
aaagcaccga ctcggtgcca                                                 20

<210> SEQ ID NO 34
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 34
tgcaccacca actgcttagc                                                 20

<210> SEQ ID NO 35
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 35
ggcatggact gtggtcatga g                                               21

<210> SEQ ID NO 36
<211> LENGTH: 20
<212> TYPE: DNA
<213> ORGANISM: Artificial Sequence
<220> FEATURE:
```

```
<223> OTHER INFORMATION: Synthetic polynucleotide

<400> SEQUENCE: 36
aaaatccggt gtaggcacag                                                    20

<210> SEQ ID NO 37
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 37
gcactccaac tggcaaagat                                                    20

<210> SEQ ID NO 38
<211> LENGTH: 4107
<212> TYPE: DNA
<213> ORGANISM: Streptococcus pyogenes

<400> SEQUENCE: 38
atggataaga aatactcaat aggcttagat atcggcacaa atagcgtcgg atgggcggtg        60
atcactgatg attataaggt tccgtctaaa aagttcaagg ttctgggaaa tacagaccgc       120
cacagtatca aaaaaatct tatagggct cttttatttg acagtggaga cagcggaa           180 gcgactcgtc tcaaacggac agctcgtaga aggtatacac gtcggaagaa tcgtatttgt       240
tatctacagg agattttttc aaatgagatg gcgaaagtag atgatagttt ctttcatcga       300
cttgaagagt ctttttttggt ggaagaagac aagaagcatg aacgtcatcc tatttttgga     360
aatatagtag atgaagttgc ttatcatgag aaatatccaa ctatctatca tctgcgaaaa       420
aaattggtag attctactga taaagcggat ttgcgcttaa tctatttggc cttagcgcat       480
atgattaagt tcgtggtca ttttttgatt gagggagatt taaatcctga taatagtgat        540
gtggacaaac tatttatcca gttggtacaa acctacaatc aattatttga agaaaaccct       600
attaacgcaa gtggagtaga tgctaaagcg attctttctg cacgattgag taaatcaaga       660
cgattagaaa atctcattgc tcagctcccc ggtgagaaga aaaatagctt atttgggaat       720
ctcattgctt tgtcattggg tttgaccct aatttttaaat caatttttga tttggcagaa       780
gatgctaaat tacagctttc aaaagatact tacgatgatg atttagataa tttattggcg       840
caaattggag atcaatatgc tgatttgttt ttggcagcta gaatttatc agatgctatt       900 ttactttcag atatcctaag agtaaatact gaaataacta aggctcccct atcagcttca       960
atgattaaac gctacgatga acatcatcaa gacttgactc ttttaaaagc tttagttcga      1020
caacaacttc cagaaaagta taagaaaatc tttttttgatc aatcaaaaaa cggatatgca      1080
ggttatattg atgggggagc tagccaagaa gaatttttata aatttatcaa accaatttta    1140
gaaaaaatgg atggtactga ggaattattg gtgaaactaa atcgtgaaga tttgctgcgc      1200
aagcaacgga ccttttgacaa cggctctatt ccccatcaaa ttcacttggg tgagctgcat    1260
gctattttga aagacaaga agactttat ccatttttaa aagacaatcg tgagaagatt       1320
gaaaaaatct tgactttccg aattccttat tatgttggtc cattggcgcg tggcaatagt     1380
cgttttgcat ggatgactcg gaagtctgaa gaaacaatta ccccatggaa ttttgaagaa      1440
gttgtcgata aggtgcttc agctcaatca tttattgaac gcatgacaaa ctttgataaa      1500
aatcttccaa atgaaaaagt actaccaaaa catagtttgc tttatgagta ttttacggtt     1560
tataacgaat tgacaaaggt caaatatgtt actgaaggaa tgcgaaaacc agcatttctt      1620
```

```
tcaggtgaac agaagaaagc cattgttgat ttactcttca aaacaaatcg aaaagtaacc   1680
gttaagcaat taaagaaga ttatttcaaa aaatagaat gttttgatag tgttgaaatt     1740
tcaggagttg aagatagatt taatgcttca ttaggtacct accatgattt gctaaaaatt   1800
attaaagata aagattttt ggataatgaa gaaaatgaag atatcttaga ggatattgtt    1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040 gatttttga aatcagatgg ttttgccaat cgcaattta tgcagctgat ccatgatgat     2100
agtttgacat ttaagaaga cattcaaaaa gcacaagtgt ctggacaagg cgatagttta   2160
catgaacata ttgcaaattt agctggtagc cctgctatta aaaaggtat tttacagact    2220 gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta agtgattac cttaaaatct    2880 aaattagttt ctgacttccg aaaagatttc caattctata agtacgtga gattaacaat    2940 taccatcatg cccatgatgc gtatctaaat gccgtcgttg gaactgcttt gattaagaaa   3000
tatccaaaac ttgaatcgga gtttgtctat ggtgattata agtttatga tgttcgtaaa    3060 atgattgcta agtctgagca agaaataggc aaagcaaccg caaaatattt ctttactct    3120 aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttat    3360 gctcgtaaaa aagactggga tccaaaaaaa tatggtggtt ttgatagtcc aacggtagct   3420
tattcagtcc tagtggttgc taaggtgaaa aagggaaat cgaagaagtt aaaatccgtt    3480
aaagagttac tagggatcac aattatggaa agaagttcct ttgaaaaaaa tccgattgac   3540 ttttagaag ctaaaggata taaggaagtt aaaaaagact taatcattaa actacctaaa    3600
tatagtcttt ttgagttaga aaacggtcgt aaacggatgc tggctagtgc cggagaatta   3660 caaaaggaa atgagctggc tctgccaagc aaatatgtga attttttata tttagctagt    3720
cattatgaaa agttgaaggg tagtccagaa gataacgaac aaaaacaatt gtttgtggag   3780
cagcataagc attatttaga tgagattatt gagcaaatca gtgaattttc taagcgtgtt   3840
attttagcag atgccaattt agataaagtt cttagtgcat ataacaaaca tagagacaaa   3900
ccaatacgtg aacaagcaga aaatattatt catttattta cgttgacgaa tcttggagct   3960
```

```
cccgctgctt ttaaatattt tgatacaaca attgatcgta aacgatatac gtctacaaaa    4020
gaagttttag atgccactct tatccatcaa tccatcactg gtctttatga aacacgcatt    4080
gatttgagtc agctaggagg tgactga                                        4107
```

<210> SEQ ID NO 39
<211> LENGTH: 1368
<212> TYPE: PRT
<213> ORGANISM: Streptococcus pyogenes

<400> SEQUENCE: 39

```
Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Ser Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350
```

```
Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
        370                 375                 380

Gly Thr Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
        755                 760                 765
```

```
Thr Thr Gln Lys Gly Gln Lys Asn Ser Arg Glu Arg Met Lys Arg Ile
    770             775                 780
Glu Glu Gly Ile Lys Glu Leu Gly Ser Gln Ile Leu Lys Glu His Pro
785             790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
                835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
                930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
                995             1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
```

```
                1175                1180                1185
Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 40
<211> LENGTH: 4107
<212> TYPE: DNA
<213> ORGANISM: Artificial Sequence
<220> FEATURE:
<223> OTHER INFORMATION: Synthetic polynucleotide

<400> SEQUENCE: 40
atggacaaga agtactccat cggcctcgcg atcggcacca actccgtggg ctgggcggtc    60
atcaccgacg agtacaaggt ccccctccaag aagttcaagg tcctgggcaa caccgaccgg   120
cactcgatca agaagaacct gatcggcgcc ctgctcttcg acagcggcga gaccgccgag   180
gcgacccgcc tgaagcggac cgcgcgtcgc cgctacaccc ggcgcaagaa ccgcatctgc   240
tacctgcagg aaatcttctc caacgagatg gccaaggtgg acgactcgtt cttccaccgc   300
ctggaggaga gcttcctggt ggaggaggac aagaagcacg agcgccaccc gatcttcggc   360
aacatcgtgg acgaggtggc ctaccacgag aagtacccca ccatcctacc cctccgcaag   420
aagctggtgg actcgaccga caaggcggac ctgcggctca tctacctggc cctcgcgcac   480
atgatcaagt ccgcggcca cttcctcatc gagggcgacc tgaacccgga caactccgac   540
gtggacaagc tcttcatcca gctggtgcag acctacaacc agctgttcga ggagaacccc   600
atcaacgcca gcggcgtgga cgccaaggcg atcctctccg cgcgcctgag caagtcccgg   660
cgcctggaga acctcatcgc ccagctgccg ggcgagaaga gaacggcct tcggcaac     720 ctgatcgcgc tgtcgctcgg cctgacccc aacttcaaga gcaacttcga cctggccgag   780
gacgcgaagc tccagctgtc caaggacacc tacgacgacg acctggacaa cctgctcgcc   840
cagatcggcg accagtacgc ggacctcttc ctggccgcga gaacctctc ggacgccatc   900 ctgctcagcg acatcctgcg ggtcaacacc gagatcacca aggcccgct gtcggcgagc   960
```

```
atgatcaagc ggtacgacga gcaccaccag gacctgaccc tgctcaaggc cctcgtgcgc    1020
cagcagctgc ccgagaagta caaggaaatc ttcttcgacc agtccaagaa cggctacgcc    1080
ggctacatcg acggcggcgc gtcgcaggag gagttctaca agttcatcaa gccgatcctg    1140
gagaagatgg acggcaccga ggagctgctc gtcaagctga accgcgagga cctgctccgc    1200
aagcagcgga ccttcgacaa cggctccatc ccgcaccaga tccacctggg cgagctccac    1260
gccatcctcc ggcgccagga ggacttctac cccttcctga aggacaaccg cgagaagatc    1320
gagaagatcc tgaccttccg catcccgtac tacgtcggcc ccctggcccg cggcaactcc    1380
cggttcgcgt ggatgacccg gaagtcggag gagaccatca ccccgtggaa cttcgaggag    1440
gtcgtggaca agggcgcgtc cgcgcagtcg ttcatcgagc gcatgaccaa cttcgacaag    1500
aacctcccga cgagaaggt cctgcccaag cactccctgc tctacgagta cttcaccgtg    1560
tacaacgagc tgaccaaggt caagtacgtg accgagggca tgcggaagcc ggccttcctg    1620
tcgggcgaga gaagaaggc gatcgtggac ctgctcttca agaccaaccg caaggtcacc    1680
gtgaagcagc tgaaggagga ctacttcaag aagatcgagt gcttcgactc cgtcgagatc    1740
agcggcgtgg aggaccgctt caacgcctcc ctgggcacct accacgacct gctcaagatc    1800
atcaaggaca aggacttcct cgacaacgag gagaacgagg acatcctgga ggacatcgtc    1860
ctcaccctga ccctcttcga ggaccgcgag atgatcgagg agcggctcaa gacctacgcc    1920
cacctgttcg acgacaaggt gatgaagcag ctgaagcgtc gccgctacac cggctggggc    1980
cgcctctccc ggaagctgat caacggcatc cgggacaagc agagcggcaa gaccatcctg    2040
gacttcctca gtccgacgg cttcgccaac cgcaacttca tgcagctcat ccacgacgac    2100
agcctgacct tcaaggagga catccagaag gcccaggtct cgggccaggg cgacagcctc    2160
cacgagcaca tcgccaacct ggcgggctcc ccggcgatca agaagggcat cctccagacc    2220
gtcaaggtcg tggacgagct ggtcaaggtg atgggccgcc acaagcccga gaacatcgtg    2280
atcgagatgg cccgggagaa ccagaccacc cagaagggcc agaagaactc gcgcgagcgg    2340
atgaagcgga tcgaggaggg catcaaggag ctcggcagcc agatcctgaa ggagcacccg    2400
gtcgagaaca cccagctgca gaacgagaag ctgtacctct actacctgca gaacggccgc    2460
gacatgtacg tggaccagga gctcgacatc aaccggctgt ccgactacga cgtggacgcg    2520
atcgtgccgc agtccttcct gaaggacgac tcgatcgaca caaggtcct gacccgctcg    2580 gacaagaacc ggggcaagtc cgacaacgtg ccctcggagg aggtcgtgaa gaagatgaag    2640
aactactggc gccagctgct caacgccaag ctcatcaccc agcgcaagtt cgacaacctg    2700
accaaggccg agcggggcgg cctgagcgag ctcgacaagg cgggcttcat caagcgccag    2760
ctggtcgaga cccggcagat caccaagcac gtggcccaga tcctggactc ccggatgaac    2820
accaagtacg acgagaacga caagctgatc cgcgaggtca aggtgatcac cctcaagagc    2880
aagctggtct ccgacttccg caaggacttc cagttctaca aggtccggga gatcaacaac    2940
taccaccacg cccacgacgc gtacctgaac gccgtcgtgg gcaccgcgct gatcaagaag    3000
tacccgaagc tggagtccga gttcgtctac ggcgactaca aggtctacga cgtgcgcaag    3060
atgatcgcca agagcgagca ggagatcggc aaggccaccg cgaagtactt cttctactcc    3120
aacatcatga acttcttcaa gaccgagatc accctggcca acggcgagat ccgcaagcgg    3180
cccctgatcg agaccaacgg cgagaccggc gagatcgtct gggacaaggg ccgcgacttc    3240
gccaccgtcc ggaaggtgct gtcgatgccg caggtcaaca tcgtgaagaa gaccgaggtg    3300
```

```
cagaccggcg gcttcagcaa ggagtccatc ctccccaagc gcaacagcga caagctgatc    3360
gcccggaaga aggactggga cccgaagaag tacggcggct cgacagccc caccgtcgcc    3420 tactccgtgc tggtcgtggc gaaggtcgag aagggcaaga gcaagaagct gaagtccgtg    3480
aaggagctgc tcggcatcac catcatggag cgctcctcgt tcgagaagaa cccgatcgac    3540
ttcctggagg ccaagggcta aaggaggtc aagaaggacc tcatcatcaa gctgcccaag    3600
tacagcctgt tcgagctgga gaacggccgc aagcggatgc tcgcctccgc gggcgagctg    3660
cagaagggca acgagctggc cctcccgtcg aagtacgtca acttcctgta cctcgcgtcc    3720
cactacgaga agctgaaggg ctcgcccgag gacaacgagc agaagcagct cttcgtggag    3780
cagcacaagc actacctgga cgagatcatc gagcagatca gcgagttcag caagcgcgtc    3840
atcctggccg acgcgaacct cgacaaggtg ctgtccgcct acaacaagca ccgcgacaag    3900
ccgatccggg agcaggcgga gaacatcatc cacctgttca ccctcaccaa cctgggcgcc    3960
cccgccgcgt tcaagtactt cgacaccacc atcgaccgca gcggtacac ctccaccaag    4020 gaggtcctcg acgcgaccct gatccaccag agcatcaccg cctgtacga acccgcatc    4080 gacctgtccc agctcggcgg cgactga                                       4107

<210> SEQ ID NO 41
<211> LENGTH: 1368
<212> TYPE: PRT
<213> ORGANISM: Artificial Sequence
<220> FEATURE:
<223> OTHER INFORMATION: Synthetic polypeptide

<400> SEQUENCE: 41

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220
```

-continued

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

-continued

His Leu Phe Asp Asp Lys Val Met Lys Gln Leu Lys Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

<210> SEQ ID NO 42
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 42
ctatgctggc ccccaccctg gccaactacc tgcggaaact g      41

<210> SEQ ID NO 43
<211> LENGTH: 41
<212> TYPE: DNA
<213> ORGANISM: Artificial Sequence

```
<220> FEATURE:
<223> OTHER INFORMATION: Synthetic polynucleotide

<400> SEQUENCE: 43
cagtttccgc aggtagttgg ccagggtggg ggccagcata g                    41

<210> SEQ ID NO 44
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 44
gcgacagctg catggtgttc ggcgacaccc tggacatc                        38

<210> SEQ ID NO 45
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 45
gatgtccagg gtgtcgccga acaccatgca gctgtcgc                        38

<210> SEQ ID NO 46
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 46
ctatgctggc cgccaccctg gccaactacc tgcggtaact g                    41

<210> SEQ ID NO 47
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 47
cagttaccgc aggtagttgg ccagggtggc ggccagcata g                    41

<210> SEQ ID NO 48
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 48
gcgacagctg catggtgttc ggcgacaccc tggacatc                        38

<210> SEQ ID NO 49
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 49
gatgtccagg gtgtcgccga acaccatgca gctgtcgc                        38
```

```
<210> SEQ ID NO 50
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 50
gtcagatccg ctagcacc                                                    18

<210> SEQ ID NO 51
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 51
cgatcgatat caattgtggt ttgtccaaac tcatca                                36

<210> SEQ ID NO 52
<211> LENGTH: 120
<212> TYPE: DNA
<213> ORGANISM: Artificial Sequence
<220> FEATURE:
<223> OTHER INFORMATION: gDNA template

<400> SEQUENCE: 52
taatacgact cactataggg agatcgactc tagaggatcc acgttttaga gctagaaata      60
cgaagttaaa ataaggctag tccgttatca acttgaaaaa gtggcaccga gtcggtgctt    120
```